US011696953B2

(12) United States Patent
Anderson et al.

(10) Patent No.: US 11,696,953 B2
(45) Date of Patent: Jul. 11, 2023

(54) POLY(BETA-AMINO ESTERS) AND USES THEREOF

(71) Applicant: Massachusetts Institute of Technology, Cambridge, MA (US)

(72) Inventors: Daniel Griffith Anderson, Framingham, MA (US); Kevin John Kauffman, Somerville, MA (US); James C. Kaczmarek, Wakefield, MA (US); Asha Kumari Patel, Ilford (GB)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 17/939,528

(22) Filed: Sep. 7, 2022

(65) Prior Publication Data

US 2023/0061974 A1 Mar. 2, 2023

Related U.S. Application Data

(62) Division of application No. 16/170,318, filed on Oct. 25, 2018, now Pat. No. 11,464,860.

(60) Provisional application No. 62/578,139, filed on Oct. 27, 2017.

(51) Int. Cl.
| | |
|---|---|
| *A61K 47/18* | (2017.01) |
| *A61K 9/19* | (2006.01) |
| *A61K 31/7088* | (2006.01) |
| *A61K 9/00* | (2006.01) |
| *C12N 15/88* | (2006.01) |
| *C08G 73/02* | (2006.01) |
| *A61K 9/12* | (2006.01) |
| *A61K 47/32* | (2006.01) |
| *A61K 47/34* | (2017.01) |
| *C08G 63/685* | (2006.01) |
| *A61P 11/00* | (2006.01) |
| *A61K 31/7105* | (2006.01) |
| *A61K 31/711* | (2006.01) |

(52) U.S. Cl.
CPC .......... *A61K 47/183* (2013.01); *A61K 9/0019* (2013.01); *A61K 9/12* (2013.01); *A61K 9/19* (2013.01); *A61K 31/7088* (2013.01); *A61K 47/32* (2013.01); *A61K 47/34* (2013.01); *C08G 63/6852* (2013.01); *C08G 63/6856* (2013.01); *C08G 63/6858* (2013.01); *C08G 73/02* (2013.01); *C12N 15/88* (2013.01); *A61K 31/711* (2013.01); *A61K 31/7105* (2013.01); *A61P 11/00* (2018.01)

(58) Field of Classification Search
CPC .... A61K 47/32; A61K 47/34; C08G 63/6856; C08G 63/6858
See application file for complete search history.

(56) References Cited

U.S. PATENT DOCUMENTS

| | | | |
|---|---|---|---|
| 2,759,913 | A | 8/1956 | Hulse |
| 3,963,771 | A | 6/1976 | Robson et al. |
| 4,224,365 | A | 9/1980 | Ali-Zaidi |
| 4,348,511 | A | 9/1982 | Haug |
| 4,883,689 | A | 11/1989 | Gradeff et al. |
| 5,180,424 | A | 1/1993 | Hutter |
| 5,364,634 | A | 11/1994 | Lew |
| 5,462,990 | A | 10/1995 | Hubbell et al. |
| 5,525,357 | A | 6/1996 | Keefer et al. |
| 5,573,934 | A | 11/1996 | Hubbell et al. |
| 5,705,188 | A | 1/1998 | Junichi et al. |
| 5,770,637 | A | 6/1998 | Vanderlaan et al. |
| 5,858,746 | A | 1/1999 | Hubbell et al. |
| 5,904,927 | A | 5/1999 | Amiji |
| 5,962,520 | A | 10/1999 | Smith et al. |
| 6,060,582 | A | 5/2000 | Hubbell et al. |
| 6,444,725 | B1 | 9/2002 | Trom et al. |
| 6,984,404 | B1 | 1/2006 | Talton et al. |
| 6,998,115 | B2 | 2/2006 | Langer |
| 7,427,394 | B2 | 9/2008 | Anderson et al. |
| 8,071,082 | B2 | 12/2011 | Zugates et al. |
| RE43,612 | E | 8/2012 | Anderson et al. |
| 8,287,849 | B2 | 10/2012 | Langer et al. |
| 8,557,231 | B2 | 10/2013 | Langer et al. |
| 8,562,966 | B2 | 10/2013 | Zugates et al. |
| 8,748,551 | B2 | 6/2014 | Puerta et al. |
| 8,808,681 | B2 | 8/2014 | Anderson et al. |
| 9,101,666 | B2 | 8/2015 | Langer et al. |
| 9,700,627 | B2 | 7/2017 | Langer et al. |
| 11,041,069 | B2 | 6/2021 | Palmiero et al. |
| 11,464,860 | B2 | 10/2022 | Anderson et al. |
| 2001/0048940 | A1 | 12/2001 | Tousignant et al. |

(Continued)

FOREIGN PATENT DOCUMENTS

| | | |
|---|---|---|
| CN | 111718494 A | 9/2020 |
| DE | 16 68 502 A1 | 9/1971 |

(Continued)

OTHER PUBLICATIONS

Extended European Search Report, dated Jan. 28, 2008, for EP 07013193.3.
Invitation to Pay Additional Fees for PCT/US2004/016521 dated Sep. 29, 2004.
International Search Report and Written Opinion for PCT/US2004/016521 dated Dec. 8, 2004.
International Preliminary Report on Patentability for PCT/US2004/016521 dated Dec. 15, 2005.

(Continued)

*Primary Examiner* — James W Rogers
(74) *Attorney, Agent, or Firm* — Wolf, Greenfield & Sacks, P.C.

(57) ABSTRACT

Provided herein are branched poly(beta-amino esters) (PBAE) useful as vehicles for the delivery of therapeutic agents, such as nucleic acids. The disclosed polymers form stable compositions, and are suitable for the delivery of therapeutic agents via nebulization. Compositions of the disclosed polymers are capable of delivering therapeutic agents such as mRNA to l

(56) References Cited

U.S. PATENT DOCUMENTS

| | | | |
|---|---|---|---|
| 2002/0131951 | A1 | 9/2002 | Langer et al. |
| 2004/0028694 | A1 | 2/2004 | Young et al. |
| 2004/0071654 | A1 | 4/2004 | Anderson et al. |
| 2004/0175328 | A1 | 9/2004 | Sutton et al. |
| 2005/0059005 | A1 | 3/2005 | Tuschl et al. |
| 2005/0122550 | A1 | 6/2005 | Plewa et al. |
| 2005/0238716 | A1 | 10/2005 | Verrijk et al. |
| 2005/0244504 | A1 | 11/2005 | Little et al. |
| 2005/0265961 | A1 | 12/2005 | Langer et al. |
| 2006/0062821 | A1 | 3/2006 | Simhambhatla et al. |
| 2006/0105975 | A1 | 5/2006 | Pendergrast et al. |
| 2007/0178126 | A1 | 8/2007 | Angot et al. |
| 2008/0145338 | A1 | 6/2008 | Anderson et al. |
| 2008/0242626 | A1 | 10/2008 | Zugates et al. |
| 2010/0036084 | A1 | 2/2010 | Langer et al. |
| 2010/0196492 | A1 | 8/2010 | Green et al. |
| 2012/0065358 | A1 | 3/2012 | Langer et al. |
| 2012/0149630 | A1 | 6/2012 | Zugates et al. |
| 2012/0294944 | A1 | 11/2012 | Emanuel et al. |
| 2013/0302401 | A1 | 11/2013 | Ma et al. |
| 2014/0094399 | A1 | 4/2014 | Langer et al. |
| 2014/0271861 | A1 | 9/2014 | Emanuel |
| 2015/0273071 | A1 | 10/2015 | Green et al. |
| 2016/0022821 | A1 | 1/2016 | Langer et al. |
| 2017/0216455 | A1 | 8/2017 | Wang et al. |
| 2019/0125874 | A1 | 5/2019 | Anderson et al. |
| 2019/0194390 | A1 | 6/2019 | Capasso Palmiero et al. |
| 2019/0194444 | A1 | 6/2019 | Capasso Palmiero et al. |
| 2020/0172663 | A1 | 6/2020 | Kaczmarek et al. |
| 2021/0388196 | A1 | 12/2021 | Capasso Palmiero et al. |
| 2022/0287983 | A1 | 9/2022 | Traverso et al. |

FOREIGN PATENT DOCUMENTS

| | | |
|---|---|---|
| DE | 2520814 A1 | 11/1976 |
| DE | 19626567 A1 | 1/1998 |
| EP | 0959092 A1 | 11/1999 |
| EP | 1489126 A1 | 12/2004 |
| GB | 1257638 A | 12/1971 |
| JP | 52-045327 A | 4/1977 |
| JP | H06-122731 A | 5/1994 |
| JP | 08-092369 A | 4/1996 |
| JP | 2004-506000 A | 2/2004 |
| WO | WO 98/16202 A2 | 4/1998 |
| WO | WO 02/13767 A2 | 2/2002 |
| WO | WO 2002/031025 A2 | 4/2002 |
| WO | WO 2004/106411 A2 | 12/2004 |
| WO | WO 2006/138380 A2 | 12/2006 |
| WO | WO 2008/011561 A2 | 1/2008 |
| WO | WO 2014/136100 A1 | 9/2014 |
| WO | WO 2016/020474 A1 | 2/2016 |
| WO | WO 2020/077347 A2 | 4/2020 |

OTHER PUBLICATIONS

International Search Report and Written Opinion for PCT/US2008/056168 dated Nov. 6, 2008.
International Preliminary Report on Patentability for PCT/US2008/056168 dated Sep. 17, 2009.
International Search Report for PCT/US2001/031270 dated May 22, 2002.
Written Opinion for PCT/US2001/031270 dated Jan. 2, 2003.
International Preliminary Examination Report for PCT/US2001/031270 dated Aug. 19, 2003.
Extended European Search Report for EP 07813156.2 dated Oct. 5, 2009.
International Search Report and Written Opinion for PCT/US2007/073976 dated Sep. 29, 2008.
International Preliminary Report on Patentability for PCT/US2007/073976 dated Feb. 5, 2009.
Extended European Search Report for EP 07798132.2 dated Jul. 18, 2011.
International Search Report and Written Opinion for PCT/US2007/070430 dated Dec. 13, 2007.
International Preliminary Report on Patentability for PCT/US2007/070430 dated Dec. 24, 2008.
International Search Report and Written Opinion for PCT/US2018/057448 dated Feb. 21, 2019.
International Preliminary Report on Patentability for PCT/US2018/057448 dated May 7, 2020.
International Search Report and Written Opinion for PCT/US2018/058898, dated Feb. 22, 2019.
International Preliminary Report on Patentability for PCT/US2018/058898, dated May 14, 2020.
International Search Report and Written Opinion for PCT/US2018/058985, dated Feb. 26, 2019.
International Preliminary Report on Patentability for PCT/US2018/058985 dated May 14, 2020.
International Search Report and Written Opinion for PCT/US2019/058064, dated Apr. 9, 2020.
International Preliminary Report on Patentability for PCT/US2019/058064, dated May 6, 2021.
International Search Report and Written Opinion for PCT/US2022/019236, dated May 30, 2022.
[No Author Listed], HIV Vaccine Failure Prompts Merck to Halt Trial. Nature. 2007;449:390.
Abramson et al., Oral mRNA delivery using capsule-mediated gastrointestinal tissue injections. Matter. Mar. 2, 2022;5(3):975-87. doi: 10.1016/j.matt.2021.12.022.
Akhtar et al., Toxicogenomics of non-viral drug delivery systems for RNAi: potential impact on siRNA-mediated gene silencing activity and specificity. Advanced drug delivery reviews 2007, 59 (2-3), 164-82.
Akinc et al., A combinatorial library of lipid-like materials for delivery of RNAi; therapeutics. Nat Biotechnol. May 2008;26(5):561-9. doi: 10.1038/nbt1402. Epub; Apr. 27, 2008.
Akinc et al., Measuring the pH environment of DNA delivered using nonviral vectors: implications for lysosomal trafficking. Biotechnol Bioeng. Jun. 5, 2002;78(5):503-8.
Akinc et al., Parallel synthesis and biophysical characterization of a degradable polymer library for gene delivery. J Am Chem Soc. May 7, 2003;125(18):5316-23.
Akinc et al., Synthesis of poly(beta-amino ester)s optimized for highly effective gene delivery. Bioconjug Chem. Sep.-Oct. 2003;14(5):979-88. doi: 10.1021/bc034067y.
Allison, The mode of action of immunological adjuvants. Dev Biol Stand. 1998;92:3-11.
Anderson et al., A polymer library approach to suicide gene therapy for cancer. Proc Natl Acad Sci USA. Nov. 9, 2004;101(45):16028-33. Epub Nov. 1, 2004.
Anderson et al., Biodegradation and biocompatibility of PLA and PLGA microspheres. Adv Drug Deliv Rev. Oct. 13, 1997;28(1):5-24.
Anderson et al., Nanoliter-scale synthesis of arrayed biomaterials and application to human embryonic stem cells. Nat Biotechnol. Jul. 2004;22(7):863-6. Epub Jun. 13, 2004.
Anderson et al., Structure/property studies of polymeric gene delivery using a library of poly(beta-amino esters). Mol Ther. Mar. 2005;11(3):426-34.
Anderson, Human gene therapy. Nature. Apr. 30, 1998;392(6679 Suppl):25-30.
Ando et al., PLGA microspheres containing plasmid DNA: preservation of supercoiled DNA via cryopreparation and carbohydrate stabilization. J Pharm Sci. Jan. 1999;88(1):126-30.
Angeloni et al., Liquid crystalline poly (β-aminoester)s containing different mesogenic groups. Makromlekulare Chemie. 1985;186:977-97.
Anseth et al., In situ forming degradable networks and their application in tissue engineering and drug delivery. J Control Release. Jan. 17, 2002;78(1-3):199-209.
Anseth et al., New Directions in Photopolymerizable Biomaterials. Mrs Bull. 2002;27:130-136.
Anseth et al., Photopolymerizable degradable polyanhydrides with osteocompatibility. Nat Biotechnol. Feb. 1999;17(2):156-9.

(56) References Cited

OTHER PUBLICATIONS

Anseth et al., Polymeric Dental Composites: Properties and Reaction Behavior of Multimethacrylate Dental Restorations. Advances in Polymer Science. 1995;122:177-217.
Arote et al., A biodegradable poly(ester amine) based on polycaprolactone and polyethylenimine as a gene carrier. Biomaterials. Feb. 2007;28(4):735-44. Epub Oct. 10, 2006.
Bals et al., Innate immunity in the lung: how epithelial cells fight against respiratory pathogens. Eur Respir J. Feb. 2004;23(2):327-33.
Bantikassegn et al., Isolation of epithelial, endothelial, and immune cells from lungs of transgenic mice with oncogene-induced lung adenocarcinomas. Am J Respir Cell Mol Biol. Apr. 2015;52(4):409-17. doi:10.1165/rcmb.2014-0312MA.
Barbucci et al. Macroinorganics. 7. Property-Structure Relationships for Polymeric Bases Whose Monomeric Units Behave Independently towards Protonation. Macromolecules 1981;14:1203-09.
Barbucci et al., Protonation studies of multifunctional polymers with a poly(amido-amine) structure. Polymer. 1978;19:1329-34.
Barbucci et al., Thermodynamic and 13C n.m.r. data on the protonation of polymeric bases whose repeating units behave independently towards protonation. Polymer. 1980;21:81-85.
Barrera et al., Synthesis and RGD Peptide Modification of a New Biodegradable Copolymer: Poly(lactic acid-co-lysine). J Am Chem Soc. 1993;115:11010-11.
Beebe et al., Microfluidic tectonics: a comprehensive construction platform for microfluidic systems. Proc Natl Acad Sci U S A. Dec. 5, 2000;97(25):13488-93.
Behr, Synthetic Gene-Transfer Vectors. Acc Chem Res. 1993;26:274-78.
Behr, The Proton Sponge: a Trick to Enter Cells the Viruses Did Not Exploit. Chimia. 1997;51:34-36.
Benns et al., pH-sensitive cationic polymer gene delivery vehicle: N-Ac-poly(L-histidine)-graft-poly(L-lysine) comb shaped polymer. Bioconjug Chem. Sep.-Oct. 2000;11(5):637-45.
Blake et al., Organocatalytic ring-opening polymerization of morpholinones: new strategies to functionalized polyesters. J Am Chem Soc. Jul. 2, 2014;136(26):9252-5. doi: 10.1021/ja503830c. Epub Jun. 19, 2014.
Blanco et al., Principles of nanoparticle design for overcoming biological barriers to drug delivery. Nat Biotechnol. Sep. 2015;33(9):941-51. doi:10.1038/nbt.3330.
Bobo et al., Nanoparticle-Based Medicines: A Review of FDA-Approved Materials and Clinical Trials to Date. Pharmaceutical Research, 2016, 33, 2373-2387.
Boussif et al., A versatile vector for gene and oligonucleotide transfer into cells in culture and in vivo: polyethylenimine. Proc Natl Acad Sci U S A. Aug. 1, 1995;92(16):7297-301.
Brazeau et al., In vitro myotoxicity of selected cationic macromolecules used in non-viral gene delivery. Pharm Res. May 1998;15(5):680-4.
Brey et al., Controlling poly(beta-amino ester) network properties through macromer branching. Acta Biomater. Mar. 2008;4(2):207-17. Epub Oct. 22, 2007.
Brey et al., Influence of macromer molecular weight and chemistry on poly(beta-amino ester) network properties and initial cell interactions. J Biomed Mater Res A. Jun. 1, 2008;85(3):731-41.
Brocchini et al., A Combinatorial Approach for Polymer Designs. J Am Chem Soc. 1997;119:4553-54.
Brocchini, Combinatorial chemistry and biomedical polymer development. Adv Drug Deliv Rev. Dec. 3, 2001;53(1):123-30.
Bryant et al., Cytocompatibility of UV and visible light photoinitiating systems on cultured NIH/3T3 fibroblasts in vitro. J Biomater Sci Polym Ed. 2000; 11(5):439-57.
Burdick et al., Photoencapsulation of osteoblasts in injectable RGD-modified PEG hydrogels for bone tissue engineering. Biomaterials. Nov. 2002;23(22):4315-23.
Burdick et al., Stimulation of neurite outgrowth by neurotrophins delivered from degradable hydrogels. Biomaterials. Jan. 2006;27(3):452-9. Epub Aug. 22, 2005.

Byk et al., Synthesis, activity, and structure—activity relationship studies of novel cationic lipids for DNA transfer. J Med Chem. Jan. 15, 1998;41(2):229-35. doi: 10.1021/jm9704964.
Byloos et al., Phase Transitions of Alkanethiol Self-Assembled Monolayers at an Electrified Gold Surface. J Phys Chem B. 2001;105:5900-05.
Caminschi et al., Molecular cloning of F4/80-like-receptor, a seven-span membrane protein expressed differentially by dendritic cell and monocyte-macrophage subpopulations. J Immunol. Oct. 1, 2001;167(7):3570-6.
Capan et al., Preparation and characterization of poly (D,L-lactide-co-glycolide) microspheres for controlled release of poly(L-lysine) complexed plasmid DNA. Pharm Res. Apr. 1999;16(4):509-13.
Carai et al., Central Effects of 1,4-Butanediol are Mediated by GABA(B) Receptors via its Conversion into γ-Hydroxybutyric Acid. European Journal of Pharmacology, 2002, 441, 157-163.
Carothers, Polymers and Polyfunctionality. Transactions of the Faraday Society, 1936, 32, 39-49.
Casimiro et al., Vaccine-induced immunity in baboons by using DNA and replication-incompetent adenovirus type 5 vectors expressing a human immunodeficiency virus type 1 gag gene. J Virol. Jul. 2003;77(13):7663-8.
Chan et al., Triplex DNA: fundamentals, advances, and potential applications for gene therapy. J Mol Med. Apr. 1997;75(4):267-82.
Chen et al., Production and Clinical Development of Nanoparticles for Gene Delivery. Mol. Ther. Methods Clin. Dev., 2016, 3, 16023.
Chen et al., Rapid discovery of potent siRNA-containing lipid nanoparticles enabled by controlled microfluidic formulation. J Am Chem Soc. Apr. 25, 2012;134(16):6948-51. doi: 10.1021/ja301621z. Epub Apr. 10, 2012.
Cho et al., A proposed mechanism for the induction of cytotoxic T lymphocyte production by heat shock fusion proteins. Immunity. Mar. 2000;12(3):263-72.
Cho et al., Homeostasis-stimulated proliferation drives cotton T cells to differentiate directly into memory T cells. J Exp Med. Aug. 21, 2000;192(4):549-56.
Choksakulnimitr et al., In vitro cytotoxicity of macromolecules in different cell culture systems. J Control Rel. 1995;34:233-41.
Cotten et al., Receptor-mediated transport of DNA into eukaryotic cells. Methods Enzymol. 1993;217:618-44.
Crooke, Evaluating the mechanism of action of antiproliferative antisense drugs. Antisense Nucleic Acid Drug Dev. Apr. 2000;10(2):123-6; discussion 127.
Crooke, Molecular mechanisms of action of antisense drugs. Biochim Biophys Acta. Dec. 10, 1999;1489(1):31-44.
Crystal, Transfer of genes to humans: early lessons and obstacles to success. Science. Oct. 20, 1995;270(5235):404-10.
Dahlman et al., In vivo endothelial siRNA delivery using polymeric nanoparticles with low molecular weight. Nature nanotechnology 2014;9 (8):648-55.
Danusso et al., Nuovi alti polimeri da poliaddizione di piperazina o 2-metilpiperazina a diesteri acrilici o divinilsolfone. Chim Ind (Milan). 1967;49:826-30. Italian.
Danusso et al., Synthesis of tertiary amine polymers. Polymer. 1970;11:88-113.
Dash et al., Poly-ε-caprolactone Based Formulations for Drug Delivery and Tissue Engineering: A Review. Journal of Controlled Release, 2012, 158, 15-33.
Dash et al., Polymeric modification and its implication in drug delivery: poly-ε-caprolactone (PCL) as a model polymer. Mol Pharm. Sep. 4, 2012;9(9):2365-79. doi: 10.1021/mp3001952. Epub Aug. 14, 2012.
Davis, The first targeted delivery of siRNA in humans via a self-assembling, cyclodextrin polymer-based nanoparticle: from concept to clinic. Molecular pharmaceutics 2009;6(3):659-68.
De Smedt et al., Cationic polymer based gene delivery systems. Pharm Res. Feb. 2000;17(2):113-26.
Demeneix et al., Chapter 14. The Proton Sponge: A Trick the Viruses Did Not Exploit. Artificial Self Assembly Systems for Gene Delivery (Felgner et al Eds). 1996:146-51.
Deshmukh et al., Liposome and polylysine mediated gene transfer. New J Chem. 1997;21:113-24.

(56) References Cited

OTHER PUBLICATIONS

Dong et al., Lipopeptide nanoparticles for potent and selective siRNA delivery in rodents and nonhuman primates. Proc Natl Acad Sci U S A. Mar. 18, 2014;111(11):3955-60. doi: 10.1073/pnas.1322937111. Epub Feb. 10, 2014. Erratum in: Proc Natl Acad Sci U S A. Apr. 15, 2014;111(15):5753.
Dowdy, Overcoming cellular barriers for RNA therapeutics. Nat Biotechnol. Mar. 2017;35(3):222-229. doi: 10.1038/nbt.3802. Epub Feb. 27, 2017.
Draghici et al., Synthetic nucleic acid delivery systems: present and perspectives. J Med Chem. May 28, 2015;58(10):4091-130. doi: 10.1021/jm500330k. Epub Feb. 20, 2015.
Eddington et al., Flow control with hydrogels. Adv Drug Deliv Rev. Feb. 10, 2004;56(2):199-210.
Elisseeff et al., Transdermal photopolymerization for minimally invasive implantation. Proc Natl Acad Sci U S A. Mar. 16, 1999;96(6):3104-7.
Eltoukhy et al., Degradable terpolymers with alkyl side chains demonstrate enhanced gene delivery potency and nanoparticle stability. Adv Mater. Mar. 13, 2013;25(10):1487-93. doi:10.1002/adma.201204346. Epub Jan. 4, 2013.
Eltoukhy et al., Effect of molecular weight of amine end-modified poly(β-amino ester)s on gene delivery efficiency and toxicity. Biomaterials. May 2012;33(13):3594-603. doi:10.1016/j.biomaterials.2012.01.046. Epub Feb. 14, 2012.
Fahnhorst et al., Synthesis and Study of Sustainable Polymers in the Organic Chemistry Laboratory: An Inquiry-Based Experiment Exploring the Effects of Size and Composition on the Properties of Renewable Block Polymers. In: Green Chemistry Experiments in Undergraduate Laboratories. ACS Symposium Series. Fahey et al., Eds. American Chemical Society. 2016. Chapter 8, pp. 123-147.
Fenton et al., Bioinspired Alkenyl Amino Alcohol Ionizable Lipid Materials for Highly Potent In Vivo mRNA Delivery. Adv Mater. Apr. 20, 2016;28(15):2939-43. doi: 10.1002/adma.201505822. Epub Feb. 18, 2016.
Fenton et al., Synthesis and Biological Evaluation of Ionizable Lipid Materials for the In Vivo Delivery of Messenger RNA to B Lymphocytes. Adv Mater. Sep. 2017;29(33). doi: 10.1002/adma.201606944. Epub Jul. 6, 2017.
Ferrari et al., ε-Caprolactone-based Macromonomers Suitable for Biodegradable Nanoparticles Synthesis Through Free Radical Polymerization. Macromolecules, 2011, 44, 9205-9212.
Ferruti et al., A novel modification of poly(l-lysine) leading to a soluble cationic polymer with reduced toxicity and with potential as a transfection agent. Macromol Chem Phys 1998;199:2565-75.
Ferruti et al., Linear Amino Polymers: Synthesis, Protonation and Complex Formation. Advances in Polymer Sci. 1984;58:55-92.
Ferruti et al., Recent results on functional polymers and macromonomers of interest as biomaterials or for biomaterial modification. Biomaterials. Dec. 1994;15(15):1235-41.
Ferruti et al., Synthesis, characterisation and antitumour activity of platinum (II) complexes of novel functionalised poly(amido amine)s. Macromol Chem Phys. 1999;200:1644-54.
Ferruti et al., Synthesis, physico-chemical properties and biomedical applications of poly(amido-amine)s. Polymer. 1985;26:1336-48.
Field et al., A simple predictive model for spherical indentation. J Mater Res. 1993;8(2):297-306.
Fire et al., Potent and specific genetic interference by double-stranded RNA in Caenorhabditis elegans. Nature. Feb. 19, 1998;391(6669):806-11.
Fisher et al., Photoinitiated Polymerization of Biomaterials. Annu Rev Mater Res. 2001;31:171-181.
Fisher et al., Synthesis and properties of photocross-linked poly(propylene fumarate) scaffolds. J Biomater Sci Polym Ed. 2001;12(6):673-87.
Flory, Principles of Polymer Chemistry. Cornell University Press. Ithaca, New York. 1953:40-46, 318-23.
Fominaya et al., Target cell-specific DNA transfer mediated by a chimeric multidomain protein. Novel non-viral gene delivery system. J Biol Chem. May 3, 1996;271(18):10560-8.

Friedmann, Human gene therapy-an immature genie, but certainly out of the bottle. Nat Med. Feb. 1996;2(2):144-7.
Fritz et al., Gene transfer into mammalian cells using histone-condensed plasmid DNA. Hum Gene Ther. Aug. 1, 1996;7(12):1395-404.
Fu et al., Visual Evidence of Acidic Environment Within Degrading Poly(lactic-co-glycolic acid) (PLGA) Microspheres. Pharma Res. 2000;17(1):100-06.
Garg et al., Genetic tagging shows increased frequency and longevity of antigen-presenting, skin-derived dendritic cells in vivo. Nat Immunol. Sep. 2003;4(9):907-12. Epub Aug. 10, 2003. Corrigendum Nat Immunol Oct. 2003;4(10):1037.
Gebhart et al., Evaluation of polyplexes as gene transfer agents. J Control Release. Jun. 15, 2001;73(2-3):401-16.
Gerasimov et al., Cytosolic drug delivery using pH- and light-sensitive liposomes. Adv Drug Deliv Rev. Aug. 20, 1999;38(3):317-338.
Gilboa et al., Cancer Immunotherapy with mRNA-transfected Dendritic Cells. Immunological Reviews, 2004, 199, 251-263.
Gonzalez et al., New class of polymers for the delivery of macromolecular therapeutics. Bioconjug Chem. Nov.-Dec. 1999;10(6):1068-74.
Gore et al., Executive Summary to EDC-2: The Endocrine Society's Second Scientific Statement on Endocrine-Disrupting Chemicals. Endocrine Reviews, 2015, 36, 593-602.
Gori et al., Delivery and Specificity of CRISPR/Cas9 Genome Editing Technologies for Human Gene Therapy. Human Gene Therapy, 2015, 26, 443-451.
Green et al., A combinatorial polymer library approach yields insight into nonviral gene delivery. Acc Chem Res. Jun. 2008;41(6):749-59. doi: 10.1021/ar7002336.
Green et al., Biodegradable polymeric vectors for gene delivery to human endothelial cells. Bioconjug Chem. Sep.-Oct. 2006;17(5):1162-9.
Green et al., Poly(beta-amino esters): procedures for synthesis and gene delivery. Methods Mol Biol. 2009;480:53-63. doi: 10.1007/978-1-59745-429-2_4.
Green et al., The role of the endothelium in asthma and chronic obstructive pulmonary disease (COPD). Respir Res. Jan. 18, 2017;18(1):20. doi:10.1186/s12931-017-0505-1.
Grumelli et al., An immune basis for lung parenchymal destruction in chronic obstructive pulmonary disease and emphysema. PLoS Med. Oct. 2004;1(1):e8. Epub Oct. 19, 2004.
Guan et al., Nanotechnologies in delivery of mRNA therapeutics using nonviral vector-based delivery systems. Gene Ther. Mar. 2017;24(3):133-143. doi:10.1038/gt.2017.5. Epub Jan. 17, 2017.
Guerrero-Cázares et al., Biodegradable Polymeric Nanoparticles Show High Efficacy and Specificity at DNA Delivery to Human Glioblastoma in Vitro and in Vivo. ACS Nano, 2014, 8, 5141-5153.
Haensler et al., Polyamidoamine cascade polymers mediate efficient transfection of cells in culture. Bioconjug Chem. Sep.-Oct. 1993;4(5):372-9.
Hanes et al., New advances in microsphere-based single-dose vaccines. Adv Drug Deliv Rev. Oct. 13, 1997;28(1):97-119.
Hansen et al., Re-examination and further development of a precise and rapid dye method for measuring cell growth/cell kill. J Immunol Methods. May 12, 1989;119(2):203-10.
Hao et al., Progress towards the Synthesis of Amino Polyesters via Ring-Opening Polymerization (ROP) of Functional Lactones. Synlett 2016; 27(16): 2285-2292. DOI: 10.1055/s-0035-1562505.
Hao et al., Rapid Synthesis of a Lipocationic Polyester Library via Ring-Opening Polymerization of Functional Valerolactones for Efficacious siRNA Delivery. Journal of the American Chemical Society 2015;137(29):9206-9.
Hashemi et al., Preparation of Effective and Safe Gene Carriers by Grafting Alkyl Chains to Generation 5 Polypropyleneimine. AAPS PharmSciTech. Oct. 2015;16(5):1002-12. doi: 10.1208/s12249-015-0284-2. Epub Jan. 22, 2015.
Hashimoto et al., Electroporation Enables the Efficient mRNA Delivery into the Mouse Zygotes and Facilitates CRISPR/Cas9-based Genome Editing. Scientific Reports, 2015, 5.
Haugland, Handbook of Fluorescent Probes and Research Chemicals. 6th ed. Molecular Probes, Inc. 1996:29.

(56) References Cited

OTHER PUBLICATIONS

He et al., Experimental Investigation into One-Step and Two-Steps Polymerization Via Michael Addition from Primary Amine. Polymer Preprints. 2001;42(2):335-36.
Hedley et al., Microspheres containing plasmid-encoded antigens elicit cytotoxic T-cell responses. Nat Med. Mar. 1998;4(3):365-8.
Hill et al., In vitro cytotoxicity of poly(amidoamine)s: relevance to DNA delivery. Biochim Biophys Acta. Apr. 19, 1999;1427(2):161-74.
Hofland et al., Formation of stable cationic lipid/DNA complexes for gene transfer. Proc Natl Acad Sci U S A. Jul. 9, 1996;93(14):7305-9. doi: 10.1073/pnas.93.14.7305.
Hope et al., Cationic lipids, phosphatidylethanolamine and the intracellular delivery of polymeric, nucleic acid-based drugs (review). Mol Membr Biol.; Jan.-Mar. 1998;15(1):1-14.
Huang et al., Long-term in vivo gene expression via delivery of PEI-DNA condensates from porous polymer scaffolds. Hum Gene Ther. May 2005;16(5):609-17.
Hutchison et al., Robust polymer microfluidic device fabrication via contact liquid photolithographic polymerization (CLiPP). Lab Chip. 2004;4:658-662.
Hwang et al., Effects of structure of beta-cyclodextrin-containing polymers on gene delivery. Bioconjug Chem. Mar.-Apr. 2001;12(2):280-90.
Irfan et al., Synthesis and meticulous molecular, morphological and thermal characterization of linear and star-shaped polycaprolactones. RSC Adv. Oct. 10, 2016;6:98117-27. doi: 10.1039/C6RA23890D.
Jerome et al., Recent advances in the synthesis of aliphatic polyesters by ringopening polymerization. Advanced drug delivery reviews. 2008;60(9):1056-76.
Jin et al., Current Progress in Gene Delivery Technology Based on Chemical Methods and Nano-carriers. Theranostics 2014, 4, 240-255.
Kabanov et al., DNA complexes with polycations for the delivery of genetic material into cells. Bioconjug Chem. Jan.-Feb. 1995;6(1):7-20.
Kabanov, Taking polycation gene delivery systems from in vitro to in vivo. Pharm Sci Technolo Today. Sep. 1999;2(9):365-372.
Kaczmarek et al., Advances in the delivery of RNA therapeutics: from concept to clinical reality. Genome Med. Jun. 27, 2017;9(1):60. doi: 10.1186/s13073-017-0450-0.
Kamaly et al., Degradable Controlled-Release Polymers and Polymeric Nanoparticles: Mechanisms of Controlling Drug Release. Chemical reviews. 2016;116 (4), 2602-63.
Kamat et al., Lung Cancer in Vitro and in Vivo. Molecular Cancer Therapeutics, 2013, 12, 405-415.
Kanasty et al., Delivery materials for siRNA therapeutics. Nat Mater. Nov. 2013;12(11):967-77. doi: 10.1038/nmat3765.
Kargina et al., Self-Splitted Water-Soluble Ionogenic Polymers. Vysokomol Soedin Seriya. 1986;28:1139-44. Russian.
Kauffman et al., Materials for non-viral intracellular delivery of messenger RNA therapeutics. J Control Release. Oct. 28, 2016;240:227-234. doi: 10.1016/j.jconrel.2015.12.032. Epub Dec. 21, 2015.
Kauffman et al., Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021/acs.nanolett.5b02497. Epub Oct. 20, 2015.
Kawata et al., Finer features for functional microdevices. Nature. Aug. 16, 2001;412(6848):697-8.
Kay et al., Viral vectors for gene therapy: the art of turning infectious agents into vehicles of therapeutics. Nat Med. Jan. 2001;7(1):33-40.
Khademhosseini et al., Molded polyethylene glycol microstructures for capturing cells within microfluidic channels. Lab Chip. Oct. 2004;4(5):425-30. Epub Jul. 26, 2004.
Khosravi-Darani et al., Calcium Based Non-viral Gene Delivery: An Overview of Methodology and Applications. Acta Med Iranica, 2010, 48, 133-141.
Kim et al., Differential polymer Strucute Tunes Mechanism of Cellular Uptake and Transfection Routes of Poly (β-amino ester) Polyplexes in Human Breast Cancer Cells. Bioconjugate Chemistry, 2013, 25, 43-51.
Kim et al., Persistent activation of an innate immune response translates respiratory viral infection into chronic lung disease. Nat Med. Jun. 2008;14(6):633-40. doi:10.1038/nm1770. Epub May 18, 2008.
Kim et al., Synthesis of biodegradable cross-linked poly(beta-amino ester) for gene delivery and its modification, inducing enhanced transfection efficiency and stepwise degradation. Bioconjug Chem. Sep.-Oct. 2005;16(5):1140-8.
Kranz et al., Systemic RNA Delivery to Dendritic Cells Exploits Antiviral Defence for Cancer Immunotherapy. Nature, 2016, 534, 396-401.
Kukowska-Latallo et al., Efficient transfer of genetic material into mammalian cells using Starburst polyamidoamine dendrimers. Proc Natl Acad Sci U S A. May 14, 1996;93(10):4897-902.
Kumari et al., Biodegradable Polymeric Nanoparticles Based Drug Delivery Systems. Colloids and Surfaces B: Biointerfaces, 2010, 75, 1-18.
Kunath et al., Integrin targeting using RGD-PEI conjugates for in vitro gene transfer. J Gene Med. Jul. 2003;5(7):588-99.
Kursa et al., Novel shielded transferrin-poly ethylene glycol-polyethylenimine/DNA complexes for systemic tumor-targeted gene transfer. Bioconjug Chem. Jan.-Feb. 2003;14(1):222-31.
Kweon et al., A novel degradable polycaprolactone networks for tissue engineering. Biomaterials. Feb. 2003;24(5):801-8. doi: 10.1016/s0142-9612(02)00370-8.
Kwon et al., Pseudopoly(amino acids): A Study of the Synthesis and Characterization of Poly(trans-4-hydroxy-N-acyl-l-proline esters). Macromolecules. 1989;22:3250-55.
Leach et al., Bone engineering by controlled delivery of osteoinductive molecules and cells. Expert Opin Biol Ther. Jul. 2004;4(7):1015-27.
Leach et al., Photocrosslinked hyaluronic acid hydrogels: natural, biodegradable tissue engineering scaffolds. Biotechnology and Bioengineering. 2003;82:578-589.
Ledley, Nonviral gene therapy: the promise of genes as pharmaceutical products. Hum Gene Ther. Sep. 1995;6(9):1129-44.
Leus et al., VCAM-1 specific PEGylated SAINT-based lipoplexes deliver siRNA to activated endothelium in vivo but do not attenuate target gene expression. Int J Pharm. Jul. 20, 2014;469(1):121-31. doi: 10.1016/j.ijpharm.2014.04.041. Epub Apr. 18, 2014.
Li et al., Lipid-based nanoparticles for nucleic acid delivery. Pharm Res. Mar. 2007;24(3):438-49. doi: 10.1007/s11095-006-9180-5.
Lim et al., A Self-Destroying Polycationic Polymer: Biodegradable Poly(4-hydroxy-l-proline ester). J Am Chem Soc. 1999;121:5633-39.
Lim et al., Biodegradable, endosome disruptive, and cationic network-type polymer as a highly efficient and nontoxic gene delivery carrier. Bioconjug Chem. Sep.-Oct. 2002;13(5):952-7.
Lim et al., Cationic hyperbranched poly(amino ester): a novel class of DNA condensing molecule with cationic surface, biodegradable three-dimensional structure, and tertiary amine groups in the interior. J Am Chem Soc. Mar. 14, 2001;123(10):2460-1.
Lim et al., Development of a Safe Gene Delivery System Using Biodegradable Polymer, Poly[α-(4-aminobutyl)-l-glycolic acid].J Am Chem Soc. 2000;122:6524-25.
Lim et al., Self-assembled ternary complex of cationic dendrimer, cucurbituril, and DNA: noncovalent strategy in developing a gene delivery carrier. Bioconjug Chem. Nov.-Dec. 2002;13(6):1181-5.
Linhardt et al., Free-Radical Synthesis of Poly(2-ethylacrylic acid) Fractions of Low Polydispersity: Effects of Molecular Weight and Polydispersity on the pH-Dependent Conformational Transition in Aqueous Solutions. Macromolecules. 1999;32:4457-59.
Linhardt et al., pH-Induced Fusion and Lysis of Phosphatidylcholine Vesicles by the Hydrophobic Polyelectrolyte Poly(2-ethylacrylic Acid). Langmuir. 2000;16:122-27.
Liu et al., Poly(β-Amino Esters): Synthesis, Formulations, and Their Biomedical Applications. Adv Healthc Mater. Jan. 2019;8(2):e1801359. doi: 10.1002/adhm.201801359. Epub Dec. 14, 2018.

(56) References Cited

OTHER PUBLICATIONS

Liu et al., Three-dimensional photopatterning of hydrogels containing living cells. Biomedical Microdevices. 2002;4:257-266.
Loan et al., Oligoamidoamines and oligoesteramines based on antibiotics containing β-lactam ring. Euro Poly J. 1996;32:957-62.
Loan et al., Poly(amdio amine)s and poly(ester amine)s based on aromatic amines containg carboxyl groups. Macromolecular Chem and Phys. 1995;11:3525-33.
Luman et al., The convergent synthesis of poly(glycerol-succinic acid) dendritic macromolecules. Chemistry. Nov. 21, 2003;9(22):5618-26.
Luo et al., Synthetic DNA delivery systems. Nat Biotechnol. Jan. 2000;18(1):33-7.
Luten et al., Biodegradable Polymers as Non-viral Carriers for Plasmid DNA Delivery. J Control Release, 2008, 126, 97-110.
Lv et al., Toxicity of cationic lipids and cationic polymers in gene delivery. Journal of controlled release : official journal of the Controlled Release Society. 2006;114 ( 1 ), 100-9.
Lynn et al., Accelerated discovery of synthetic transfection vectors: parallel synthesis and screening of a degradable polymer library. J Am Chem Soc. Aug. 22, 2001;123(33):8155-6.
Lynn et al., Degradable Poly(β-amino esters): Synthesis, Characterization, and Self-Assembly with Plasmid DNA. J Am Chem Soc. Oct. 18, 2000;122(44):10761-8.
Lynn et al., pH-Responsive Polymer Microspheres: Rapid Release of Encapsulated Material within the Range of Intracellular pH. Angew Chem Int Ed Engl. May 4, 2001;40(9):1707-1710.
Mangraviti et al., Polymeric Nanoparticles for Nonviral Gene Therapy Extend Brain Tumor Survival in Vivo. ACS Nano, 2015, 9, 1236-1249.
Mann et al., Smooth muscle cell growth in photopolymerized hydrogels with cell adhesive and proteolytically degradable domains: synthetic ECM analogs for tissue engineering. Biomaterials. Nov. 2001;22(22):3045-51.
Maruo et al., Three-dimensional microfabrication with two-photon-absorbed photopolymerization. Opt Lett. Jan. 15, 1997;22(2):132-4.
Mathiowitz et al., Novel Mircocapsules for Delivery Sytems. Reactive Polymers. 1987;6:275-283.
Mathiowitz et al., Polyanhydride Microspheres as Drug Carriers. I. Hot-Melt Microencapsulation. J Control Rel. 1987;5:13-22.
Mathiowitz et al., Polyanhydride Microspheres as Drug Carriers. II. Microencapsulation by Solvent Removal. J Appl Polymer Sci. 1988;35:755-74.
Matsui et al., Messenger RNA-based Therapeutics for the Treatment of Apoptosis-associated Diseases. Scientific Reports 2015, 5.
McNamara et al., RNA-based Vaccines in Cancer Immunotherapy. Journal of Immunology Research, 2015, 2015.
Merdan et al., Prospects for cationic polymers in gene and oligonucleotide therapy against cancer. Adv Drug Deliv Rev. Sep. 13, 2002;54(5):715-58.
Midoux et al., Efficient gene transfer by histidylated polylysine/pDNA complexes. Bioconjug Chem. May-Jun, 1999;10(3):406-11.
Miller, Cationic Liposomes for Gene Therapy. Angew Chem Int Ed. 1998;37:1769-85.
Mirmira et al., Obesity, and Type 2 Diabetes Mellitus: Genuine Concern or Unnecessary Preoccupation? Translational Research, 2014, 164, 13-21.
Muh et al., Bismethacrylate-Based Hybrid Monomers via Michael-Addition Reactions. Macromolecules. 2001;34(17):5778-5785.
Mulligan, The basic science of gene therapy. Science. May 14, 1993;260(5110):926-32.
Murphy et al., A combinatorial approach to the discovery of efficient cationic peptoid reagents for gene delivery. Proc Natl Acad Sci U S A. Feb. 17, 1998;95(4):1517-22.
Narang et al., Cationic lipids with increased DNA binding affinity for nonviral gene transfer in dividing and nondividing cells. Bioconjug Chem. Jan.-Feb. 2005;16(1):156-68. doi: 10.1021/bc049818q.
Nguyen et al., Photopolymerizable hydrogels for tissue engineering applications. Biomaterials. Nov. 2002;23(22):4307-14.

O'Donnell et al., Preparation of microspheres by the solvent evaporation technique. Adv Drug Delivery Rev. 1997;28:25-42.
O'Hagan et al., Induction of potent immune responses by cationic microparticles with adsorbed human immunodeficiency virus DNA vaccines. J Virol. Oct. 2001;75(19):9037-43.
Odian et al., Step Polymerization. In: Principles of Polymerization. John Wiley & Sons, Inc. New York. 1991:73-89.
Ogris et al., Tumor-targeted gene therapy: strategies for the preparation of ligand-poly ethylene glycol-polyethylenimine/DNA complexes. J Control Release. Aug. 28, 2003;91(1-2):173-81.
Okada, One- and three-month release injectable microspheres of the LH-RH superagonist leuprorelin acetate. Adv Drug Deliv Rev. Oct. 13, 1997;28(1):43-70.
Pack et al., Design and development of polymers for gene delivery. Nat Rev Drug Discov. Jul. 2005;4(7):581-93.
Pack et al., Design of imidazole-containing endosomolytic biopolymers for gene delivery. Biotechnol Bioeng. Jan. 20, 2000;67(2):217-23.
Phillips et al., Enhanced antibody response to liposome-associated protein antigens: preferential stimulation of IgG2a/b production. Vaccine. 1992; 10(3):151-8.
Pollard et al., Challenges and Advances Towards the Rational Design of mRNA Vaccines. Trends in Molecular Medicine, 2013, 19, 705-713.
Prabha et al., Size-dependency of nanoparticle-mediated gene transfection: studies with fractionated nanoparticles. Int J Pharm. Sep. 5, 2002;244(1-2):105-15.
Putnam et al., Poly(4-hydroxy-l-proline ester): Low-Temperature Polycondensation and Plasmid DNA Complexation. Macromolecules 1999;32:3658-62.
Putnam et al., Polymer-based gene delivery with low cytotoxicity by a unique balance of side-chain termini. Proc Natl Acad Sci U S A. Jan. 30, 2001;98(3):1200-5. Epub Jan. 23, 2001.
Rao et al., Poly(butanediol Spermate): A Hydrolytically Labile Polyester-Based Nitric Oxide Carrier. J Bioactive Compatible Polymers. 1999;14:54-63.
Remy et al., Gene transfer with lipospermines and polyethylenimines. Adv Drug Deliv Rev. Mar. 2, 1998;30(1-3):85-95.
Roberts et al., Preliminary biological evaluation of polyamidoamine (PAMAM) Starburst dendrimers. J Biomed Mater Res. Jan. 1996;30(1):53-65.
Robinson et al., Nucleic acid immunizations. Curr. Protoc. Immunol. 2001, Chapter 2: Unit 2.14.
Ruoslahtl, The RGD story: a personal account. Matrix Biol. Nov. 2003;22(6):459-65.
Sahoo et al., Residual polyvinyl alcohol associated with poly (D,L-lactide-co-glycolide) nanoparticles affects their physical properties and cellular uptake. J Control Release. Jul. 18, 2002;82(1):105-14.
Sanford, The biolistic process. Trends Biotechnol. 1988;6:299-302.
Satta et al., *Drosophila* Metabolize 1,4-Butanediol into γ-Hydroxybutyric Acid in Vivo. European Journal of Pharmacology, 2003, 473, 149-152.
Schaffer et al., Vector unpacking as a potential barrier for receptor-mediated polyplex gene delivery. Biotechnol Bioeng. Mar. 5, 2000;67(5):598-606.
Schrom et al., Translation of Angiotensin-Converting Enzyme 2 upon Liver- and Lung-Targeted Delivery of Optimized Chemically Modified mRNA. Mol Ther Nucleic Acids. Jun. 16, 2017;7:350-365. doi: 10.1016/j.omtn.2017.04.006. Epub Apr. 13, 2017.
Schwartz et al., Peptide-mediated cellular delivery. Curr Opin Mol Ther. Apr. 2000;2(2):162-7.
Schweikl et al., Triethylene glycol dimethacrylate induces large deletions in the hprt gene of V79 cells. Mutat Res. Jan. 2, 1999;438(1):71-8.
Sergeeva et al., mRNA-based therapeutics—Advances and perspectives. Biochemistry (Moscow) 2016, 81, 709-722.
Shchori, Poly(secondary Amine)s from Diacrylates and Diamines. J Polym Sci Polymer. 1983;21:413-15.
Shmueli et al., Gene delivery nanoparticles specific for human microvasculature and macrovasculature. Nanomedicine. Oct. 2012;8(7):1200-7. doi: 10.1016/j.nano.2012.01.006. Epub Feb. 1, 2012.

(56) References Cited

OTHER PUBLICATIONS

Singh et al., Cationic microparticles: A potent delivery system for DNA vaccines. Proc Natl Acad Sci U S A. Jan. 18, 2000;97(2):811-6.
Smeds et al., Photocrosslinkable polysaccharides for in situ hydrogel formation. J Biomed Mater Res. Jan. 2001;54(1):115-21.
Somia et al., Gene therapy: trials and tribulations. Nat Rev Genet. Nov. 2000;1(2):91-9.
Strong et al., A General Synthetic Route to Defined, Biologically Active Multivalent Arrays. J Am Chem Soc. 1999;121:6193-96.
Suh et al., An angiogenic, endothelial-cell-targeted polymeric gene carrier. Mol Ther. Nov. 2002;6(5):664-72.
Sullivan et al., Development of a novel gene delivery scaffold utilizing colloidal gold-polyethylenimine conjugates for DNA condensation. Gene Therapy. 2003;10:1882-90.
Sunshine et al., Poly (β-amino ester)-nanoparticle Mediated Transfection of Retinal Pigment Epithelial Cells in Vitro and in Vivo. PloS one, 2012, 7, e37543.
Sunshine et al., Small-Molecule End-Groups of Linear Polymer Determin Cell-type Gene-Delivery Efficacy. Advanced Materials, 2009, 21, 4947-4951.
Tang et al., In vitro gene delivery by degraded polyamidoamine dendrimers. Bioconjug Chem. Nov.-Dec. 1996;7(6):703-14.
Thomas et al., Non-viral gene therapy: polycation-mediated DNA delivery. Appl Microbiol Biotechnol. Jul. 2003;62(1):27-34. Epub Apr. 29, 2003.
Tian et al., Biodegradable synthetic polymers: Preparation, functionalization and biomedical application. Prog Polym Sci. 2012;37(2):237-280.
Tosatti et al., RGD-containing peptide GCRGYGRGDSPG reduces enhancement of osteoblast differentiation by poly(L-lysine)-graft-poly(ethylene glycol)-coated titanium surfaces. J Biomed Mater Res A. Mar. 1, 2004;68(3):458-72.
Trubetskoy et al., Recharging cationic DNA complexes with highly charged polyanions for in vitro and in vivo gene delivery. Gene Ther. Feb. 2003;10(3):261-71.
Tweedie et al., Combinatorial material mechanics: high-throughput polymer synthesis and nanomechanical screening. Adv Mater. 2005;17:2599-2604.
Tzeng et al., Cystamine-terminated Poly (beta-amino ester)s for siRNA Delivery to Human Mesenchymal Stem Cells and Enhancement of Osteogenic Differentiation. Biomaterials, 2012, 33, 8142-8151.
Uhrich, Hyperbranched Polymers for Drug Discovery. Trends Polymer Sci. 1997;5:388-93.
Unal et al., Influence of filler addition on the mechanical properties of nylon-6 polymer. Journal of Reinforced Plastics and Composites. 2004;23(5):461-469.
Unkeless et al., Structure and function of human and murine receptors for IgG. Annu Rev Immunol. 1988;6:251-81.
Van De Wetering et al., Structure-activity relationships of water-soluble cationic methacrylate/methacrylamide polymers for nonviral gene delivery. Bioconjug Chem. Jul.-Aug. 1999;10(4):589-97.
Vu et al., Generation of a Focused Poly (amino ether) Library: Polymer-mediated Transgene Delivery and Gold-nanorod Based Theranostic Systems. Theranostics. 2012, 2, 1160-1173.
Vuorimaa et al., Poly(β-amino ester)-DNA complexes: time-resolved fluorescence and cellular transfection studies. J Control Release. Sep. 5, 2011;154(2):171-6. doi: 10.1016/j.jconrel.2011.06.016. Epub Jun. 15, 2011.
Vázquez et al., Construction of hydrolytically-degradable thin films via layer-by-layer deposition of degradable polyelectrolytes. J Am Chem Soc. Nov. 27, 2002;124(47):13992-3.
Wagner et al., Influenza virus hemagglutinin HA-2 N-terminal fusogenic peptides augment gene transfer by transferrin-polylysine-DNA complexes: toward a synthetic virus-like gene-transfer vehicle. Proc Natl Acad Sci U S A. Sep. 1, 1992;89(17):7934-8.
Walter et al., Microencapsulation of DNA using poly(DL-lactide-co-glycolide): stability issues and release characteristics. J Control Release. Sep. 20, 1999;61(3):361-74.
Wang et al., Mechanical and rheological properties of HDPE/graphite composite with enhanced thermal conductivity. Polymer Composites. 2001;22(1):97-103.
Wang et al., One-step Generation of Mice Carrying Mutations in Multiple Genes by CRISPR/Cas-mediated Genome Engineering. Cell, 2013, 153, 910-918.
Weiss et al., mRNA Vaccination as a Safe Approach for Specific Protection from Type I Allergy. Expert Review of Vaccines, 2012, 11, 55-67.
West et al., Photopolymerized hydrogel materials for drug delivery applications. Reactive Polymers. 1995; 25:139-147.
Whitehead et al., In vitro-in vivo translation of lipid nanoparticles for hepatocellular siRNA delivery. ACS Nano. Aug. 28, 2012;6(8):6922-9. doi:10.1021/nn301922x. Epub Jul. 6, 2012.
Wiethoff et al., Barriers to nonviral gene delivery. J Pharm Sci. Feb. 2003;92(2):203-17.
Wu et al., Cationic lipid polymerization as a novel approach for constructing new DNA delivery agents. Bioconjug Chem. Mar.-Apr. 2001;12(2):251-7. doi: 10.1021/bc000097e.
Yang et al., A new approach to identifying genotoxic carcinogens: p53 induction as an indicator of genotoxic damage. Carcinogenesis. Jun. 1998;19(6):1117-25.
Yin et al., Non-viral vectors for gene-based therapy. Nature Reviews Genetics 2014, 15 (8), 541-555.
Zauner et al., Polylysine-based transfection systems utilizing receptor-mediated delivery. Adv Drug Deliv Rev. Mar. 2, 1998;30(1-3):97-113.
Zhang et al., Structure/property relationships in erodible multilayered films: influence of polycation structure on erosion profiles and the release of anionic poly electrolytes. Langmuir. Jan. 3, 2006;22(1):239-45.
Zhao et al., Synthesis of Amphiphilic Poly (β-amino ester) for Efficiently Minicircle DNA Delivery in Vivo. ACS Applied Materials & Interfaces, 2016, 8, 19284-19290.
Zhou et al., Biodegradable poly( amine-co-ester) terpolymers for targeted gene delivery. Nature materials. 2011, 11 (1):82-90.
Zhou et al., Highly Branched Poly (β-amino ester)s for Skin Gene Therapy. Journal of Controlled Release, 2016, 244, 336-346.
Zhou et al., Preparation of Poly(l-serine ester): A Structural Analogue of Conventional Poly(l-serine). Macromolecules. 1990;23:3399-406.
Zhou et al., The transition from linear to highly branched poly(β-amino ester)s: Branching matters for gene delivery. Sci Adv. Jun. 17, 2016;2(6):e1600102. doi: 10.1126/sciadv.1600102.
Zhu et al., Synthesis of Star Poly (ε-caprolactone) Catalyzed by Lanthanum Tris (2,6-di-tert-butyl-4-methylphenolate). Chinese J Catalysis. Jun. 2007;28(6):547-50.
Zuber et al., Towards synthetic viruses. Adv Drug Deliv Rev. Nov. 19, 2001;52(3):245-53.
Anderson et al., Semi-automated synthesis and screening of a large library of degradable cationic polymers for gene delivery. Angew Chem Int Ed Engl. Jul. 14, 2003;42(27):3153-8.
Gao et al., Hyperbranched polymers: from synthesis to applications. Prog Polym Sci. Mar. 2004;29(3):183-275. doi: 10.1016/j.progpolymsci.2003.12.002.
Holter et al., Degree of branching in hyperbranched polymers. Acta Polymer 1997, 48, 30-35.
Kaczmarek et al., Polymer-Lipid Nanoparticles for Systemic Delivery of mRNA to the Lungs. Angew Chem Int Ed Engl. Oct. 24, 2016;55(44):13808-13812. doi:10.1002/anie.201608450. Epub Sep. 30, 2016.
Kamat et al., Poly(β-amino ester) nanoparticle delivery of TP53 has activity against small cell lung cancer in vitro and in vivo. Mol Cancer Ther. Apr. 2013;12(4):405-15. doi: 10.1158/1535-7163.MCT-12-0956. Epub Jan. 30, 2013.
Su et al., In vitro and in vivo mRNA delivery using lipid-enveloped pH-responsive polymer nanoparticles. Mol Pharm. Jun. 6, 2011;8(3):774-87. doi: 10.1021/mp100390w. Epub Apr. 1, 2011.
Wang et al., Synthesis and Gene Delivery of Poly(amido amine)s with Different Branched Architecture. Biomacromolecules 2010;11(2):489-495. DOI: 10.1021/bm901215s.

(56) References Cited

OTHER PUBLICATIONS

Wu et al., Effects of Chemistries of Trifunctional Amines on Mechanisms of Michael Addition Polymerizations with Diacrylates. Macromolecules, 2004;37(18):6763-6770. DOI: 10.1021/ma0493832.

Wu et al., Hyperbranched poly(amino ester)s with different terminal amine groups for DNA delivery. Biomacromolecules. Jun. 2006;7(6):1879-83.

Zhou et al., Development of Branched Poly(5-Amino-l-pentanol-co-1,4-butanediol Diacrylate) with High Gene Transfection Potency Across Diverse Cell Types. ACS Appl Mater Interfaces. Dec. 21, 2016;8(50):34218-34226. doi: 10.1021/acsami.6b12078. Epub Dec. 6, 2016.

Zugates et al., Rapid Optimization of Gene Delivery by Parallel End-modification of Poly(β-amino ester)s. Mol Ther. Jul. 2007;15(7):1306-1312. doi:10.1038/sj.mt.6300132. Epub Dec. 7, 2016.

| Polymer | Degree of Branching | Mw (Da) | PDI | Intrinsic Viscosity (dl/g) |
|---|---|---|---|---|
| Linear DD90-118 | 0.0 | 15138 | 1.90 | 0.0415 |
| hDD90-118 (0.1) | 0.1 | 15463 | 1.41 | 0.0295 |
| hDD90-118 (0.2) | 0.2 | 16425 | 1.28 | 0.0258 |
| hDD90-118 (0.3) | 0.3 | 23682 | 1.32 | 0.0159 |

POLY(BETA-AMINO ESTERS) AND USES THEREOF

RELATED APPLICATIONS

The present application is a division of U.S. application Ser. No. 16/170,318, filed Oct. 25, 2018, which claims priority under 35 U.S.C. § 119(e) to U.S. provisional application U.S. Ser. No. 62/578,139, filed Oct. 27, 2017, each of which is incorporated herein by reference.

BACKGROUND

Nucleic acid-based therapeutics hold the potential to treat any disease with a protein target. DNA has been used for the majority of gene therapy clinical trials. The use of mRNA instead of DNA would negate the risk of insertional mutagenesis and also confer the ability to transfect non-dividing cells which would be an advantage, particularly in respiratory epithelium which is slowly dividing or terminally differentiated. For example, the ability of in vitro transcribed (IVT)-mRNA to restore surfactant protein B expression has been demonstrated in the lung, albeit using invasive intratracheal delivery. The development of effective delivery systems for IVT-mRNA, and ways to address the immunogenicity and instability of IVT-mRNA, remain a critical hurdle for clinical adoption.

Branched polyethylenimine (bPEI) are known to be efficient delivery vectors for nebulized gene delivery. However, toxicity concerns related to bPEI remain, due to accumulation of the relatively large, non-degradable polymer. Lower molecular weight PEIs tend to have lower toxicity. However, DNA transfection efficiency is generally diminished with lower molecular weight PEIs, and those with molecular weights below approximately 1.8 kDa are ineffective. The immunogenicity and instability of IVT-mRNA also is an obstacle to its therapeutic potential. As such, there remains a need for effective, non-invasive vehicles for the delivery of therapeutic agents, such as nucleic acids. In particular, there remains a need for delivery vehicles that form stable compositions, suitable for the delivery of therapeutic agents, such as mRNA, via nebulization.

SUMMARY

The present disclosure relates to poly(beta amino esters) (PBAE) polymers useful for the non-viral delivery of agents (e.g., nucleic acids) to cells. The PBAE of Formula (I) and Formula (II), salts thereof, and embodiments described herein, are collectively referred to as "polymers of the invention." The polymers of Formula (I) are branched or hyperbranched. The polymers of Formula (II) are linear. The degree of branching can be used to optimize properties such as solubility, viscosity, and efficacy as a transfection reagent. Polymers of the invention can be used to prepare stable formulations (e.g., particles) for nebulization or aerosol delivery.

In one aspect, provided herein are poly(beta-amino esters) (PBAE) of Formula (I), comprising: a bis(propionyl) diradical of Formula (A), a diradical of Formula (B), a triradical of Formula (C), a radical of Formula (D), and optionally, a diradical of Formula (E):

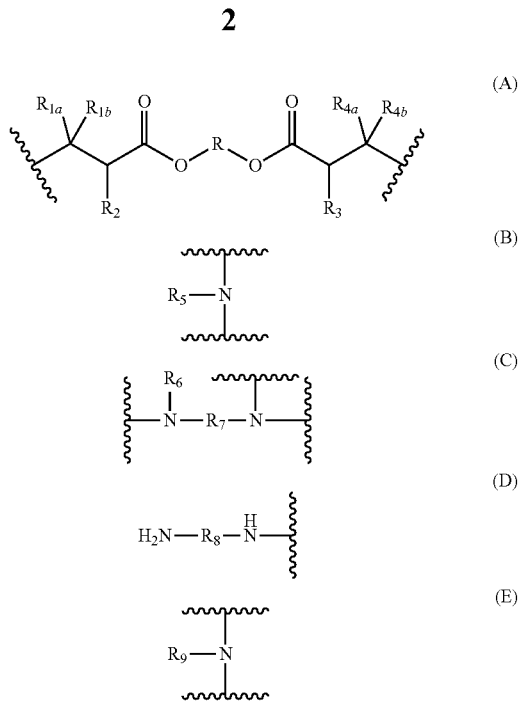

In another aspect, provided herein are compositions comprising a polymer of Formula (I) and an agent. In certain embodiments, the agent is a protein, peptide, polynucleotide, or small molecule.

In another aspect, provided herein are poly(beta-amino esters) (PBAE) of Formula (II), comprising: a bis(propionyl) diradical of Formula (A), a diradical of Formula (B), a radical of Formula (D), and optionally, a diradical of Formula (E).

Provided in other aspects are methods of delivering a polynucleotide to a cell by contacting the cell with a composition comprising a polymer of Formula (I) or Formula (II), and methods of treating a disease or disorder in a subject in need of such treatment by administering to the subject a pharmaceutical composition comprising a polymer of Formula (I) or Formula (II).

In another aspect, provided herein a method of preparing a polymer of Formula (I), comprising (i) combining a bis(acrylate) compound of Formula (A') with a compound of Formula (B'), a compound of Formula (C'), and optionally a compound of Formula (E'); and (ii) combining the product of (i) with a compound of Formula (D'):

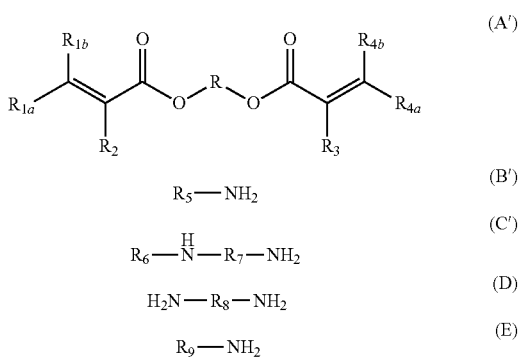

BRIEF DESCRIPTION OF THE DRAWINGS

FIG. 1A shows a subset of diacrylates, primary/bis-amines and end-cap amine monomers used to synthesize linear PBAEs. FIG. 1B shows a representative synthesis scheme. FIG. 1C shows transfection results for the following: A549 lung epithelial cells transfected with 50 ng of mRNA encoding for firefly luciferase and bioluminescence, assessed after 24 hours, normalized to cell viability (n=4, +S.D.). The highest luminescence was observed in cells that were transfected with a PBAE composed of monomers DD90-118. The effect of molecular weight, end cap amine, and addition of alkylamine C12 in vivo can be found in FIGS. 11 and 12B.

FIG. 2A shows the synthesis of hyperbranched DD90-118 PBAEs (hDD90-118) via the addition of a tri-functional amine (BB'2) to DD90 followed by end-capping with monomer 118. FIG. 2B shows that the transfection efficiency of hyperbranched PBAEs in A549 lung epithelial cell line was assessed by measuring bioluminescence 24 hours after delivery of mRNA encoding for firefly luciferase normalized to cell viability (n=3, +S.D.). The hPBAEs of FIG. 2B were prepared according to Example 2.

FIG. 3A shows particle stability at various pHs. Hyperbranched PBAE hDD90-118 (0.3) and linear DD90-118 both begin to aggregate as pH increases. Nanoparticles composed of the linear PBAE begin to increase in size at pH 7.5 and aggregates above pH 8, whereas nanoparticles of the hyperbranched PBAE are stable with respect to particle diameter until pH 8.5 and aggregate above pH 9. FIG. 3B shows that this loss of particle stability in FIG. 3A correlates to a reduction in zeta potential below +30 mV with increasing pH. FIG. 3C is dynamic light scattering of DD90-118 or C32-118 based polymers complexed with mRNA (50 to 1) at two concentrations; 'high' 0.5 mg/mL mRNA (dashed lines) and low' 0.003 mg/mL mRNA (solid lines). At pH 7.4, linear PBAEs formulated with mRNA at 0.5 mg/mL (grey dashed line) become unstable and aggregate into large particles whereas hyperbranched analogues (black dashed line) remain stable nanoparticles below 200 nm. Both linear and branched PBAEs at a mRNA concentration of 0.003 mg/mL remain stable (grey and black solid lines, respectively).

FIG. 4A depicts a schematic of the vibrating mesh nebulizer and whole body chamber used for aerosol delivery of mRNA encoding firefly luciferase. As shown in FIG. 4B, radiance was measured and protein quantified in the lungs of C57BL/6 mice 24 hours after nebulization of 0.5 mg/mL of mRNA n=3-6. FIG. 4C shows that uniform distribution of radiance was observed across 5 lobes of the lung treated with hDD90-118. FIG. 4D shows that bioluminescence was localized to the lung with no radiance detected in other major organs. As shown in FIG. 4E, hDD90-118 nanoparticles can be repeatedly administered via nebulization (green arrows) and facilitates repeated production of luciferase protein in the lung. There was no significant weight loss or inflammation after repeated inhaled delivery of hDD90-118 nanoparticles (FIG. 4F and FIG. 4G) in any of the treatment groups. Flow cytometry analysis of the lung found that the epithelial cell population was the majority cell sub-type transfected by hDD90-118 nanoparticles after nebulization of mRNA encoding for Cre-recombinase to Ai14 tdTomato reporter mice (+S.D, n=3), FIG. 4H.

FIG. 5A shows intravenous delivery of mRNA (0.5 mg/kg) encoding for firefly luciferase via tail vein injection leads to bioluminence in the lungs and spleen. FIG. 5B shows that highest radiance is observed in the lungs of mice transfected with hDD90-118 with DB 0.3 (hPBAE) nanoparticles (*p<0.05), (medians±IQR, n=4), toxicity as assessed by weight loss is significantly lower in hPBAE compared to the linear analogue shown in FIG. 5C. Statistical analysis using one-way Anova with Tukeys test (+S.D, n=4). FIG. 5D and FIG. 5E shows flow cytometry of lung cells after intravenous injection, lung endothelial cells are the majority sub-type transfected by hDD90-118 (hPBAE) and branched polyethenylenimine 25 kDa (bPEI). (n=3, +S.D).

FIG. 6A shows the relative amount of acrylate (DD) and backbone amine (90) as determined using peaks in $^1$H NMR spectra at 7.09 ppm 'a' and 3.49 ppm 'c' respectively. Branching amine was determined using peak at 2.17 ppm (D) and terminal end-cap amine (118) determined using peak at 0.89 ppm (E). FIG. 6B shows the molar ratio of these monomers in PBAE as determined by $^1$H NMR; as the degree of branching increases, the ratio of end cap amine to acrylate also increases. FIG. 6C shows the degree of branching (DB), which was calculated according to the equation $DB=(D+T)/(D+T+L)*$ where D is the number of dendritic units (e.g., branching amine of Formula (C)), T is terminal units (118), and L is linear units (DD and 90). Theoretical values calculated from feed ratios during reaction are compared to values determined experimentally by $^1$H NMR and show good agreement. Hyperbranched DD90-118 with varying degrees of branching were synthesized by changing feed ratio of monomer 90 to monomer BB2'. (*Hawker & Fretchet 1991 J. Am. Chem. Soc. 113(12)).

FIG. 7A shows triple detection gel permeation chromatography (GPC), example chromatograms for hDD90-118 (0.2). FIG. 7B shows molecular weight (Mw) and intrinsic viscosity determined by GPC. As branching of the polymer increases, viscosity is reduced.

FIG. 9A shows a calibration curve, which demonstrates a linear relationship between polymer concentration and absorbance at 250 nm. In FIG. 9B, serial dilutions of a supersaturated solution were filtered and absorbance measured at 250 nm. The average original concentration of diluted samples was calculated and found to be greater for hyperbranched PBAE compared to linear (n=3, +S.D.).

DETAILED DESCRIPTION

Figure 1A:
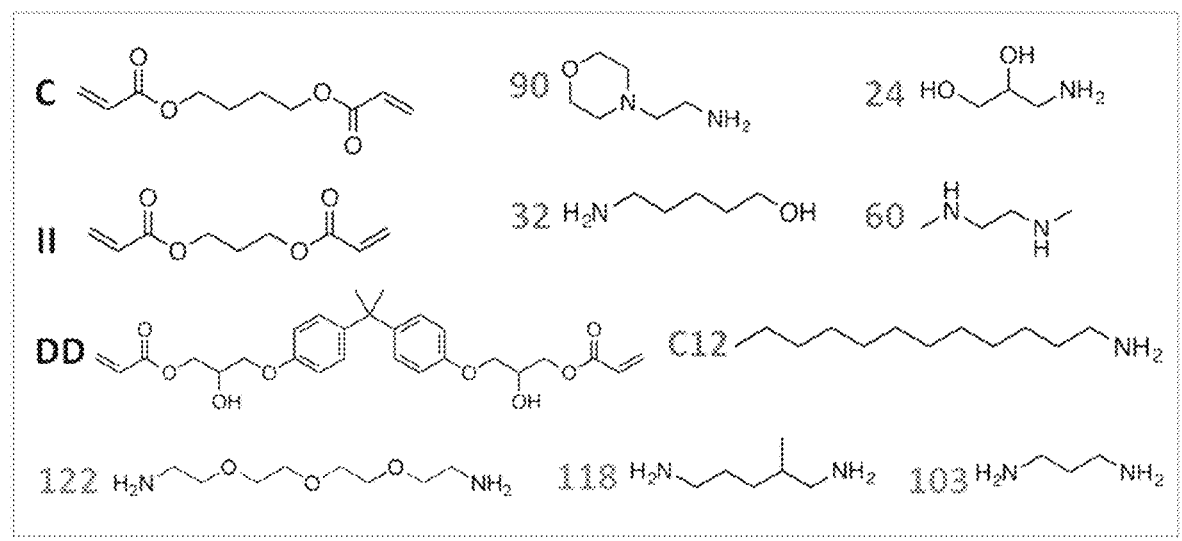
FIGS. 1A-1C.

The present disclosure relates to inventive poly(beta amino esters) (PBAE), which useful for the non-viral delivery of agents (e.g., nucleic acids) to cells. In certain embodiments, polymers of the invention are useful for the delivery of mRNA to both lung endothelium and epithelium via nebulization, dry powder inhalation or systemic administration and therefore are clinically relevant to the treatment of disorders of the lung epithelium, including enzyme deficiencies and cystic fibrosis.

Polymers of Formula (I)

In one aspect, provided herein is a poly(beta-amino ester) (PBAE) polymer of Formula (I) comprising:

a. a bis(propionyl) diradical of Formula (A):

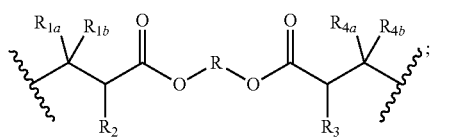

(A)

b. a diradical of Formula (B):

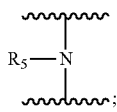

(B)

c. a triradical of Formula (C):

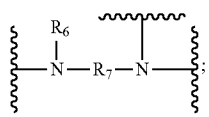

(C)

d. a radical of Formula (D):

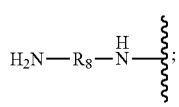

(D)

and optionally e. a diradical of Formula (E):

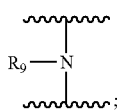

(E)

wherein:

R is optionally substituted aliphatic, optionally substituted heteroaliphatic, optionally substituted carbocyclyl, optionally substituted heterocyclyl, optionally substituted arylene, optionally substituted heteroarylene, or a combination thereof;

$R_{1a}$, $R_{1b}$, $R_2$, $R_3$, $R_{4a}$, and $R_{4b}$ are each independently hydrogen, halogen, hydroxyl, alkoxyl, cyano, optionally substituted aliphatic, or optionally substituted heteroaliphatic;

$R_5$ is optionally substituted aliphatic, optionally substituted heteroaliphatic, optionally substituted carbocyclyl, optionally substituted heterocyclyl, optionally substituted optionally substituted aryl, or optionally substituted heteroaryl;

$R_6$ is optionally substituted aliphatic, optionally substituted heteroaliphatic, optionally substituted carbocyclyl, optionally substituted heterocyclyl, optionally substituted optionally substituted aryl, or optionally substituted heteroaryl;

$R_7$ is optionally substituted aliphatic, optionally substituted heteroaliphatic, optionally substituted carbocyclylene, optionally substituted heterocyclylene, optionally substituted optionally substituted arylene, or optionally substituted heteroarylene;

$R_8$ is optionally substituted aliphatic, optionally substituted heteroaliphatic, optionally substituted carbocyclylene, optionally substituted heterocyclylene, optionally substituted optionally substituted arylene, or optionally substituted heteroarylene; and $R_9$ is optionally substituted aliphatic;

wherein:

each Formula (A) has two points of attachment to radicals selected from Formulae (B), (C), (D), and optionally (E);

each Formula (B) has two points of attachment to radicals of Formula (A);

each Formula (C) has three points of attachment to radicals of Formula (A);

each Formula (D) has one point of attachment to a radical of Formula (A); and each Formula (E), if present, has two points of attachment to radicals of Formula (A);

and wherein Formulae (B), (C), (D), and (E), if present, are different from one another.

The polymer of Formula (I) comprises radicals of Formulae (A), (B), (C), (D) and optionally (E) in various orders, arrangements, and molar percentages. By varying the molar percentages of one or more of the component radicals, it is possible to control the degree of branching, relative abundance of primary amines (e.g., primary amine termini) and thereby to control properties such as aqueous solubility and transfection efficiency.

In certain embodiments, the polymer of Formula (I) comprises a radical (i.e., a mono-radical or poly-radical) selected from the radicals of Table 1, and combinations thereof:

TABLE 1

| | |
|---|---|
| (1) | —A—B—A— |
| (2) | —A—B—A—B—A— |
| (3) | —A—C—A—B—A—<br>        |<br>     A—B—A— |
| (4) | —A—E—A— |
| (5) | —A—E—A—B—A— |
| (6) | —A—E—A—C—A—<br>           |<br>           A— |

TABLE 1-continued

| | |
|---|---|
| (7) | —A—E—A—C—A—B—A—<br>                           \|<br>                         A—B—A— |
| (8) | —A—E—A—C—A—E—A—<br>                           \|<br>                         A—B—A— |
| (9) | —A—C—<br>     \| |
| (10) | D—A—B—A— |
| (11) | D—A—B—A—B—A— |
| (12) | D—A—C—A—B—A—<br>         \|<br>        A—B—A— |
| (13) | D—A—E—A— |
| (14) | D—A—E—A—B—A— |
| (15) | D—A—E—A—C—A—<br>                \|<br>                A— |
| (16) | D—A—E—A—C—A—B—A—<br>                \|<br>                A—B—A— |
| (17) | D—A—E—A—C—A—E—A—<br>                \|<br>                A—B—A— |
| (18) | D—A—C—<br>        \| |

For example, radical (18) consists of radicals of Formulae (D), (A), and (C) in the indicated arrangement. Radical (18) may also be represented by the following formulae:

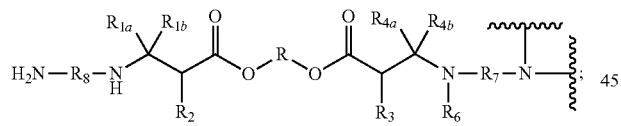

and

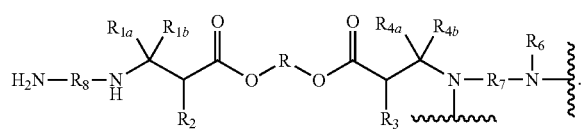

In certain embodiments, the polymer of Formula (I) comprises radicals of Formulae (A) and (B) in a molar ratio of about 1:0.5 to about 1:1. In certain embodiments, the polymer of Formula (I) comprises radicals of Formulae (A) and (C) in a molar ratio of about 1:0 to about 1:0.2. In certain embodiments, the polymer of Formula (I) comprises radicals of Formulae (A) and (D) in a molar ratio of about 1:0.5 to about 1:0.4. In certain embodiments, the polymer of Formula (I) comprises radicals of Formulae (A), (B), (C) and (D) in a molar ratio of about 1:0.5:0.2:0.39; 1:0.67:0.13: 0.27; 1:0.8:0.08:0.16; or 1:0.94:0:0.07. In certain embodiments, the polymer of Formula (I) comprises radicals of Formulae (A), (B), (C), (D) and (E) in a molar ratio of about 1:0.35:0.2:0.39:0.15; 1:0.47:0.13:0.27:0.2; 1:0.56:0.08: 0.16:0.24; or 1:0.66:0:0.07:0.28.

In certain embodiments, the polymer of Formula (II) comprises a linear radical selected from Table 1.

Polymers of Formula (II)

In another aspect, provided herein is a poly(beta-amino ester) (PBAE) polymer of Formula (II) comprising:

a. a bis(propionyl) diradical of Formula (A):

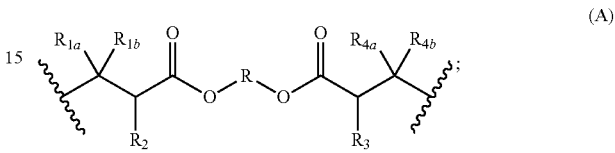

b. a diradical of Formula (B):

c. a radical of Formula (D):

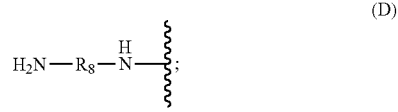

and optionally d. a diradical of Formula (E):

wherein:

R is optionally substituted aliphatic, optionally substituted heteroaliphatic, optionally substituted carbocyclyl, optionally substituted heterocyclyl, optionally substituted optionally substituted arylene, optionally substituted heteroarylene, or a combination thereof;

$R_{1a}$, $R_{1b}$, $R_2$, $R_3$, $R_{4a}$, and $R_{4b}$ are each independently hydrogen, halogen, hydroxyl, alkoxyl, cyano, optionally substituted aliphatic, or optionally substituted heteroaliphatic;

$R_5$ is optionally substituted aliphatic, optionally substituted heteroaliphatic, optionally substituted carbocyclyl, optionally substituted heterocyclyl, optionally substituted optionally substituted aryl, or optionally substituted heteroaryl;

$R_8$ is optionally substituted aliphatic, optionally substituted heteroaliphatic, optionally substituted carbocyclylene, optionally substituted heterocyclylene, optionally substituted optionally substituted arylene, or optionally substituted heteroarylene; and $R_9$ is optionally substituted aliphatic;

wherein:

each Formula (A) has two points of attachment to radicals selected from Formulae (B), (D), and optionally (E);

each Formula (B) has two points of attachment to radicals of Formula (A);

each Formula (D) has one point of attachment to a radical of Formula (A); and each Formula (E), if present, has two points of attachment to radicals of Formula (A);

and wherein Formulae (B), (D), and (E), if present, are different from one another.

In certain embodiments, Formulae (A), (B), (D) and (E) are as defined herein.

In certain embodiments, the polymer of Formula (II) comprises radicals of Formulae (A) and (B) in a molar ratio of about 1:0.5 to about 1:1. In certain embodiments, the polymer of Formula (II) comprises radicals of Formulae (A) and (D) in a molar ratio of about 1:0.5 to about 1:0.4. In certain embodiments, the polymer of Formula (II) comprises radicals of Formulae (A), (B), and (D) in a molar ratio of about 1:0.5:0.625 to 1:1:0.125. In certain embodiments, the polymer of Formula (II) comprises radicals of Formulae (A), (B), (D) and (E) in a molar ratio of about 1:0.35:0.625:0.15: to 1:0.7:0.125:0.3.

Molecular Weight

Molecular weight is influenced by the molar ratio of diacrylate monomer corresponding to the diradical of Formula (A) to the amine monomers corresponding to Formulae (B) and optionally (E). A higher molar ratio of diacrylate monomer amine monomer will lead to lower molecular weight. A diacrylate:amine molar ratio of about 1 will lead to greater molecular weight.

In certain embodiments, the polymers of the invention have a molecular weight in the range of 1-100 kDa, 5-50 kDa, 10-40 kDa, or 15-30 kDa. In certain embodiments, the polymers of the invention have a molecular weight in the range of 15-24 kDa. In certain particular embodiments, the polymers of the invention have a molecular weight of about 15 kDa, about 16 kDa, about 17 kDa, about 18 kDa, about 19 kDa, about 20 kDa, about 21 kDa, about 22 kDa, about 23 kDa, or about 24 kDa.

Branching

As used herein, the term "branched" refers to polymers containing branches that are composed of the same units that make up the linear portion of the main chain. As used herein, the term "hyperbranched" refers to polymers containing branches that are composed of the units that make up the linear portion of the main chain as well as further branch points (e.g., radicals of Formula (C), also referred to as "dendritic units"). Hyperbranched dendritic polymers contain randomly distributed dendritic units and offer a large chemical space for investigation as they can be synthesized with a wide range of monomers using one-pot reaction conditions. Linear segments can be combined with hyperbranched segments to alter the degree of branching (DB), thereby altering properties such as solubility, viscosity, and efficacy as a transfection reagent.

The terms "Degree of branching" and "DB" can be defined as the ratio of dendritic units (radicals of Formula (C)) to linear units (radicals of Formulae (A), (B), (D), and optionally (E)). DB can be calculated using the equation: DB=(D+T)/(D+T+L), where D is number of dendritic units, T is the number of terminal units (radical of Formula (D)) and L is number of linear units (radicals of Formulae (A), (B), and optionally (E)). (See also, Hawker & Fretchet 1991 J. Am. Chem. Soc. 113(12)). DB can be controlled as a function of the stoichiometry of Formula (B) to Formula (C). For example, higher DB is obtained by using a molar excess of the monomer corresponding to Formula (B), relative to the monomer corresponding to Formula (C). Linear polymers (DB=0) are obtained by omitting the monomer corresponding to Formula (C).

DB also correlates directly with an increase in terminal primary amine groups. Increased density of primary amines in the PBAE may influence polymer efficacy as a transfection reagent at various stages during the formulation and transfection process, for example, during nanoparticle formulation when the cationic polymer protects nucleic acid cargo through electrostatic condensation to prevent degradation by nucleases.

During endocytosis of the nanoparticle, increased amine density also increases the capacity of the polymer to become protonated, contributing to the "proton sponge" mechanism that has been proposed to trigger endosomal disruption, and subsequent escape into the cytoplasm, critical for translation of mRNA.

In certain embodiments, the polymers of the invention are linear. In certain embodiments, the polymers of the invention are branched or hyperbranched. DB influences properties such as intrinsic viscosity, solubility, and transfection efficacy. In certain embodiments, the polymer of Formula (I) has a degree of branching (DB) in the range of 0.0-1.0. In certain embodiments, the polymer of Formula (I) has a degree of branching (DB) in the range of 0.0-0.5. In certain particular embodiments, the DB of a polymer of Formula (I) is 0.0, about 0.1, about 0.2, about 0.3, about 0.4, about 0.5, about 0.6, or about 0.7.

In certain embodiments, the polymers of the invention are soluble in an aqueous solution. The aqueous solvent may comprise of 50-100% water by volume. In a particular embodiment, the aqueous solvent comprises at least 90%, at least 92%, at least 94%, at least 96%, at least 98% or at least 99% water by volume. In certain embodiments, the pH of the aqueous solvent is in the range of about 5 to about 7.5 (e.g., about 5.2 to about 7.4). In certain embodiments, the temperature of the aqueous solution is in the range of about 25° C. to about 37° C. An aqueous solution may further comprise an organic solvent such as dimethylsulfoxide, dimethylformamide, acetic acid, or an alcohol (e.g., methanol, ethanol or isopropanol).

In certain embodiments, the polymers of the invention have a solubility in aqueous solution of at least about 30, at least about 10, at least about 5, at least about 2, or at least about 1 mg/mL. In certain particular embodiments, the polymer has a solubility in an aqueous solution of at least about 1.6 mg/mL at about pH 7.4.

In certain embodiments, the polymers of the invention are biodegradable or biocompatible. As used herein, "biodegradable" polymers are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably do not induce inflammation or other adverse effects in vivo. In certain embodiments, the chemical reactions relied upon to break down the biodegradable polymers are uncatalyzed. Biodegradability is a particular advantage of these PBAE delivery vectors, particularly for repeat administration where non-degradable vectors like PEI may accumulate or be difficult for the body to metabolize. The term "biocompatible," as used herein, is intended to describe compounds that are not toxic to cells. Polymers are "biocompatible" if their addition to cells in vitro results in less than or equal to 20% cell death, and their administration in vivo does not induce inflammation or other such adverse effects.

Formula (A)

Formula (A) is a bis(propionyl) diradical, having two points of attachment to radicals selected from Formulae (B), (C), (D), and optionally (E).

In certain embodiments, Formula (A) is:

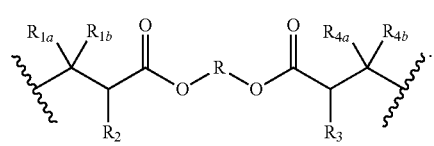
(A)

In certain embodiments, Formula (A) is of Formula (A1), (A2), (A3) or (A4):

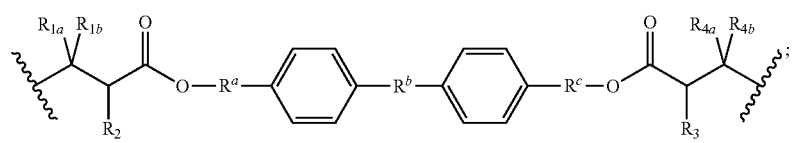
(A1)

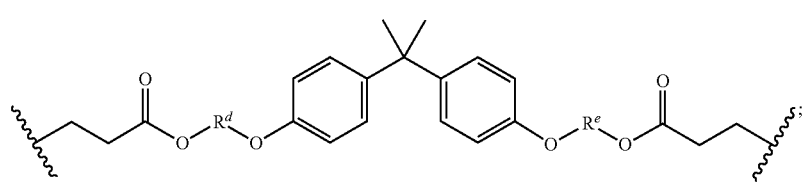
(A2)

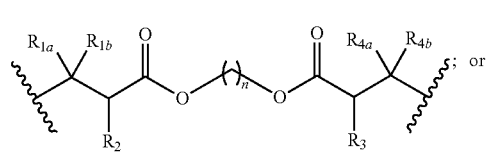
(A3)

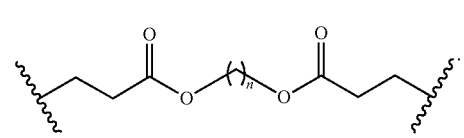
(A4)

In certain embodiments, R is optionally substituted aliphatic, optionally substituted heteroaliphatic, optionally substituted carbocyclylene, optionally substituted heterocyclylene, optionally substituted arylene, optionally substituted heteroarylene, or a combination thereof.

In certain embodiments, R is substituted aliphatic, unsubstituted aliphatic, substituted heteroaliphatic, unsubstituted heteroaliphatic, substituted arylene, unsubstituted arylene, substituted heteroarylene, unsubstituted heteroarylene or a combination thereof.

In certain embodiments, R is selected from carbon chains of 1 to 30 carbon atoms, heteroatom-containing carbon chains of 1 to 30 atoms, and carbon chains and heteroatom-containing carbon chains with at least one substituent selected from the group consisting of branched and unbranched alkyl, branched and unbranched alkenyl, branched and unbranched alkynyl, amino, alkylamino, dialkylamino, trialkylamino, ureido, cycloalkyl, heterocyclyl, aryl, heteroaryl, halogen, hydroxyl, alkoxy, cyano, amido, carbamoyl, carbonyl, carbonyldioxyl, alkylthioether, and thiol groups.

In certain embodiments, $R_{1a}$, $R_{1b}$, $R_2$, $R_3$, $R_{4a}$, and $R_{4b}$ are each independently hydrogen, halogen, hydroxyl, alkoxyl, cyano, optionally substituted aliphatic, or optionally substituted heteroaliphatic.

In certain embodiments, $R_{1a}$, $R_{1b}$, $R_2$, $R_3$, $R_{4a}$, and $R_{4b}$ are independently selected from the group consisting of hydrogen, alkyl, alkenyl, alkynyl, halogen, hydroxyl, alkoxyl, carbamoyl, carbonyldioxyl, amido, thiohydroxyl, alkylthioether, amino, alkylamino, dialkylamino, trialkylamino, cyano, and ureido, each of which may be substituted, as permitted by valency, with at least one substituent selected from the group consisting of alkyl, alkenyl, alkynyl, amino, alkylamino, dialkylamino, trialkylamino, aryl, ureido, cycloalkyl, heterocyclyl, aryl, heteroaryl, halogen, hydroxyl, alkoxy, cyano, amido, carbamoyl, carbonyl, carbonyldioxyl, alkylthioether, and thiol groups.

In certain embodiments, $R^a$, $R^b$, $R^c$, $R^d$, and Re are independently selected from optionally substituted $C_{1-6}$ alkyl, optionally substituted $C_{3-7}$ cycloalkyl, optionally substituted $C_{2-6}$ alkenyl, optionally substituted $C_{1-6}$ heteroalkyl, optionally substituted $C_{2-6}$ heterocyclyl, optionally substituted $C_{6-10}$ aryl, or optionally substituted $C_{2-6}$ heteroaryl.

In certain embodiments, n is 2-10. In certain particular embodiments, n is 2, 3, 4, 5, 6, 7, 8, 9 or 10.

In certain embodiments of Formulae (A), (A1), and (A3), $R_{1a}$ and $R_{4a}$ each are hydrogen. In certain embodiments, $R_{1a}$, $R_{1b}$, $R_{4a}$ and $R_{4b}$ each are hydrogen. In certain embodiments of Formulae (A), (A1), and (A3), $R_2$ and $R_3$ each are hydrogen. In certain embodiments, $R_{1a}$, $R_{1b}$, $R_2$, $R_3$, $R_{4a}$ and $R_{4b}$ are all hydrogen.

In certain particular embodiments, Formula (A) has the structure:

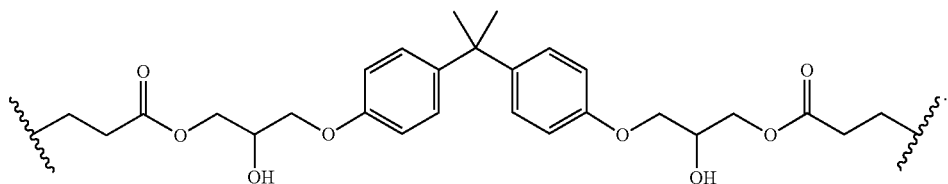 [SMILES: *CCC(=O)OCC(O)COc1ccc(C(C)(C)c2ccc(OCC(O)COC(=O)CC*)cc2)cc1]

In certain particular embodiments, Formula (A) has the structure:

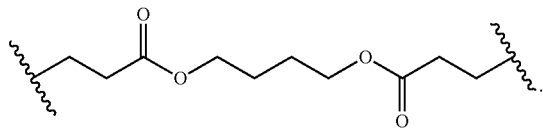 [SMILES: *CCC(=O)OCCCCOC(=O)CC*]

In certain embodiments, the polymers of the invention (e.g., a polymer of Formula (I) or (II)) comprise about 30-60 mol % Formula (A). In certain embodiments, the polymers of the invention comprise about 20-50 mol % Formula (A). In certain embodiments, the polymers of the invention comprise about 44-48 mol % Formula (A). In certain particular embodiments, the polymers of the invention comprise 44, 45, 46, 47 or 48 mol % Formula (A).

In certain embodiments, all radicals of Formula (A) are the same. In other embodiments, there are two or more (e.g., 2, 3 or 4) different radicals of Formula (A).

Formula (B)

Formula (B) is a diradical having two points of attachment to radicals of Formula (A). Typically Formula (B) joins to two different Formula (A) moieties.

In certain embodiments, Formula (B) is:

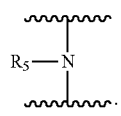

(B)

In certain embodiments, Formula (B) is of Formula (B1), (B2) or (B3):

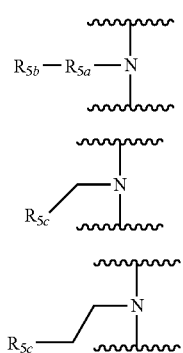

In certain embodiments, $R_5$ is optionally substituted aliphatic, optionally substituted heteroaliphatic, optionally substituted carbocyclyl, optionally substituted heterocyclyl, optionally substituted optionally substituted aryl, or optionally substituted heteroaryl.

In certain embodiments, $R_5$ is alkyl, alkenyl, alkynyl, halogen, hydroxyl, alkoxy, carbamoyl, carbonyldioxyl, amido, thiohydroxyl, alkylthioether, amino, alkylamino, dialkylamino, trialkylamino, cyano, ureido, cycloalkyl, heterocyclyl, aryl, and heteroaryl groups, each of which may be substituted with at least one substituent selected from the group consisting of alkyl, alkenyl, alkynyl, amino, alkylamino, dialkylamino, trialkylamino, aryl, ureido, cycloalkyl, heterocyclyl, aryl, heteroaryl, halogen, hydroxyl, alkoxy, cyano, amido, carbamoyl, carbonyl, carbonyldioxyl, alkylthioether, and thiol groups.

In certain embodiments, $R_{5a}$ is optionally substituted alkylene, or optionally substituted heteroalkylene.

In certain embodiments, $R_{5b}$ is absent, or is optionally substituted $C_{3-7}$ cycloalkyl, optionally substituted $C_{1-6}$ heteroalkyl, optionally substituted $C_{2-6}$ heterocyclyl, optionally substituted $C_{6-10}$ aryl, or optionally substituted $C_{2-6}$ heteroaryl.

In certain embodiments, $R_{5c}$ is optionally substituted $C_{3-7}$ cycloalkyl, or optionally substituted $C_{2-6}$ heterocyclyl.

In certain embodiments, Formula (B) is selected from the following:

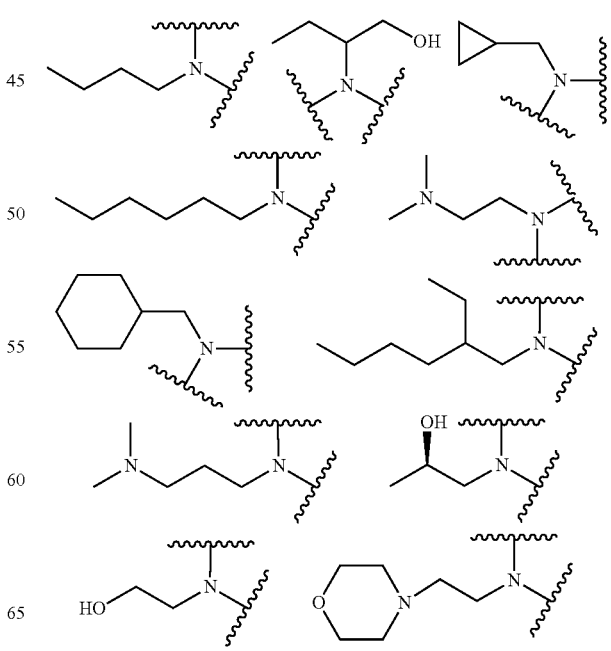

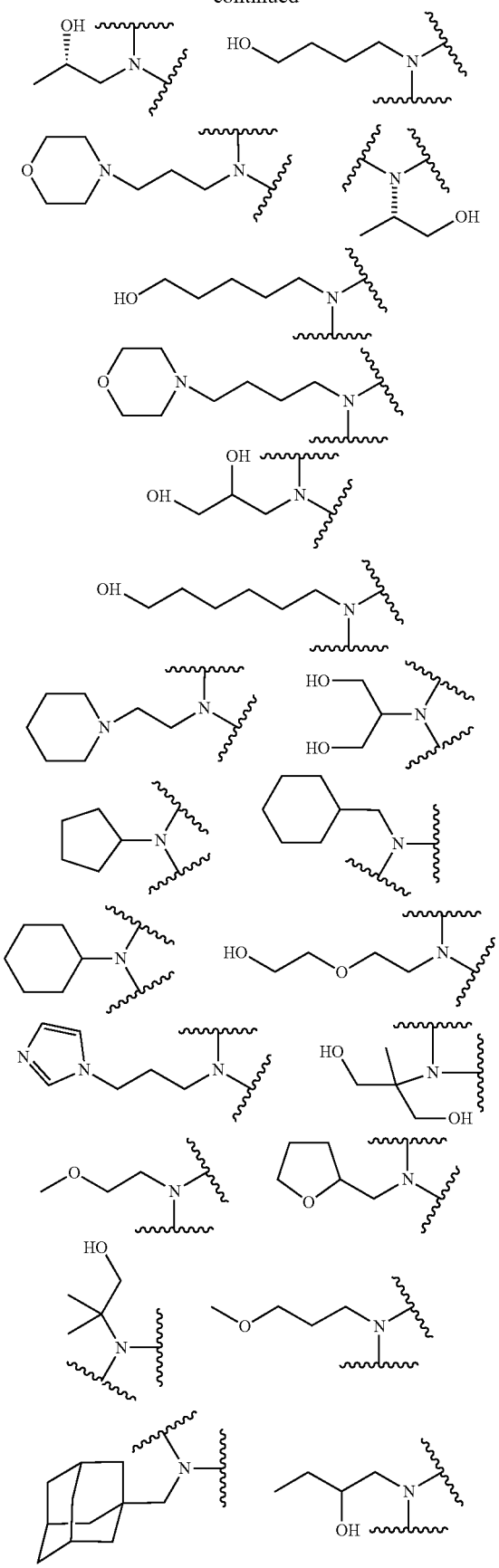
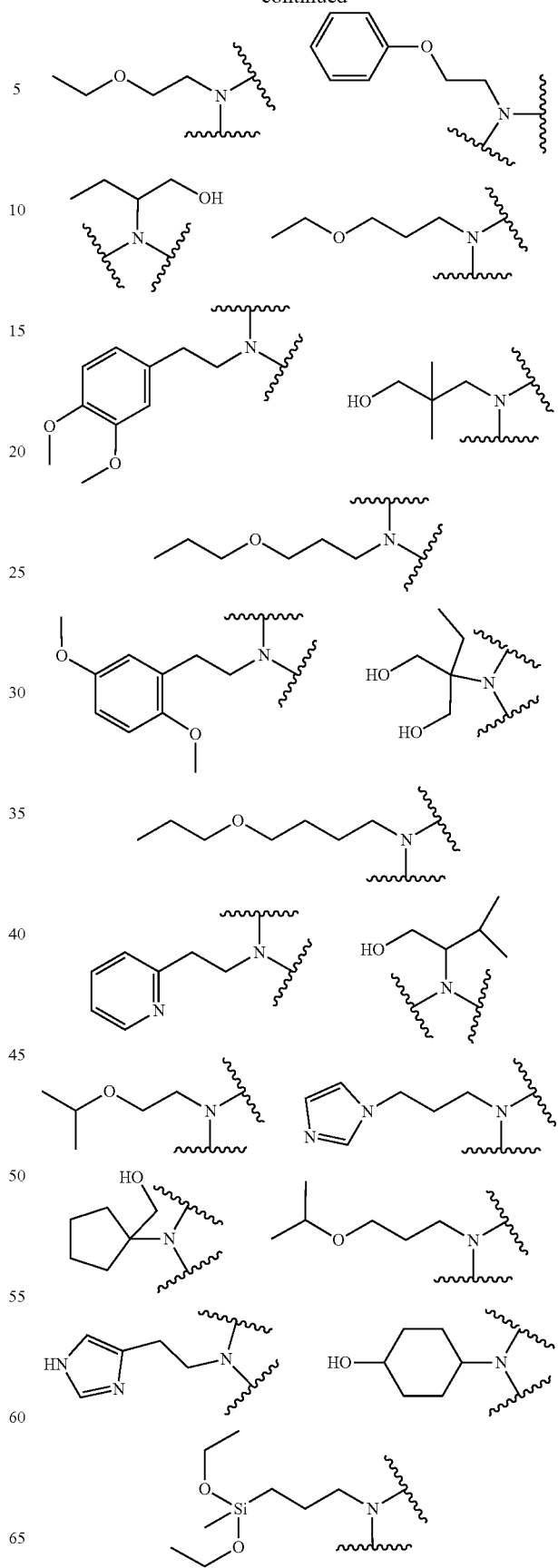

-continued
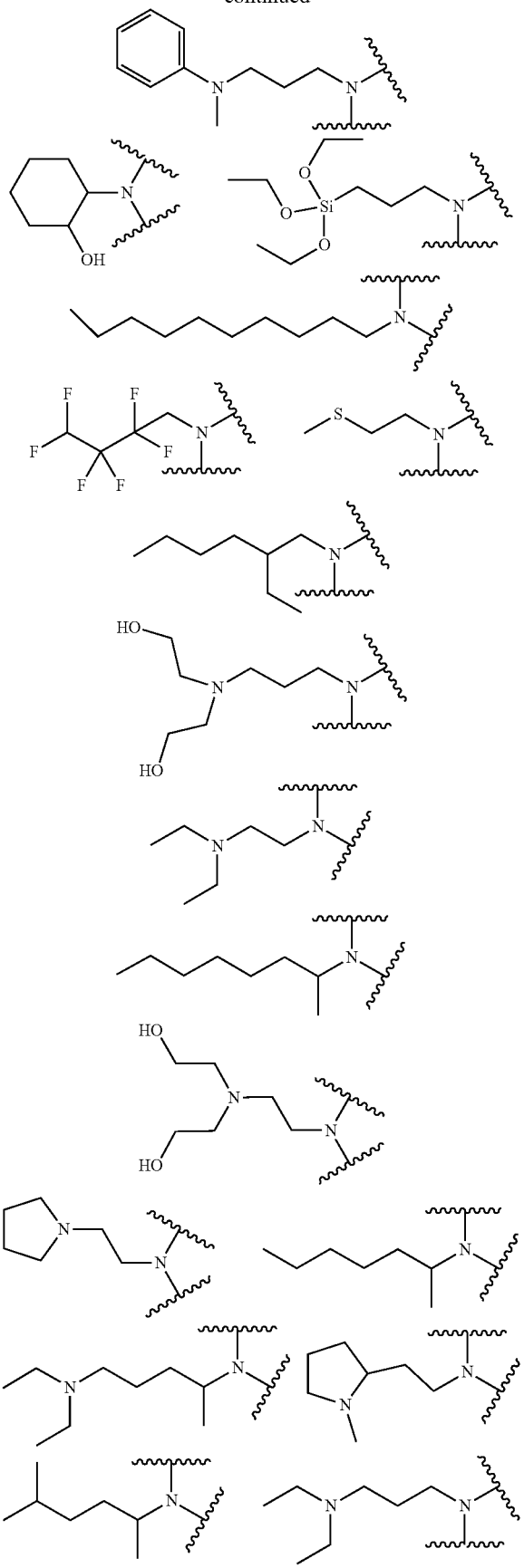
-continued
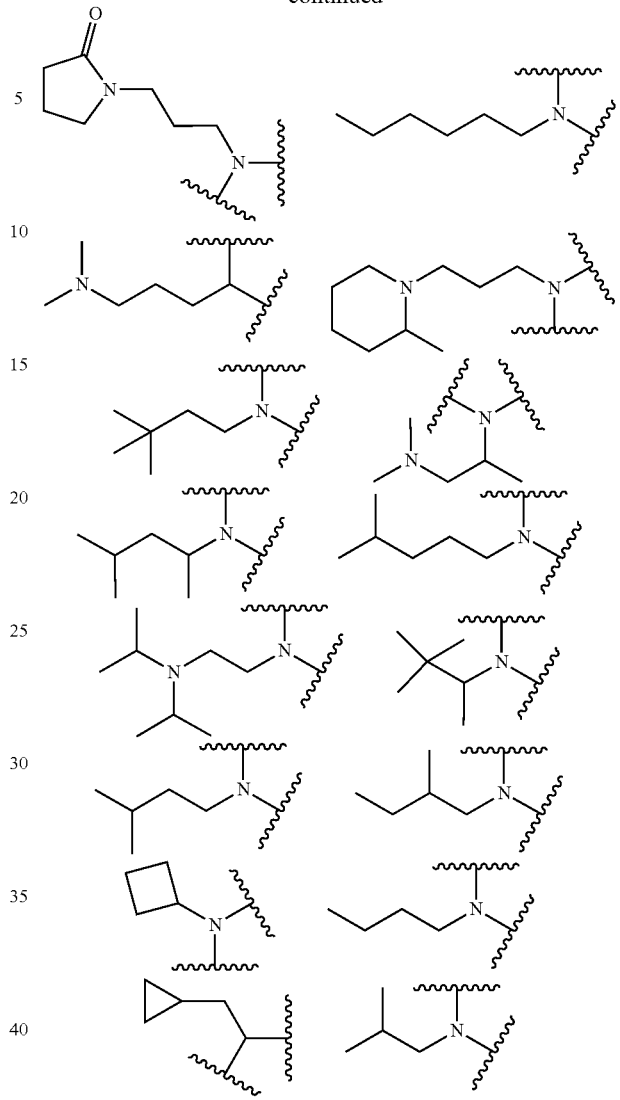
In certain particular embodiments, Formula (B) has the structure:
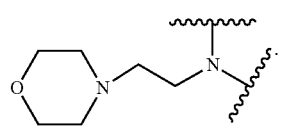 [SMILES: *N(*)CCN1CCOCC1]
In certain particular embodiments, Formula (B) has the structure:
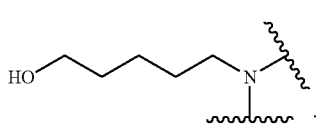 [SMILES: *N(*)CCCCCO]
In certain embodiments, the polymers of the invention (e.g., a polymer of Formula (I) or (II)) comprise about 10-60 mol % Formula (B). In certain embodiments, the polymers of the invention comprise about 20-50 mol % Formula (B).

In certain embodiments, the polymers of the invention comprise about 24-42 mol % Formula (B). In certain particular embodiments, the polymers of the invention comprise 24, 25, 26, 27, 28, 29, 30, 31, 32, 33, 34, 35, 36, 37, 38, 39, 40, 41, or 42 mol % Formula (B).

In certain embodiments, all radicals of Formula (B) are the same. In other embodiments, there are two or more (e.g., 2, 3 or 4) different radicals of Formula (B).

Formula (C)

Formula (C) is a triradical having three points of attachment to radicals of Formula (A). Triradicals of Formula (C) are branch points in PBAEs of the invention. In certain embodiments, the polymers of the invention do not include a branch point of Formula (C).

In certain embodiments, Formula (C) is:

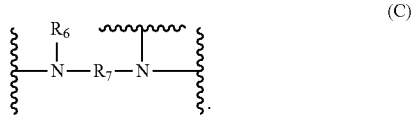

(C)

In certain embodiments, Formula (C) is of Formula (C1):

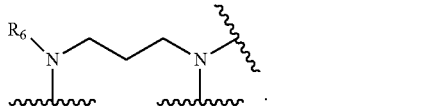

(C1)

In certain embodiments, $R_6$ is optionally substituted $C_{1-6}$ alkyl.

In certain embodiments, $R_7$ is optionally substituted $C_{1-6}$ alkyl, optionally substituted $C_{3-7}$ cycloalkyl, or optionally substituted $C_{1-6}$heteroalkyl.

In certain embodiments, Formula (C) is selected from:

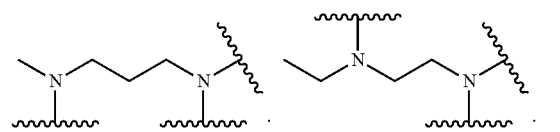

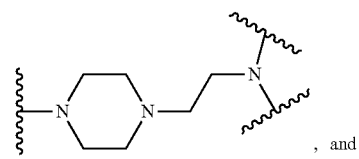, and

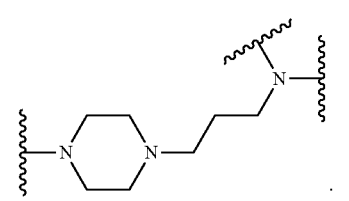.

In certain particular embodiments, Formula (C) has the structure:

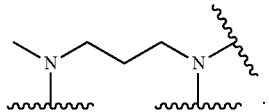 [SMILES: *N(*)CCCN(*)C]

In certain embodiments, the polymer of Formula (I) comprises about 0-50, about 0-40, about 0-30, about 0-20, or about 0-10 mol % Formula (C). In certain embodiments, the polymer of Formula (I) comprises about 0-10 mol % Formula (C). In certain particular embodiments, the polymer comprises 0, 1, 2, 3, 4, 5, 6, 7, 8, 9, or 10 mol % Formula (C).

Formula (D)

Formula (D) is a radical having one point of attachment to a radical of Formula (A). Radicals of Formula (D) occur at the termini of PBAE polymers of the invention.

In certain embodiments, Formula (D) is:

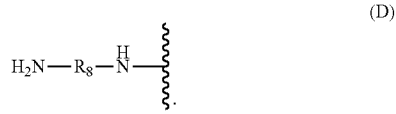

(D)

In certain embodiments, $R_8$ is optionally substituted aliphatic, optionally substituted heteroaliphatic, optionally substituted carbocyclylene, optionally substituted heterocyclylene, optionally substituted arylene, or optionally substituted heteroarylene. In certain embodiments, $R_8$ is optionally substituted aliphatic or optionally substituted heteroaliphatic. In certain embodiments, $R_8$ is optionally substituted $C_{1-6}$ alkylene, or optionally substituted $C_{1-6}$ heteroalkylene.

In certain embodiments, Formula (D) is of Formula (D1):

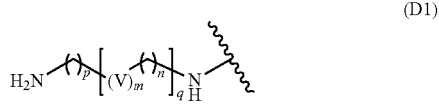

(D1)

wherein n, m, and p are each independently an integer between 0 and 20, inclusive; and V is —O—, —S—, —NH—, —NR$_V$—, or C(R$_V$)$_2$, wherein R$_V$ is hydrogen, hydroxyl, $C_{1-6}$aliphatic, $C_{1-6}$heteroaliphatic, $C_{1-6}$alkoxy, amino, $C_{1-6}$alkylamino, di($C_{1-6}$alkyl)amino, aryl, heteroaryl, thiol, akylthioxy, or acyl. In certain embodiments, n, m, p and q are each independently an integer between 1 and 15, inclusive. In yet other embodiments, n, m, p and q are each independently an integer between 1 and 12, inclusive. In other embodiments, n, m, p and q are each independently an integer between 1 and 10, inclusive. In other embodiments, n, m, p and q are each independently an integer between 0 and 6, inclusive. In still other embodiments n, m, p and q are each independently an integer between 0 and 3, inclusive. In certain embodiments, n, m, p and q are each independently 0, 1, 2, 3, 4, 5, or 6. In certain embodiments, the terminal amino group of Formula (D1) is alkylated (e.g., $C_1$-$C_{12}$ alkyl), acylated (e.g., acetyl), or otherwise modified.

In certain embodiments, Formula (D) is of Formula (D2):

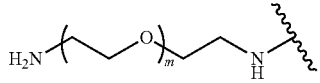
(D2)

wherein m is an integer between 0 and 20, inclusive. In certain embodiments, m is an integer between 1 and 15, inclusive. In yet other embodiments, m is an integer between 1 and 12, inclusive. In other embodiments, m is an integer between 1 and 10, inclusive. In other embodiments, m is an integer between 0 and 6, inclusive. In still other embodiments, m is an integer between 0 and 3, inclusive. In certain embodiments, m is 0, 1, 2, 3, 4, 5, or 6. In certain embodiments, the terminal amino group of Formula (D2) is protected, alkylated (e.g., $C_1$-$C_{12}$ alkyl), acylated (e.g., acetyl), or otherwise modified.

In certain embodiments, Formula (D) is of Formula (D3):

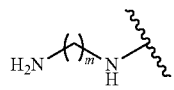
(D3)

wherein m is an integer between 1 and 20, inclusive. In certain embodiments, m is an integer between 2 and 15, inclusive. In yet other embodiments, m is an integer between 2 and 12, inclusive. In other embodiments, m is an integer between 2 and 10, inclusive. In other embodiments, m is an integer between 2 and 6, inclusive. In still other embodiments, m is 2 or 3.

In certain embodiments, Formula (D) is of Formula (D4):

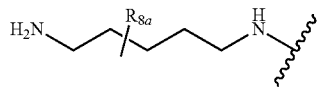
(D4)

wherein $R_{8a}$ is optionally substituted $C_{1-6}$ alkyl, or optionally substituted $C_{1-6}$ heteroalkyl. $R_{8a}$ is covalently attached to a carbon atom of the alkyl chain.

In certain embodiments, Formula (D) is selected from:

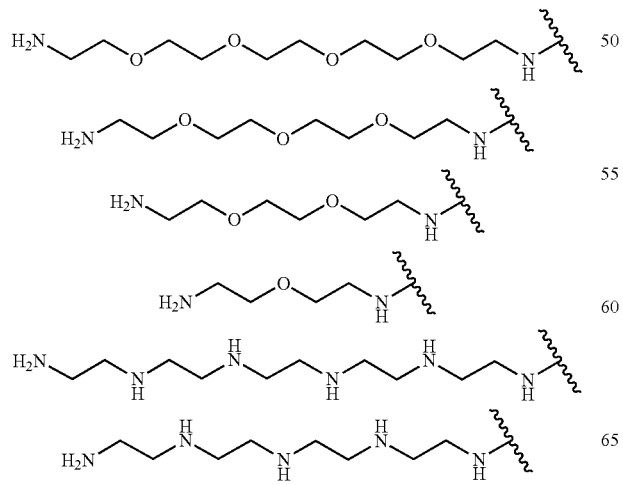

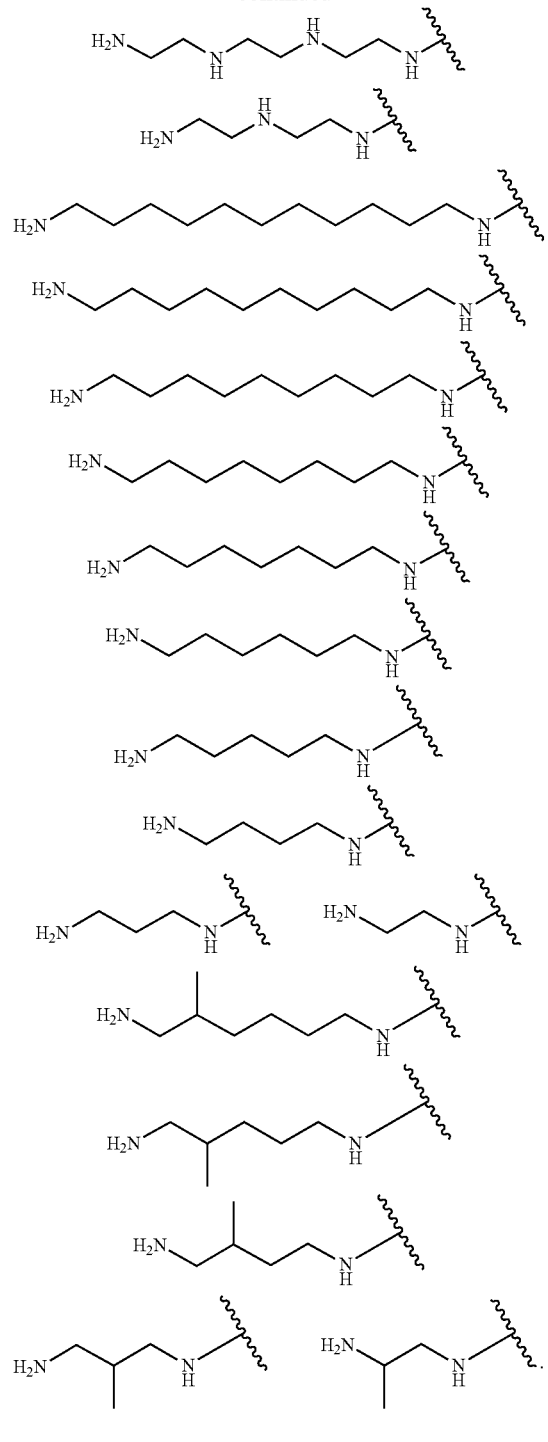

In certain particular embodiments, Formula (D) has the structure:

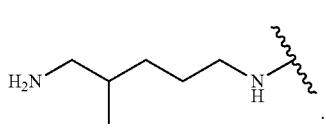 [SMILES: *NCCCC(C)CN]

In certain embodiments, the polymer comprises about 1-25 mol % Formula (D). In certain embodiments, the polymer comprises about 5-20 mol % Formula (D). In certain embodiments, the polymer comprises about 8-19 mol % Formula (D). In certain particular embodiments, the polymer comprises 8, 9, 10, 11, 12, 13, 14, 15, 16, 17, 18 or 19 mol % Formula (D).

Formula (E)

Formula (E) is a diradical having two points of attachment to radicals of Formula (A). The incorporation of radicals of Formula (E) facilitates formulation of the PBAE polymers of the invention with hydrophobic compounds, such as PEG-lipids. Formulation with PEG-lipids is associated with improved particle (e.g., nanoparticle) stability and transfection efficacy.

In certain embodiments, Formula (E) has the structure:

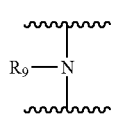

wherein $R_9$ is optionally substituted aliphatic.

In certain embodiments, Formula (E) is selected from the following:

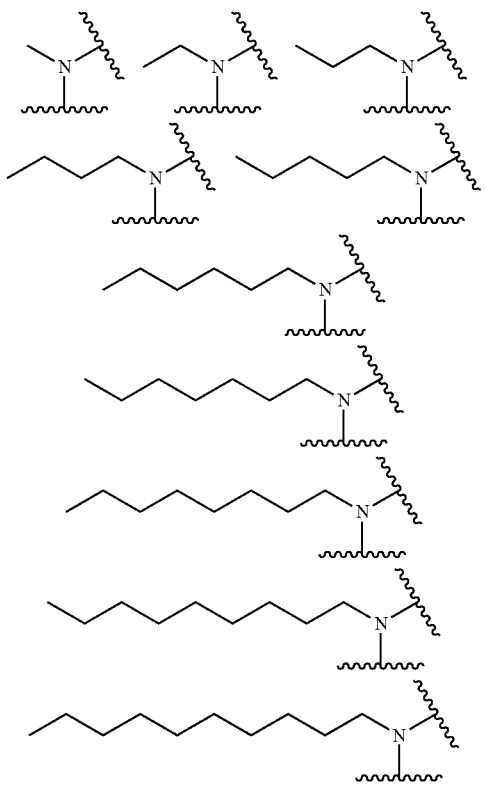

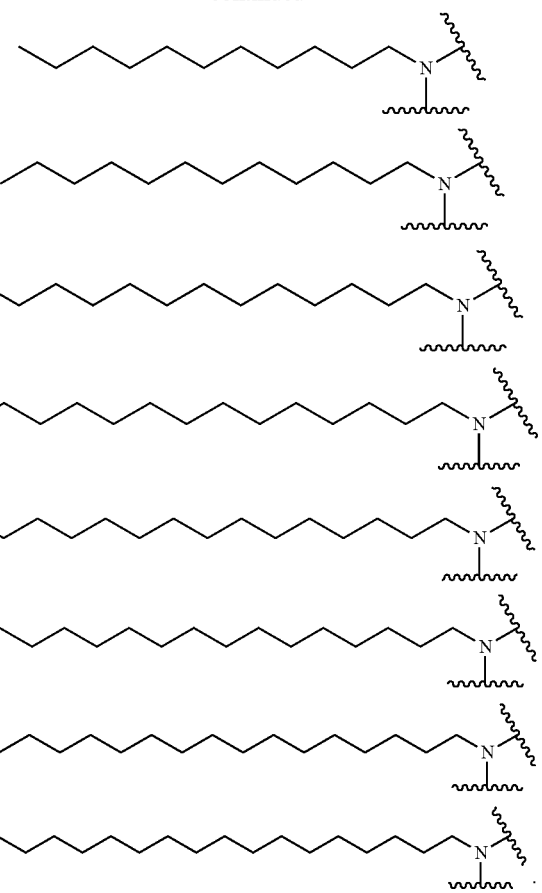

In certain embodiments, Formula (E) has the structure:

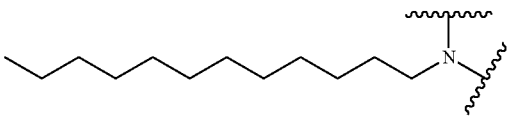

In certain embodiments, the polymers of the invention comprise about 0-50 mol % Formula (E). In certain particular embodiments, the polymers of the invention comprise 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mol % Formula (E).

Provided herein are certain embodiments of Formula (I), wherein:

(1) Formula (A) is selected from:

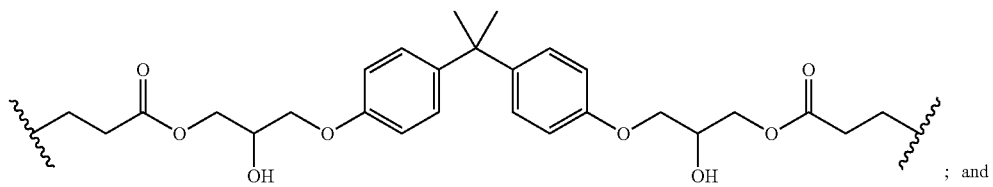
; and

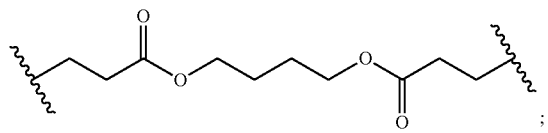
Formula (B) is selected from:
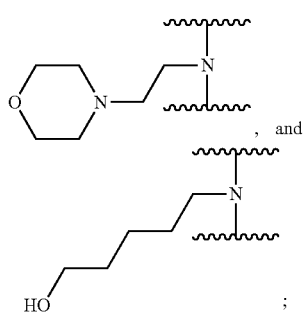
Formula (C) is selected from:
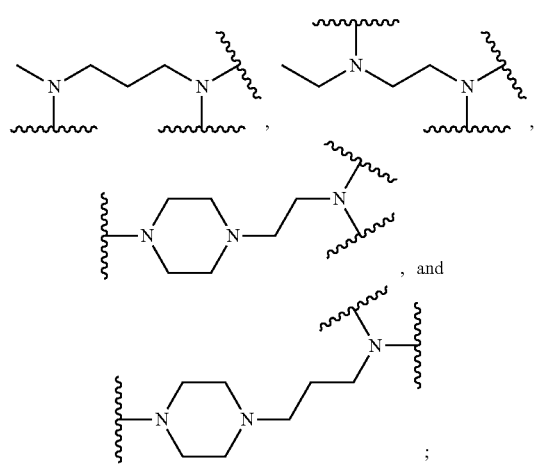
Formula (D) has a structure selected from:
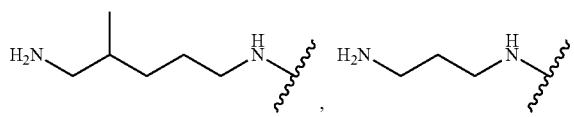
and
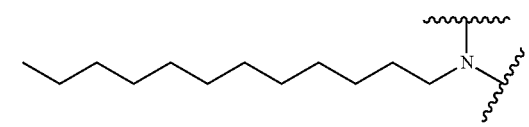
and
Formula (E), if present, has the structure:
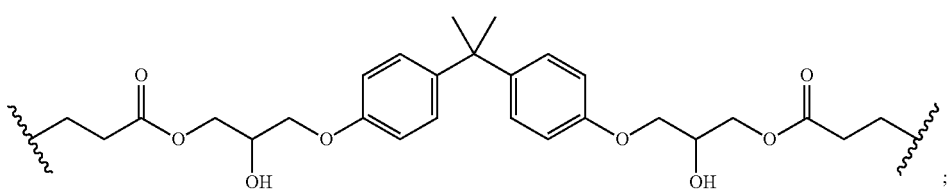 [SMILES: *CCC(=O)OCC(O)COc1ccc(C(C)(C)c2ccc(OCC(O)COC(=O)CC*)cc2)cc1]
(2) Formula (A) has the structure:

Formula (B) has the structure:

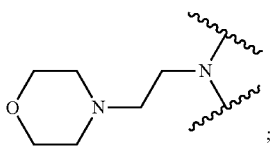 [SMILES: *N(*)CCN1CCOCC1]
;

Formula (C) has the structure:

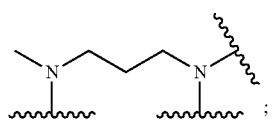 [SMILES: *N(*)CCCN(*)C]
;

and
Formula (D) has the structure:

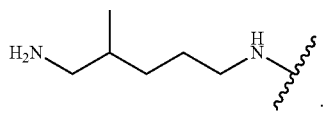
.

(3) Formula (A) has the structure:

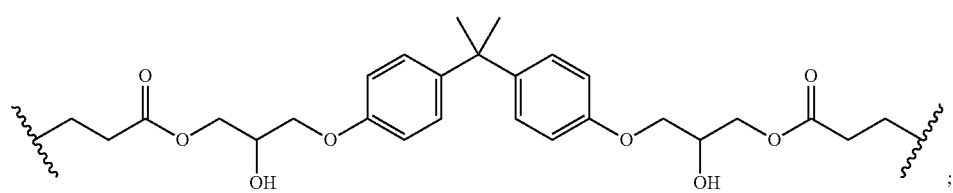 [SMILES: *CCC(=O)OCC(O)COc1ccc(C(C)(C)c2ccc(OCC(O)COC(=O)CC*)cc2)cc1]
;

Formula (B) has the structure:

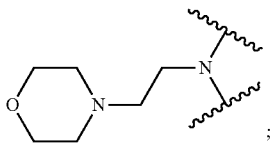 [SMILES: *N(*)CCN1CCOCC1]
;

Formula (C) has the structure:

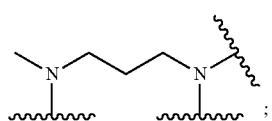 [SMILES: *N(*)CCCN(*)C]
;

Formula (D) has the structure:

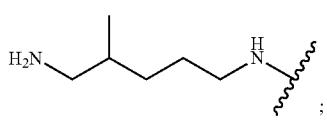 [SMILES: *NCCCC(C)CN]
;

and
Formula (E) has the structure:

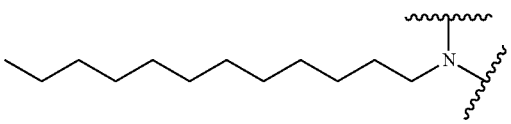
.

(4) Formula (A) has the structure:

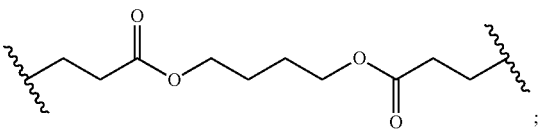 [SMILES: *CCC(=O)OCCCCOC(=O)CC*]
;

Formula (B) has the structure:

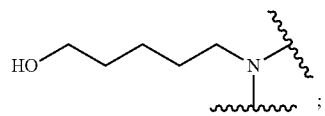 [SMILES: *N(*)CCCCCO]
;

Formula (C) has the structure:

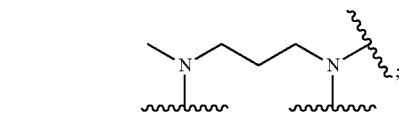 [SMILES: *N(*)CCCN(*)C]
;

and
Formula (D) has the structure:

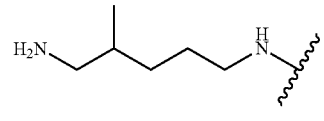
;

(5) Formula (A) has the structure:

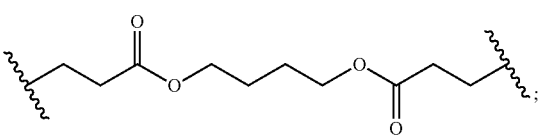 [SMILES: *CCC(=O)OCCCCOC(=O)CC*]
;

Formula (B) has the structure:

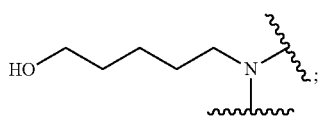 [SMILES: *N(*)CCCCCO]

and

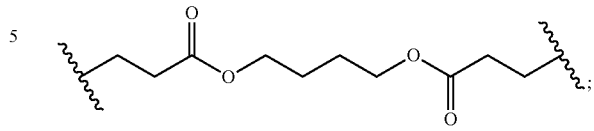

Formula (B) is selected from:

Formula (C) has the structure:

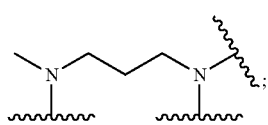 [SMILES: *N(*)CCCN(*)C]

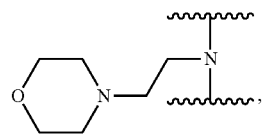

and

Formula (D) has the structure:

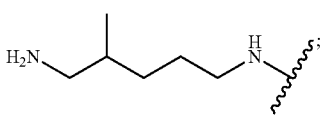 [SMILES: *NCCCC(C)CN]

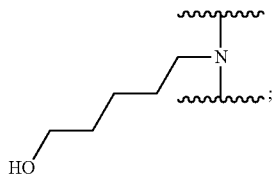

and

Formula (D) has a structure selected from:

Formula (E) has the structure:

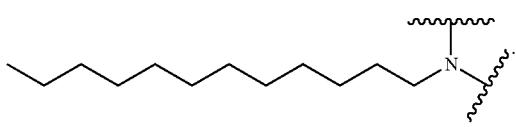 [SMILES: *N(*)CCCCCCCCCCCC]

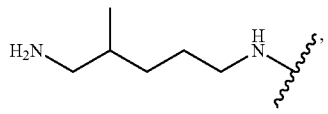

In embodiments (1)-(5), the polymer of Formula (I) may have a DB of 0.1, 0.2, 0.3, 0.4 or 0.5. Embodiments (1), (2) and (4) may comprise radicals of Formulae (A), (B), (C) and (D) in a molar ratio of about 1:0.5:0.2:0.39; 1:0.67:0.13:0.27; 1:0.8:0.08:0.16; or 1:0.94:0:0.07. Embodiments (1), (3) and (5) may comprise radicals of Formulae (A), (B), (C), (D) and (E) in a molar ratio of about 1:0.35:0.2:0.39:0.15; 1:0.47:0.13:0.27:0.2; 1:0.56:0.08:0.16:0.24; or 1:0.66:0:0.07:0.28.

Also provided herein are certain embodiments of Formula (II), wherein:

(6) Formula (A) is selected from:

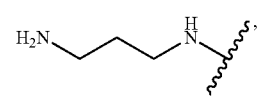

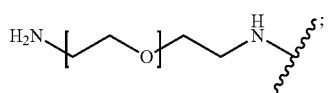

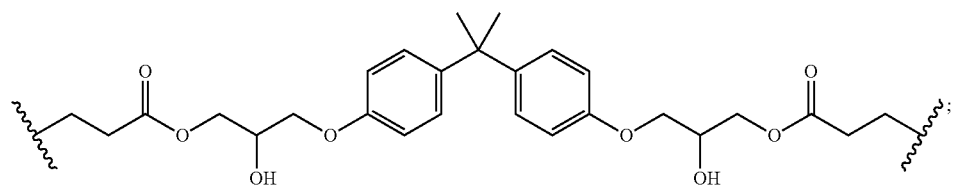 [SMILES: *CCC(=O)OCC(O)COc1ccc(C(C)(C)c2ccc(OCC(O)COC(=O)CC*)cc2)cc1]

and
Formula (E), if present, has the structure:
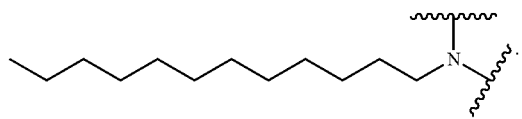 [SMILES: *N(*)CCCCCCCCCCCC]
(7) Formula (A) has the structure:
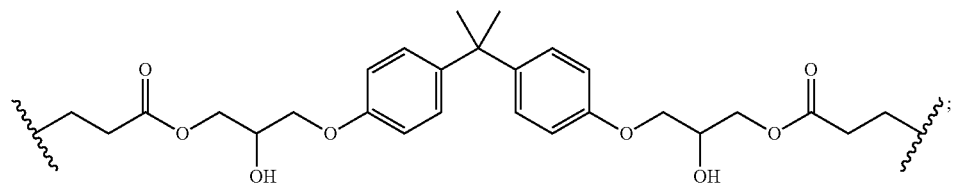 [SMILES: *CCC(=O)OCC(O)COc1ccc(C(C)(C)c2ccc(OCC(O)COC(=O)CC*)cc2)cc1]
Formula (B) has the structure:
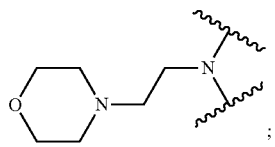 [SMILES: *N(*)CCN1CCOCC1]
and
Formula (D) has the structure:
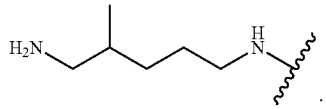 [SMILES: *NCCCC(C)CN]
(8) Formula (A) has the structure:
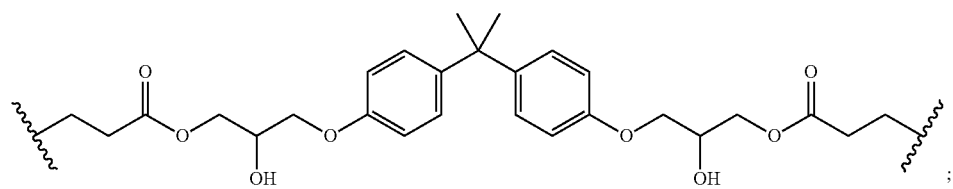 [SMILES: *CCC(=O)OCC(O)COc1ccc(C(C)(C)c2ccc(OCC(O)COC(=O)CC*)cc2)cc1]
Formula (B) has the structure:
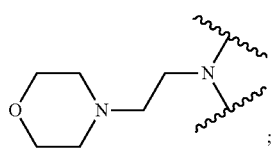 [SMILES: *N(*)CCN1CCOCC1]
Formula (D) has the structure:
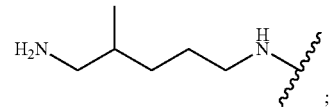 [SMILES: *NCCCC(C)CN]
and
Formula (E) has the structure:
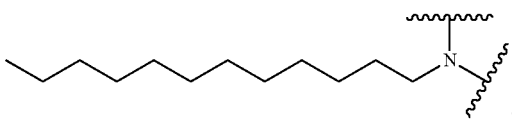
(9) Formula (A) has the structure:
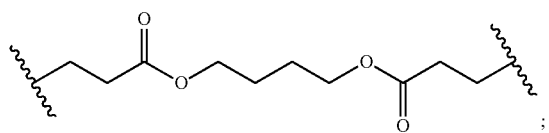 [SMILES: *CCC(=O)OCCCCOC(=O)CC*]
Formula (B) has the structure:
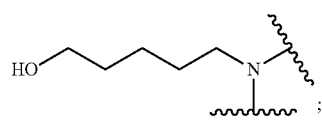 [SMILES: *N(*)CCCCCO]

and
Formula (D) has the structure:

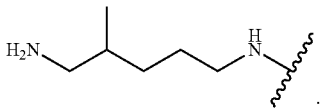 [SMILES: *NCCCC(C)CN]

(10) Formula (A) has the structure:

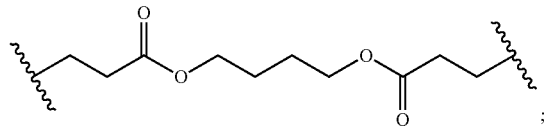 [SMILES: *CCC(=O)OCCCCOC(=O)CC*]

Formula (B) has the structure:

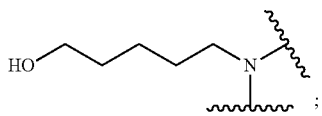

Formula (D) has the structure:

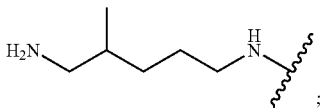 [SMILES: *NCCCC(C)CN]

and
Formula (E) has the structure:

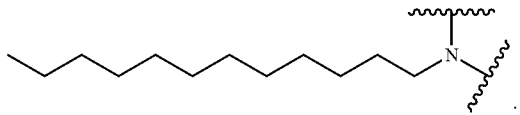 [SMILES: *N(*)CCCCCCCCCCCC]

Methods of Preparation

Provided herein is a method of preparing a polymer of Formula (I), comprising:

(i) combining a bis(acrylate) compound of Formula (A'):

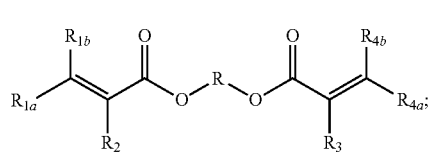

with a compound of Formula (B'):

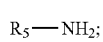

a compound of Formula (C'):

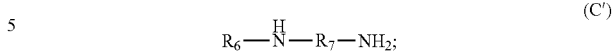

and
optionally, a compound of Formula (E'):

wherein:

R is optionally substituted aliphatic, optionally substituted heteroaliphatic, optionally substituted carbocyclyl, optionally substituted heterocyclyl, optionally substituted optionally substituted arylene, optionally substituted heteroarylene, or a combination thereof;

$R_{1a}$, $R_{1b}$, $R_2$, $R_3$, $R_{4a}$, and $R_{4b}$ are each independently hydrogen, halogen, hydroxyl, alkoxyl, cyano, optionally substituted aliphatic, or optionally substituted heteroaliphatic;

$R_5$ is optionally substituted aliphatic, optionally substituted heteroaliphatic, optionally substituted carbocyclyl, optionally substituted heterocyclyl, optionally substituted optionally substituted aryl, or optionally substituted heteroaryl;

$R_6$ is optionally substituted aliphatic, optionally substituted heteroaliphatic, optionally substituted carbocyclyl, optionally substituted heterocyclyl, optionally substituted optionally substituted aryl, or optionally substituted heteroaryl;

$R_7$ is optionally substituted aliphatic, optionally substituted heteroaliphatic, optionally substituted carbocyclylene, optionally substituted heterocyclylene, optionally substituted optionally substituted arylene, or optionally substituted heteroarylene;

$R_9$ is optionally substituted aliphatic; and

Formulae (B'), (C') and (E') are different from one another; and (ii) combining the product of step (I) with a compound of Formula (D'):

wherein $R_8$ is optionally substituted aliphatic, optionally substituted heteroaliphatic, optionally substituted carbocyclylene, optionally substituted heterocyclylene, optionally substituted optionally substituted arylene, or optionally substituted heteroarylene; and Formulae (B'), (C'), (D') and (E') are different from one another;

such that a polymer of Formula (I) is formed.

Provided herein are certain embodiments of the method, wherein:
(1) Formula (A') has a structure selected from:
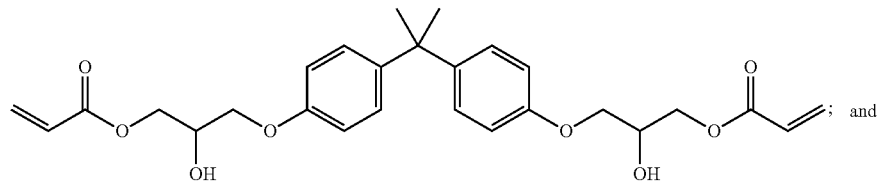
and
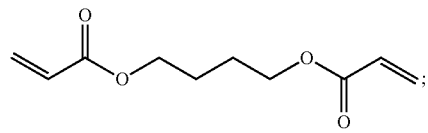
Formula (B') has a structure selected from:
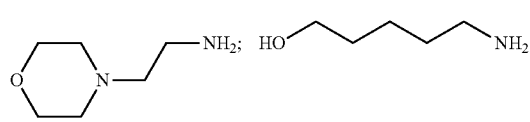
and
Formula (C') has the structure:
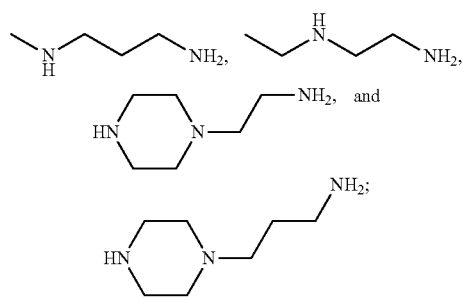
Formula (D') has a structure selected from:
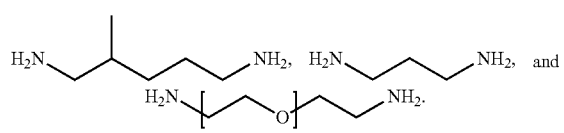
(2) Formula (A') has the structure:
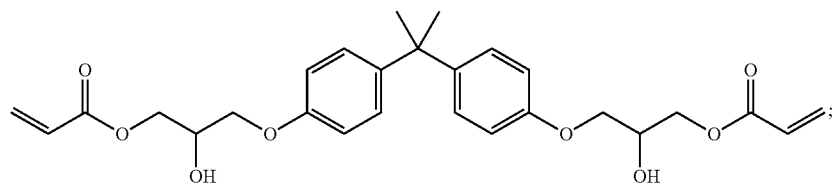 [SMILES: C=CC(=O)OCC(O)COc1ccc(C(C)(C)c2ccc(OCC(O)COC(=O)C=C)cc2)cc1]
Formula (B') has the structure:
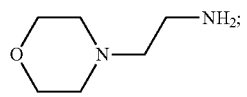
Formula (C') has the structure:
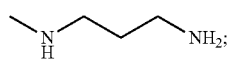
and
Formula (D') has the structure:
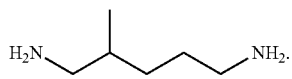

(3) Formula (A') has the structure:

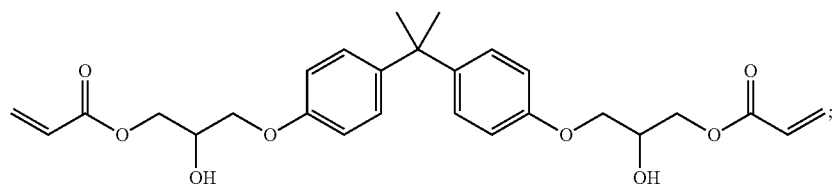 [SMILES: C=CC(=O)OCC(O)COc1ccc(C(C)(C)c2ccc(OCC(O)COC(=O)C=C)cc2)cc1]

Formula (B') has the structure:

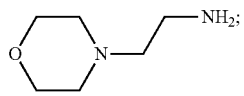

Formula (C') has the structure:

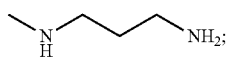

and
Formula (D') has the structure:

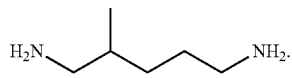

Formula (E') has the structure:

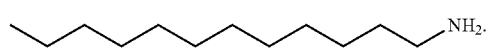

(4) Formula (A') has the structure:

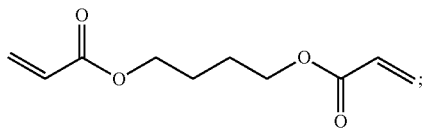

Formula (B') has the structure:

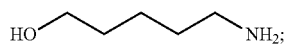

Formula (C') has the structure:

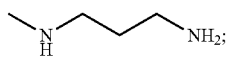

and
Formula (D') has the structure:

(5) Formula (A') has the structure:

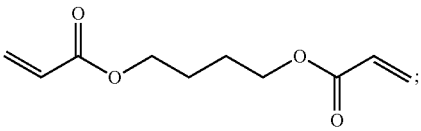

Formula (B') has the structure:

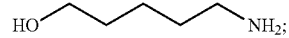

Formula (C') has the structure:

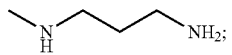

and
Formula (D') has the structure:

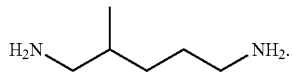

Formula (E') has the structure:

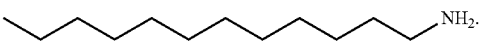

In one aspect, provided herein is a polymer of Formula (I) prepared according to a method described herein, for example, Examples 2 and 4.

In certain embodiments, the monomers are reacted at temperatures ranging from 25 C to 90 C for 24 to 72 hours. Monomers of Formulae (A'), (B') and/or (E') may be added at the same time or in steps. In certain embodiments, monomers of Formulae (A') and (C') are reacted at 40 C for 24 h (because secondary amines in the triradical are reactive at lower temp) and then monomers of Formulae (B') and/or (E') added at 24 h and reacted at 90 C for a further 24-48 h.

In certain embodiments, all monomers are added at same time at a temp of 40 C for 6 h followed by an increase in temp to 90 C and stirred up to 48 h. In other embodiments, all monomers added at same time and reacted at 90 C for 48 h.

Polymers of the invention may be prepared or used according as described in WO 2002/031025, WO 2004/106411, and WO 2008/011561, the entire contents of which are incorporated by reference.

Agents

Provided herein in another aspect are method of delivering an agent to a cell comprising contacting the cell with a composition comprising a polymer of the invention. In certain embodiments, the method is in vitro, ex vivo, or in vivo. In certain embodiments, the method is in vitro or ex vivo and the cell is selected from HeLa (cervical epithelium), A549 (lung epithelium) and C2C12 (myoblasts and myotubes). In certain embodiments, the method is in vivo and the cell is selected from a muscle cell, lung epithelial cell, lung endothelial cell, spleen cell and immune cell (CD45+). In certain particular embodiments, the cell is a lung cell. In certain particular embodiments, the cell is a lung epithelial cell. In other particular embodiments, the cell is a spleen cell.

The agents to be delivered by polymers and compositions of the present invention may be therapeutic, diagnostic, or prophylactic agents. Any chemical compound to be administered to an individual may be delivered using the inventive polymers, compositions, complexes, picoparticles, nanoparticles, microparticles, micelles, or liposomes. The agent may be a small molecule, organometallic compound, organic compound, inorganic compound, nucleic acid, protein, peptide, polynucleotide, metal, isotopically labeled chemical compound, drug, vaccine, immunological agent, etc.

In certain embodiments, the agents are organic compounds with pharmaceutical activity. In another embodiment of the invention, the agent is a clinically used drug (e.g., a drug approved in the United States by the FDA or in Europe by the EMA). In certain embodiments, the drug is an antibiotic, anti-viral agent, anesthetic, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, non-steroidal anti-inflammatory agent, nutritional agent, etc.

In certain embodiments, the agent to be delivered is a mixture of agents. The mixture may include 2-10 agents. For example, the mixture may include 2, 3, 4, 5, 6, 7, 8, 9 or 10 agents.

Diagnostic agents include gases; metals; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

Prophylactic agents include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, Freund's adjuvant, etc. Prophylactic agents include antigens of such bacterial organisms as *Streptococccus pneumoniae*, *Haemophilus influenzae*, *Staphylococcus aureus*, *Streptococcus pyrogenes*, *Corynebacterium diphtheriae*, *Listeria monocytogenes*, *Bacillus anthracis*, *Clostridium tetani*, *Clostridium botulinum*, *Clostridium perfringens*, *Neisseria meningitidis*, *Neisseria gonorrhoeae*, *Streptococcus mutans*, *Pseudomonas aeruginosa*, *Salmonella typhi*, *Haemophilus parainfluenzae*, *Bordetella pertussis*, *Francisella tularensis*, *Yersinia pestis*, *Vibrio cholerae*, *Legionella pneumophila*, *Mycobacterium tuberculosis*, *Mycobacterium leprae*, *Treponema pallidum*, *Leptospirosis interrogans*, *Borrelia burgdorferi*, *Campylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans*, *Histoplasma capsulatum*, *Candida albicans*, *Candida tropicalis*, *Nocardia asteroides*, *Rickettsia ricketsii*, *Rickettsia typhi*, *Mycoplasma pneumoniae*, *Chlamydial psittaci*, *Chlamydial trachomatis*, *Plasmodium falciparum*, *Trypanosoma brucei*, *Entamoeba histolytica*, *Toxoplasma gondii*, *Trichomonas vaginalis*, *Schistosoma mansoni*, and the like. These antigens may be in the form of whole killed organisms, peptides, proteins, glycoproteins, carbohydrates, or combinations thereof.

Polynucleotide

The polynucleotide to be complexed, encapsulated by the polymers of the invention, or included in a composition with the polymers of the invention, may be any nucleic acid including, but not limited to, RNA and DNA.

In certain embodiments, the polynucleotide is DNA. In certain particular embodiments, the DNA is genomic DNA, synthetic DNA, a synthetic analog of DNA, cDNA or a DNA/RNA hybrid.

In certain embodiments, the polynucleotide is RNA. In certain embodiments, the polynucleotide is mRNA, siRNA, ssRNA, dsRNA, shRNA, miRNA. In certain particular embodiments, the polynucleotide is mRNA.

In certain embodiments, the polynucleotide is an RNA that carries out RNA interference (RNAi). The phenomenon of RNAi is discussed in greater detail, for example, in the following references, each of which is incorporated herein by reference: Elbashir et al., 2001, *Genes Dev.*, 15:188; Fire et al., 1998, *Nature*, 391:806; Tabara et al., 1999, *Cell*, 99:123; Hammond et al., *Nature*, 2000, 404:293; Zamore et al., 2000, *Cell*, 101:25; Chakraborty, 2007, *Curr. Drug Targets*, 8:469; and Morris and Rossi, 2006, *Gene Ther.*, 13:553.

In certain embodiments, the polynucleotide is a dsRNA (double-stranded RNA).

In certain embodiments, the polynucleotide is an siRNA (short interfering RNA).

In certain embodiments, the polynucleotide is an shRNA (short hairpin RNA).

In certain embodiments, the polynucleotide is an miRNA (micro RNA). Micro RNAs (miRNAs) are genomically encoded non-coding RNAs of about 21-23 nucleotides in length that help regulate gene expression, particularly during development (see, e.g., Bartel, 2004, *Cell*, 116:281; Novina and Sharp, 2004, *Nature*, 430:161; and U.S. Patent Publication 2005/0059005; also reviewed in Wang and Li, 2007, Front. Biosci., 12:3975; and Zhao, 2007, *Trends Biochem. Sci.*, 32:189; each of which are incorporated herein by reference).

In certain embodiments, the polynucleotide is an antisense RNA.

In some embodiments, an RNA can be designed and/or predicted using one or more of a large number of available algorithms. To give but a few examples, the following resources can be utilized to design and/or predict dsRNA, siRNA, shRNA and/or miRNA: algorithms found at Alnylum Online, Dharmacon Online, OligoEngine Online, Molecula Online, Ambion Online, BioPredsi Online, RNAi Web Online, Chang Bioscience Online, Invitrogen Online, LentiWeb Online GenScript Online, Protocol Online; Reynolds et al., 2004, *Nat. Biotechnol.*, 22:326; Naito et al., 2006, *Nucleic Acids Res.*, 34:W448; Li et al., 2007, *RNA*, 13:1765; Yiu et al., 2005, *Bioinformatics*, 21:144; and Jia et al., 2006, *BMC Bioinformatics*, 7: 271; each of which is incorporated herein by reference).

The polynucleotides may be of any size or sequence, and they may be single- or double-stranded. In certain embodiments, the polynucleotide is greater than 100 base pairs long. In certain embodiments, the polynucleotide is greater than 1000 base pairs long and may be greater than 10,000 base pairs long. The polynucleotide is optionally purified and substantially pure. Preferably, the polynucleotide is greater than 50% pure, more preferably greater than 75% pure, and most preferably greater than 95% pure. The polynucleotide may be provided by any means known in the art. In certain embodiments, the polynucleotide has been engineered using recombinant techniques (for a more detailed description of these techniques, please see Ausubel et al. *Current Protocols in Molecular Biology* (John Wiley & Sons, Inc., New York, 1999); *Molecular Cloning: A Laboratory Manual*, 2nd Ed., ed. by Sambrook, Fritsch, and Maniatis (Cold Spring Harbor Laboratory Press: 1989); each of which is incorporated herein by reference). The polynucleotide may also be obtained from natural sources and purified from contaminating components found normally in nature. The polynucleotide may also be chemically synthesized in a laboratory. In certain embodiments, the polynucleotide is synthesized using standard solid phase chemistry.

The polynucleotide may be modified by chemical or biological means. In certain embodiments, these modifications lead to increased stability of the polynucleotide. Modifications include methylation, phosphorylation, end-capping, etc.

Derivatives of polynucleotides may also be used in the present invention. These derivatives include modifications in the bases, sugars, and/or phosphate linkages of the polynucleotide. Modified bases include, but are not limited to, those found in the following nucleoside analogs: 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine. Modified sugars include, but are not limited to, 2'-fluororibose, ribose, 2'-deoxyribose, 3'-azido-2',3'-dideoxyribose, 2',3'-dideoxyribose, arabinose (the 2'-epimer of ribose), acyclic sugars, and hexoses. The nucleosides may be strung together by linkages other than the phosphodiester linkage found in naturally occurring DNA and RNA. Modified linkages include, but are not limited to, phosphorothioate and 5'-N-phosphoramidite linkages. Combinations of the various modifications may be used in a single polynucleotide. These modified polynucleotides may be provided by any means known in the art; however, as will be appreciated by those of skill in this art, the modified polynucleotides are preferably prepared using synthetic chemistry in vitro.

The polynucleotides to be delivered may be in any form. For example, the polynucleotide may be a circular plasmid, a linearized plasmid, a cosmid, a viral genome, a modified viral genome, an artificial chromosome, etc.

The polynucleotide may be of any sequence. In certain embodiments, the polynucleotide encodes a protein or peptide. The encoded proteins may be enzymes, structural proteins, receptors, soluble receptors, ion channels, pharmaceutically active proteins, cytokines, interleukins, antibodies, antibody fragments, antigens, coagulation factors, albumin, growth factors, hormones, insulin, etc. The polynucleotide may also comprise regulatory regions to control the expression of a gene. These regulatory regions may include, but are not limited to, promoters, enhancer elements, repressor elements, TATA box, ribosomal binding sites, stop site for transcription, etc. In certain embodiments, the polynucleotide is not intended to encode a protein. For example, the polynucleotide may be used to fix an error in the genome of the cell being transfected.

The polynucleotide may also be provided as an antisense agent or RNA interference (RNAi) agent (Fire et al. *Nature* 391:806-811, 1998; incorporated herein by reference). Antisense therapy is meant to include, e.g., administration or in situ provision of single- or double-stranded oligonucleotides or their derivatives which specifically hybridize, e.g., bind, under cellular conditions, with cellular mRNA and/or genomic DNA, or mutants thereof, so as to inhibit expression of the encoded protein, e.g., by inhibiting transcription and/or translation (Crooke "Molecular mechanisms of action of antisense drugs" *Biochim. Biophys. Acta* 1489(1): 31-44, 1999; Crooke "Evaluating the mechanism of action of antiproliferative antisense drugs" *Antisense Nucleic Acid Drug Dev.* 10(2):123-126, discussion 127, 2000; *Methods in Enzymology volumes* 313-314, 1999; each of which is incorporated herein by reference). The binding may be by conventional base pair complementarity, or, for example, in the case of binding to DNA duplexes, through specific interactions in the major groove of the double helix (i.e., triple helix formation) (Chan et al. *J. Mol. Med.* 75(4):267-282, 1997; incorporated herein by reference).

In certain embodiments, the polynucleotide to be delivered comprises a sequence encoding an antigenic peptide or protein. Nanoparticles containing these polynucleotides can be delivered to an individual to induce an immunologic response sufficient to decrease the chance of a subsequent infection and/or lessen the symptoms associated with such an infection. The polynucleotide of these vaccines may be combined with interleukins, interferon, cytokines, and adjuvants such as cholera toxin, alum, Freund's adjuvant, etc. A large number of adjuvant compounds are known; a useful compendium of many such compounds is prepared by the National Institutes of Health and can be found on the internet (www.niaid.nih.gov/daids/vaccine/pdf/compendium.pdf, incorporated herein by reference; see also Allison *Dev. Biol. Stand.* 92:3-11, 1998; Unkeless et al. *Annu. Rev. Immunol.* 6:251-281, 1998; and Phillips et al. *Vaccine* 10:151-158, 1992, each of which is incorporated herein by reference).

The antigenic protein or peptides encoded by the polynucleotide may be derived from such bacterial organisms as Streptocococcus *pneumoniae*, Haemophilus *influenzae*, Staphylococcus *aureus*, Streptococcus *pyogenes*, Corynebacterium *diphtheriae*, Listeria *monocytogenes*, Bacillus *anthracis*, Clostridium *tetani*, Clostridium *botulinum*, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Campylobacter jejuni*, and the like; from such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; and from such fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like.

Polynucleotide Complexes

The ability of cationic polymers of the invention (e.g., protonated polymers of Formula (I)) to interact with negatively charged polynucleotides through electrostatic interactions is thought to at least partially prevent the degradation of the polynucleotide. By neutralizing the charge on the backbone of the polynucleotide, the neutral or slightly-positively-charged complex is also able to more easily pass through the hydrophobic membranes (e.g., cytoplasmic, lysosomal, endosomal, nuclear) of the cell. In certain embodiments, the complex is slightly positively charged. In certain embodiments, the complex has a positive ζ-potential, more preferably the ζ-potential is between 0 and +30.

The polymers of the present invention (e.g., polymers of Formula (I)) may comprise, primary, secondary, and tertiary amines. Although these amines are hindered, they are available to interact with a polynucleotide (e.g., DNA, RNA, synthetic analogs of DNA and/or RNA, DNA/RNA hydrids, etc.). Polynucleotides or derivatives thereof are contacted with the polymers of the invention under conditions suitable to form polynucleotide complexes. The polymer of the invention is preferably at least partially protonated so as to form a complex with the negatively charged polynucleotide. In certain embodiments, the polynucleotide complexes form particles that are useful in the delivery of polynucleotides to cells. In certain embodiments, multiple molecules of a polymer of the invention may be associated with a polynucleotide molecule. The complex may include 1-100 PBAE polymers, 1-1000, 10-1000 PBAE polymers, or 100-10,000 PBAE polymers.

Particles

The polymers of the present invention are useful as drug delivery vehicles. The polymers may be used to encapsulate agents including polynucleotides, small molecules, proteins, peptides, metals, organometallic compounds, etc. The polymers have several properties that make them particularly suitable in the preparation of drug delivery vehicles. These include: 1) the ability of the lipid to complex and "protect" labile agents; 2) the ability to buffer the pH in the endosome; 3) the ability to act as a "proton sponge" and cause endosomolytic; and/or 4) the ability to neutralize the charge on negatively charged agents. In certain embodiments, the polymers are used to form particles containing the agent to be delivered. These particles may include other materials, such as steroids (e.g., cholesterol), proteins, carbohydrates, synthetic polymers (e.g., PEG, PLGA), lipids, and natural polymers.

In certain embodiments, the particle is a microparticle or a nanoparticle. In certain embodiments, the diameter of the particles range from between 1 micrometer to 1,000 micrometers. In certain embodiments, the diameter of the particles range from between from 1 micrometer to 100 micrometers. In certain embodiments, the diameter of the particles range from between from 1 micrometer to 10 micrometers. In certain embodiments, the diameter of the particles range from between from 10 micrometer to 100 micrometers. In certain embodiments, the diameter of the particles range from between from 100 micrometer to 1,000 micrometers. In certain embodiments, the particles range from 1-5 micrometers. In certain embodiments, the diameter of the particles range from between 1 nm to 1,000 nm. In certain embodiments, the diameter of the particles range from between from 1 nm to 100 nm. In certain embodiments, the diameter of the particles range from between from 1 nm to 10 nm. In certain embodiments, the diameter of the particles range from between from 10 nm to 100 nm. In certain embodiments, the diameter of the particles range from between from 100 nm to 1,000 nm. In certain embodiments, the particles range from 1-5 nm. In certain embodiments, the diameter of the particles range from between 1 pm to 1,000 pm. In certain embodiments, the diameter of the particles range from between from 1 pm to 100 pm. In certain embodiments, the diameter of the particles range from between from 1 pm to 10 pm. In certain embodiments, the diameter of the particles range from between from 10 pm to 100 pm. In certain embodiments, the diameter of the particles range from between from 100 pm to 1,000 pm. In certain embodiments, the particles range from 1-5 pm.

Methods of Preparing Particles

Particles comprising polymers of the invention may be prepared using any method known in the art. These include, but are not limited to, lyophilization, spray drying, single and double emulsion solvent evaporation, solvent extraction, phase separation, simple and complex coacervation, and other methods well known to those of ordinary skill in the art. In certain embodiments, methods of preparing the particles are the double emulsion process and spray drying. The conditions used in preparing the particles may be altered to yield particles of a desired size or property (e.g., hydrophobicity, hydrophilicity, external morphology, "stickiness", shape, etc.). The method of preparing the particle and the conditions (e.g., solvent, temperature, concentration, air flow rate, etc.) used may also depend on the agent being encapsulated and/or the composition of the matrix.

Methods developed for making particles for delivery of encapsulated agents are described in the literature (for example, please see Doubrow, M., Ed., "Microcapsules and Nanoparticles in Medicine and Pharmacy," CRC Press, Boca Raton, 1992; Mathiowitz and Langer, *J. Controlled Release* 5:13-22, 1987; Mathiowitz et al. *Reactive Polymers* 6:275-283, 1987; Mathiowitz et al. *J. Appl. Polymer Sci.* 35:755-774, 1988; each of which is incorporated herein by reference).

If the particles prepared by any of the above methods have a size range outside of the desired range, the particles can be sized, for example, using a sieve. The particle may also be coated. In certain embodiments, the particles are coated with a targeting agent. In other embodiments, the particles are coated to achieve desirable surface properties (e.g., a particular charge).

Compositions The present invention contemplates a polymer of the invention, e.g., a polymer of Formula (I), as a component of a composition. For example, in certain embodiments, provided is a composition comprising a polymer of the invention, or salt thereof, and optionally an excipient.

Compositions, as described herein, comprising a polymer of the invention and an excipient of some sort may be useful in a variety of medical and non-medical applications. For example, pharmaceutical compositions comprising a polymer of the invention and an excipient may be useful in the delivery of an effective amount of an agent to a subject in need thereof. Nutraceutical compositions comprising a polymer of the invention and an excipient may be useful in the delivery of an effective amount of a nutraceutical, e.g., a dietary supplement, to a subject in need thereof. Cosmetic compositions comprising a polymer of the invention and an excipient may be formulated as a cream, ointment, balm, paste, film, or liquid, etc., and may be useful in the application of make-up, hair products, and materials useful for personal hygiene, etc. Compositions comprising a polymer of the invention and an excipient may be useful for non-medical applications, e.g., such as an emulsion or emulsifier, useful, for example, as a food component, for extinguishing fires, for disinfecting surfaces, for oil cleanup, etc.

Peptides play significant roles in endogenous cellular signaling and trafficking pathways, and offer tremendous potential in leveraging such interactions to enhance the delivery efficiency of systems which incorporate peptide moieties. Thus, compositions comprising a polymer of the invention and an excipient may further be useful in bioprocessing, such as a cell's bioprocessing of a commercially useful chemical or fuel. For example, intracellular delivery of the polymer of the invention or an agent complexed thereto may be useful in bioprocessing by maintaining the cell's health and/or growth, e.g., in the manufacturing of proteins.

The composition may comprise one type of polymer of the invention but may also comprise any number of different types, e.g., 1, 2, 3, 4, 5, 6, 7, 8, 9, 10 or more different types of polymers of the invention.

Accordingly, provided herein in another aspect is a composition comprising a polymer of the invention, e.g., a polymer of Formula (I). In certain embodiments, the composition is a cosmetic composition. In certain embodiments, the composition is a pharmaceutical composition and further comprises a pharmaceutically acceptable carrier.

The composition may comprise an agent, as described herein. When the agent is a polynucleotide, the composition may be characterized in terms of an N/P ratio (i.e., the ratio of moles of the amine groups of the polymer of the invention to moles of the phosphate groups of the polynucleotide). In certain embodiments, the N/P ratio of compositions of the invention is in the range of 1-70, 5-60, 5-50, 10-40, or 20-30.

In certain embodiments, the composition is formulated for intravenous delivery. In certain embodiments, the composition is formulated for aerosol delivery. In certain embodiments, the composition is in the form of a particle.

In certain embodiments, the particle is produced by lyophilization. In certain embodiments, the lyophilized particle comprises a carbohydrate additive. In certain embodiments, the carbohydrate is a non-reducing sugar. In certain particular embodiments, the non-reducing sugar is sucrose. In certain embodiments, the lyophilized particle is retains at least about 20%, at least about 30%, at least about 40%, at least about 50%, at least about 60%, at least about 70%, at least about 80%, or at least about 90% efficacy after storage for 14-90 days at −80° C. In certain embodiments, the composition is formulated at a pH of about 5.2 to about 7.4.

Pharmaceutical Compositions

Once the complexes, micelles, liposomes, or particles have been prepared, they may be combined with one or more pharmaceutical excipients to form a pharmaceutical composition that is suitable to administer to animals including humans. As would be appreciated by one of skill in this art, the excipients may be chosen based on the route of administration as described below, the agent being delivered, time course of delivery of the agent, etc.

Pharmaceutical compositions of the present invention and for use in accordance with the present invention may include a pharmaceutically acceptable excipient or carrier. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and/or to animals, orally, rectally, parenterally, intracisternally, intravaginally, intranasally, intraperitoneally, topically (as by powders, creams, ointments, or drops), bucally, or as an oral or nasal spray.

Liquid dosage forms for oral administration include pharmaceutically acceptable emulsions, microemulsions, solutions, suspensions, syrups, and elixirs. In addition to the active ingredients (i.e., microparticles, nanoparticles, liposomes, micelles, polynucleotide/lipid complexes), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid dosage forms for oral administration include capsules, tablets, pills, powders, and granules. In such solid dosage forms, the particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulation, ear drops, and eye drops are also contemplated as being within the scope of this invention.

The ointments, pastes, creams, and gels may contain, in addition to the particles of this invention, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the particles of this invention, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the microparticles or nanoparticles in a proper medium. Absorption enhancers can also be used to increase the flux of the compound across the skin. The rate can be controlled by either providing a rate controlling membrane or by dispersing the particles in a polymer matrix or gel.

These and other aspects of the present invention will be further appreciated upon consideration of the following Examples, which are intended to illustrate certain particular embodiments of the invention but are not intended to limit its scope, as defined by the claims.

Targeting Agents

The inventive polymer, compositions, complexes, liposomes, micelles, microparticles, picoparticles, and nanoparticles may be modified to include targeting agents since it is often desirable to target a particular cell, collection of cells, or tissue. A variety of targeting agents that direct pharmaceutical compositions to particular cells are known in the art (see, for example, Cotten et al., *Methods Enzym.* 217:618, 1993; incorporated herein by reference). The targeting agents may be included throughout the particle or may be only on the surface. The targeting agent may be a protein, peptide, carbohydrate, glycoprotein, lipid, small molecule, nucleic acid, etc. The targeting agent may be used to target specific cells or tissues or may be used to promote endocytosis or phagocytosis of the particle. Examples of targeting agents include, but are not limited to, antibodies, fragments of antibodies, low-density lipoproteins (LDLs), transferrin, asialycoproteins, gp120 envelope protein of the human immunodeficiency virus (HIV), carbohydrates, receptor ligands, sialic acid, etc. If the targeting agent is included throughout the particle, the targeting agent may be included in the mixture that is used to form the particles. If the targeting agent is only on the surface, the targeting agent may be associated with (i.e., by covalent, hydrophobic, hydrogen bonding, van der Waals, or other interactions) the formed particles using standard chemical techniques.

Treatment Methods

It is estimated that over 10,000 human diseases are caused by genetic disorders, which are abnormalities in genes or chromosomes. See, e.g., McClellan, J. and M. C. King, *Genetic heterogeneity in human disease*. Cell. 141(2): p. 210-7; Leachman, S. A., et al., *Therapeutic siRNAs for dominant genetic skin disorders including pachyonychia congenita*. J Dermatol Sci, 2008. 51(3): p. 151-7. Many of these diseases are fatal, such as cancer, severe hypercholesterolemia, and familial amyloidotic polyneuropathy. See, e.g., Frank-Kamenetsky, M., et al., *Therapeutic RNAi targeting PCSK9 acutely lowers plasma cholesterol in rodents and LDL cholesterol in nonhuman primates*. Proc Natl Acad Sci USA, 2008. 105(33): p. 11915-20; Coelho, T., *Familial amyloid polyneuropathy: new developments in genetics and treatment*. Curr Opin Neurol, 1996. 9(5): p. 355-9. Since the discovery of gene expression silencing via RNA interference (RNAi) by Fire and Mello (Fire, A., et al., *Potent and specific genetic interference by double-stranded RNA in Caenorhabditis elegans*. Nature, 1998. 391(6669): p. 806-11), there has been extensive effort toward developing therapeutic applications for RNAi in humans. See, e.g., Davis, M. E., *The first targeted delivery of siRNA in humans via a self-assembling, cyclodextrin polymer-based nanoparticle: from concept to clinic*. Mol Pharm, 2009. 6(3): p. 659-68; Whitehead, K. A., R. Langer, and D. G. Anderson, *Knocking down barriers: advances in siRNA delivery*. Nat. Rev. Drug Discovery, 2009. 8(2): p. 129-138; Tan, S. J., et al., *Engineering Nanocarriers for siRNA Delivery*. Small. 7(7): p. 841-56; Castanotto, D. and J. J. Rossi, *The promises and pitfalls of RNA-interference-based therapeutics*. Nature, 2009. 457(7228): p. 426-33; Chen, Y. and L. Huang, *Tumor-targeted delivery of siRNA by non-viral vector: safe and effective cancer therapy*. Expert Opin Drug Deliv, 2008. 5(12): p. 1301-11; Weinstein, S. and D. Peer, *RNAi nanomedicines: challenges and opportunities within the immune system*. Nanotechnology. 21(23): p. 232001; Fenske, D. B. and P. R. Cullis, *Liposomal nanomedicines*. Expert Opin Drug Deliv, 2008. 5(1): p. 25-44; and Thiel, K. W. and P. H. Giangrande, *Therapeutic applications of DNA and RNA aptamers*. Oligonucleotides, 2009. 19(3): p. 209-22. Currently, there are more than 20 clinical trials ongoing or completed involving siRNA therapeutics, which have shown promising results for the treatment of various diseases. See, e.g., Burnett, J. C., J. J. Rossi, and K. Tiemann, *Current progress of siRNA/shRNA therapeutics in clinical trials*. Biotechnol J. 6(9): p. 1130-46. However, the efficient and safe delivery of siRNA is still a key challenge in the development of siRNA therapeutics. See, e.g., Juliano, R., et al., *Biological barriers to therapy with antisense and siRNA oligonucleotides*. Mol Pharm, 2009. 6(3): p. 686-95.

Accordingly, provided herein are methods of using polymers of the invention, e.g., a polymer of Formula (I), for the treatment of a disease, disorder, or condition from which a subject suffers. It is contemplated that polymers of the invention will be useful in the treatment of a variety of diseases, disorders, or conditions, especially a system for delivering agents useful in the treatment of that particular disease, disorder, or condition. "Disease," "disorder," and "condition" are used interchangeably herein. In certain embodiments, the disease, disorder or condition from which a subject suffers is caused by an abnormality in a gene or chromosome of the subject.

For example, in one embodiment, provided is a method of treating disease, disorder, or condition from which a subject suffers, comprising administering to a subject in need thereof an effective amount of a composition comprising a polymer of the invention, e.g., a polymer of Formula (I), or salt thereof. Exemplary disease, disorder, or conditions contemplated include, but are not limited to, proliferative disorders, inflammatory disorders, autoimmune disorders, painful conditions, lung diseases, liver diseases, amyloid neuropathies, enzyme deficiencies and cystic fibrosis.

In certain particular embodiments, the method is for treating lung disease. In certain embodiments, the lung disease is asthma, chronic obstructive pulmonary disease (COPD), chronic bronchitis, emphysema, pulmonary hypertension, pulmonary fibrosis (e.g., idiopathic pulmonary fibrosis, fibrotic interstitial lung disease, interstitial pneumonia, fibrotic variant of non-specific interstitial pneumonia, or cystic fibrosis), sarcoidosis, influenza, pneumonia, tuberculosis, or lung cancer. In certain embodiments, the lung cancer is bronchogenic carcinoma, small cell lung cancer (SCLC), non-small cell lung cancer (NSCLC), or adenocarcinoma of the lung In certain embodiments, the composition further comprises, in addition to the polymer of the invention, a therapeutic agent useful in treating the disease, disorder, or condition. In certain embodiments, the polymer of the invention encapsulates the other (therapeutic) agent. In certain embodiments, the polymer of the invention and the other (therapeutic) agent form a particle (e.g., a nanoparticle, a microparticle, a micelle, a liposome, a lipoplex).

In certain embodiments, the condition is a proliferative disorder and, in certain embodiments, the composition further includes an anti-cancer agent. Exemplary proliferative diseases include, but are not limited to, tumors, benign neoplasms, pre-malignant neoplasms (carcinoma in situ), and malignant neoplasms (cancers).

Exemplary cancers include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

Anti-cancer agents encompass biotherapeutic anti-cancer agents as well as chemotherapeutic agents.

Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)).

Exemplary chemotherapeutic agents include, but are not limited to, anti-estrogens (e.g. tamoxifen, raloxifene, and megestrol), LHRH agonists (e.g. goscrelin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), antimetabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®)), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In certain embodiments, the condition is an inflammatory disorder and, in certain embodiments, the composition further includes an anti-inflammatory agent. The term "inflammatory disorder" refers to those diseases, disorders or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory disorders include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, sclerodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis.

In certain embodiments, the inflammatory disorder is inflammation associated with a proliferative disorder, e.g., inflammation associated with cancer.

In certain embodiments, the condition is an autoimmune disorder and, in certain embodiments, the composition further includes an immunomodulatory agent. Exemplary autoimmune disorders include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In certain embodiments, the condition is a painful condition and, in certain embodiments, the composition further includes an analgesic agent. A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

In certain embodiments, the painful condition is inflammatory pain. In certain embodiments, the painful condition (e.g., inflammatory pain) is associated with an inflammatory disorder and/or an autoimmune disorder.

In certain embodiments, the condition is a liver disease and, in certain embodiments, the composition further includes an agent useful in treating liver disease. Exemplary liver diseases include, but are not limited to, drug-induced liver injury (e.g., acetaminophen-induced liver injury), hepatitis (e.g., chronic hepatitis, viral hepatitis, alcohol-induced hepatitis, autoimmune hepatitis, steatohepatitis), non-alcoholic fatty liver disease, alcohol-induced liver disease (e.g., alcoholic fatty liver, alcoholic hepatitis, alcohol-related cirrhosis), hypercholesterolemia (e.g., severe hypercholesterolemia), transthyretin-related hereditary amyloidosis, liver cirrhosis, liver cancer, primary biliary cirrhosis, cholestatis, cystic disease of the liver, and primary sclerosing cholangitis. In certain embodiments the liver disease is associated with inflammation.

In certain embodiments, the condition is a familial amyloid neuropathy and, in certain embodiments, the composition further includes an agent useful in a familial amyloid neuropathy.

Compositions comprising a polymer of the invention may be administered in such amounts, time, and route deemed necessary in order to achieve the desired result. The exact amount of the active ingredient will vary from subject to subject, depending on the species, age, and general condition of the subject, the severity of the infection, the particular active ingredient, its mode of administration, its mode of activity, and the like. Compositions are preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

Kits

The invention also provides kits for use in preparing the polymers of the invention, or compositions thereof. The kit may include any or all of the following: amines of Formulae (B'), (C'), (D'), and/or (E'), diacrylates of Formula (A'), a combination of said amines and diacrylates, poly(beta-amino esters), vials, solvent, buffers, multi-well plates, salts, agents as described herein (e.g., polynucleotides, proteins, or small molecules) and instructions. The instructions include ways of preparing the inventive end-modified polymers with various properties. In certain embodiments, the kit is tailored for preparation of end-modified polymers with a desired property or for a desired use. In certain embodiments, the kit includes all the items necessary to prepare one or more polymers of the invention, or compositions thereof.

Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds and polymers described herein can comprise one or more asymmetric centers, and thus can exist in various stereoisomeric forms, e.g., enantiomers and/or diastereomers. For example, the polymers described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses polymers as individual isomers substantially free of other isomers, and alternatively, as mixtures of various isomers.

Unless otherwise stated, structures depicted herein are also meant to include polymers that differ only in the presence of one or more isotopically enriched atoms. For example, polymers having the present structures except for the replacement of hydrogen by deuterium or tritium, replacement of $^{19}$F with $^{18}$F, or the replacement of a carbon by a $^{13}$C- or $^{14}$C-enriched carbon are within the scope of the disclosure. Such polymers are useful, for example, as analytical tools or probes in biological assays.

When a range of values is listed, it is intended to encompass each value and subrange within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., 2-methylpentyl, 3-methylpentyl, 2,2-dimethylbutyl, 2,3-dimethylbutyl, and n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-10}$ alkyl (such as substituted $C_{1-6}$ alkyl, e.g., —$CH_2F$, —$CHF_2$, —$CF_3$ or benzyl (Bn)).

The term "alkoxy" refers to a radical of the formula —O(alkyl).

The term "carbamoyl" refers to a radical of formula —O(C=O)$NR_2$ or formula —N(R)(C=O)OR, wherein each R independently is hydrogen, optionally substituted aliphatic, optionally substituted heteroaliphatic, optionally substituted carbocyclyl, optionally substituted heterocyclyl, optionally substituted optionally substituted aryl, or optionally substituted heteroaryl.

The term "ureido" refers to a radical of the formula —N(R)(C=O)$NR_2$, wherein each R independently is hydrogen, optionally substituted aliphatic, optionally substituted heteroaliphatic, optionally substituted carbocyclyl, optionally substituted heterocyclyl, optionally substituted optionally substituted aryl, or optionally substituted heteroaryl.

The term "amido" refers to a radical of the formula —(C=O)$NR_2$ or formula —N(R)(C=O)R, wherein each R independently is hydrogen, optionally substituted aliphatic, optionally substituted heteroaliphatic, optionally substituted carbocyclyl, optionally substituted heterocyclyl, optionally substituted optionally substituted aryl, or optionally substituted heteroaryl.

The term "carbonyldioxyl" refers to a radical of the formula —O(C=O)OR, wherein each R independently is hydrogen, optionally substituted aliphatic, optionally substituted heteroaliphatic, optionally substituted carbocyclyl, optionally substituted heterocyclyl, optionally substituted optionally substituted aryl, or optionally substituted heteroaryl.

The term "alkylthioether" refers to a radical of the formula —R—S—R, wherein each R independently is optionally substituted alkyl.

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and for 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH$_3$ or

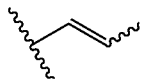

may be in the (E)- or (Z)-configuration.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and for 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and for 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

In some embodiments, "carbocyclyl" is a monocyclic, saturated radical having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 7 ring carbon atoms ("$C_{3-7}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl. In certain embodiments, the carbocyclyl includes 0, 1, or 2 C=C double bonds in the carbocyclic ring system, as valency permits.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

Groups recited herein in variable definitions are optionally substituted unless expressly provided otherwise. The term "optionally substituted" refers to being substituted or unsubstituted. In certain embodiments, aliphatic, alkyl, alkenyl, alkynyl, heteroaliphatic, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" aliphatic, "substituted" or "unsubstituted" alkyl, "substituted" or "unsubstituted" alkenyl, "substituted" or "unsubstituted"

alkynyl, "substituted" or "unsubstituted" heteroaliphatic, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable polymer, e.g., a polymer which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable polymer. The present invention contemplates any and all such combinations in order to arrive at a stable polymer. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{aa}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl), C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl), —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

In certain embodiments, the carbon atom substituents are independently halogen, substituted or unsubstituted C$_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$. In certain embodiments, the carbon atom substituents are independently halogen, substituted or unsubstituted C$_{1-6}$ alkyl, —OR$^{aa}$, —SR$^{aa}$, —N(R$^{bb}$)$_2$, —CN, —SCN, or —NO$_2$.

The term "halo" or "halogen" refers to fluorine (fluoro, —F), chlorine (chloro, —Cl), bromine (bromo, —Br), or iodine (iodo, —I).

The term "-hydroxyl" or "—OH" refers to the group —OH. The term "substituted hydroxyl" or "substituted —OH," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X$^-$ are as defined herein.

The term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), carboxylates (—CO$_2$), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$, —C(=NR$^{bb}$)N(R$^{bb}$)$_2$), wherein R$^{aa}$ and R$^{bb}$ are as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

The following definitions are more general terms used throughout the present application.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the polymers of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-OH-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

In certain embodiments, the polymer of Formula (I) is a salt. In certain particular embodiments, the polymer of Formula (I) is a pharmaceutically acceptable salt.

In certain embodiments, one or more radicals of Formulae (A), (B), (C), (D), (E), (A'), (B'), (C'), (D'), and (E') are salts. In certain particular embodiments, one or more radicals of Formulae (A), (B), (C), (D), (E), (A'), (B'), (C'), (D'), and (E') are pharmaceutically acceptable salts.

The terms "composition" and "formulation" are used interchangeably.

As used herein, the term "polyplex" refers to a complex comprising a polymer of the invention and one or more agents. In certain embodiments, a polyplex takes the form of a particle, such as a nanoparticle.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, cows, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant produces fruit. In some embodiments, the plant is a tree or shrub.

The term "administer," "administering," or "administration" refers to implanting, absorbing, ingesting, injecting, inhaling, or otherwise introducing a polymer described herein, or a composition thereof, in or on a subject.

The terms "treatment," "treat," and "treating" refer to reversing, alleviating, delaying the onset of, or inhibiting the progress of a disease (e.g., a bacterial infection) described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "prevent," "preventing," or "prevention" refers to a prophylactic treatment of a subject who is not and was not with a disease (e.g., a bacterial infection) but is at risk of developing the disease or who was with a disease, is not with the disease, but is at risk of regression of the disease. In certain embodiments, the subject is at a higher risk of developing the disease or at a higher risk of regression of the disease than an average healthy member of a population of subjects.

The terms "condition," "disease," and "disorder" are used interchangeably.

In general, the "effective amount" of an active ingredient refers to an amount sufficient to elicit the desired biological response. As will be appreciated by those of ordinary skill in this art, the effective amount of a polymer of the invention may vary depending on such factors as the desired biological endpoint, the pharmacokinetics of the active ingredient, the disease being treated, the mode of administration, and the age, health, and condition of the subject. An effective amount encompasses therapeutic and prophylactic treatment.

As used herein, and unless otherwise specified, a "therapeutically effective amount" of an active ingredient is an amount sufficient to provide a therapeutic benefit in the treatment of a disease, disorder or condition, or to delay or minimize one or more symptoms associated with the disease, disorder or condition. A therapeutically effective amount of an active ingredient means an amount of the active ingredient, alone or in combination with other agents or therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of an active ingredient is an amount sufficient to prevent a disease, disorder or condition, or one or more symptoms associated with the disease, disorder or condition, or prevent its recurrence. A prophylactically effective amount of an active ingredient means an amount of the active ingredient, alone or in combination with other agents or therapies, which provides a prophylactic benefit in the prevention of the disease, disorder or condition. The term "prophylactically effective amount" can encompass an amount that improves overall prophylaxis or enhances the prophylactic efficacy of another prophylactic agent.

EXAMPLES

Example 1

Figure 1B:
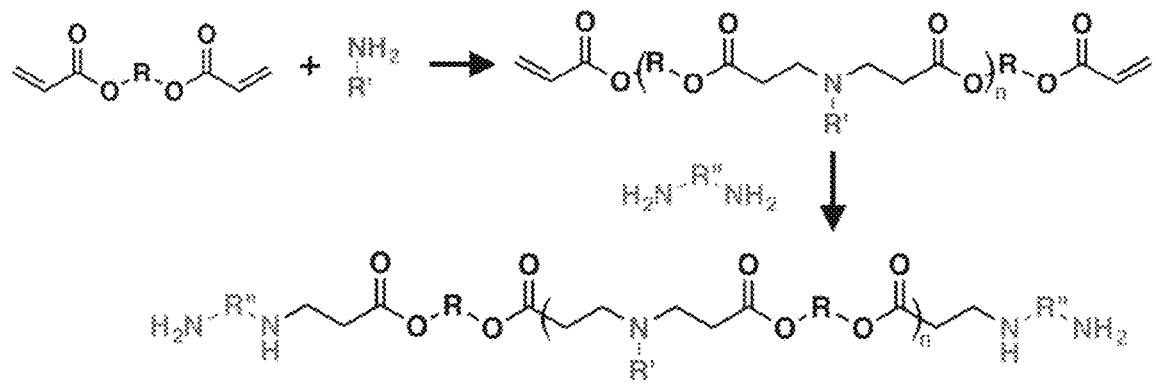
Figure 1C:
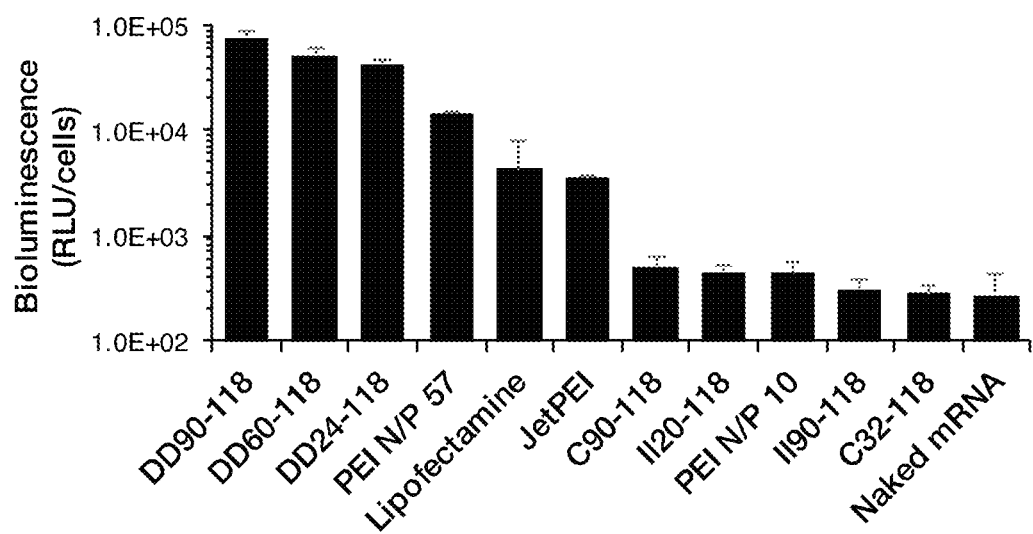

The chemical composition of linear PBAEs was optimized for mRNA delivery to A549 lung epithelial cells using a sub-set of monomers shown in FIG. 1A. Linear PBAEs were synthesized via Michael addition of a diacrylate (A2) to a primary or bis-secondary amine (B2) (FIG. 1B). The polymers were then end-capped with amines. It was established that PBAE 'DD90-118' displayed the highest transfection efficiency in vitro (FIG. 1C). DD90-118 was selected to further investigate the effect of manipulating polymer architecture.

Example 2

Figure 2A:
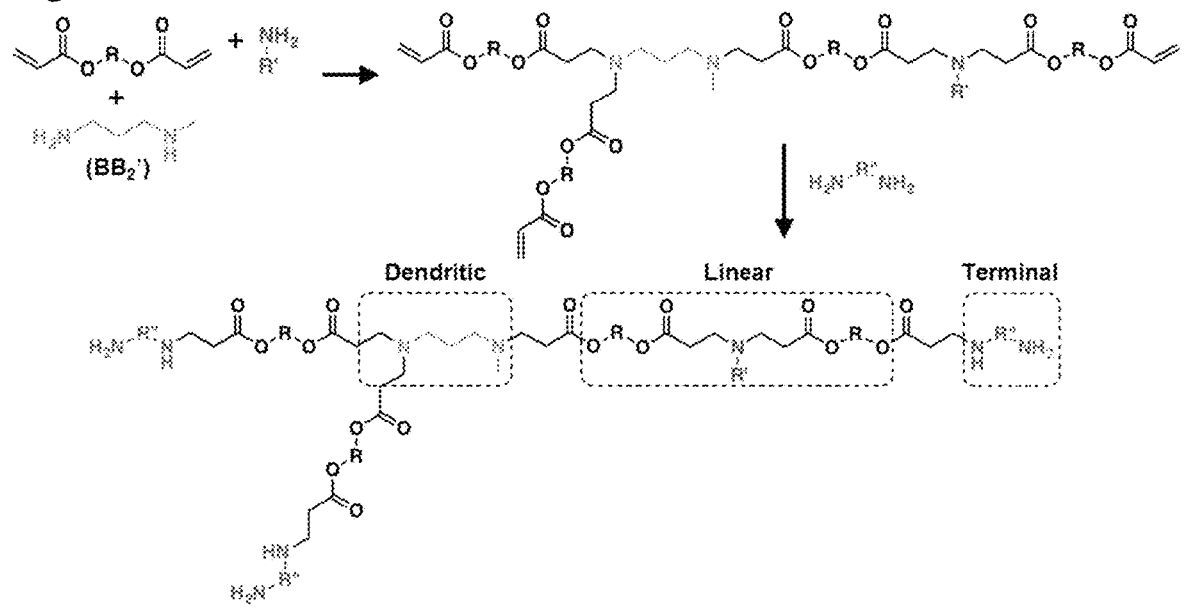
FIGS. 2A-2B.
Figure 2B:
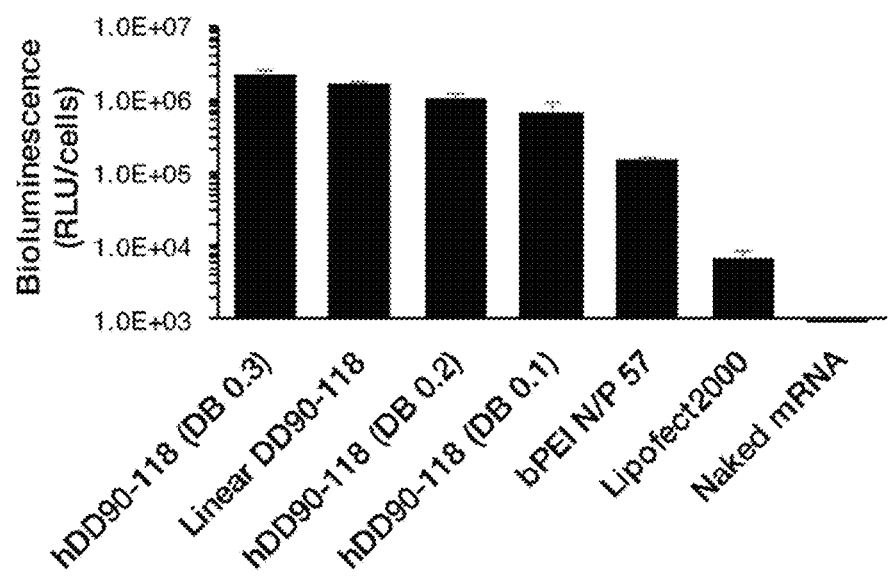
Figure 3A:
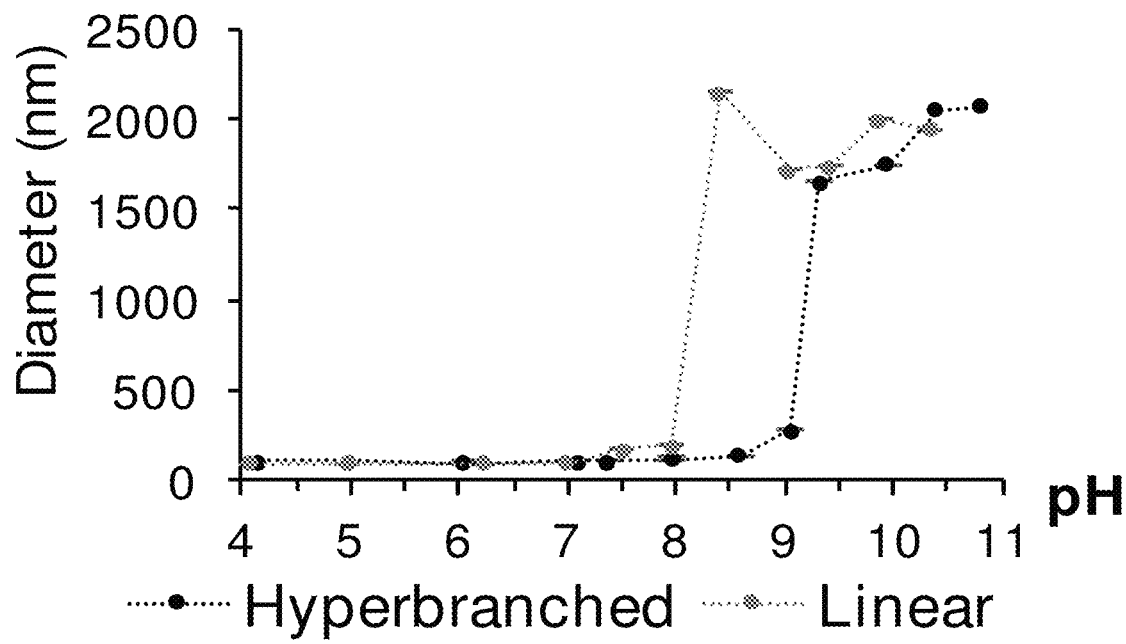
FIGS. 3A-3C.
Figure 3B:
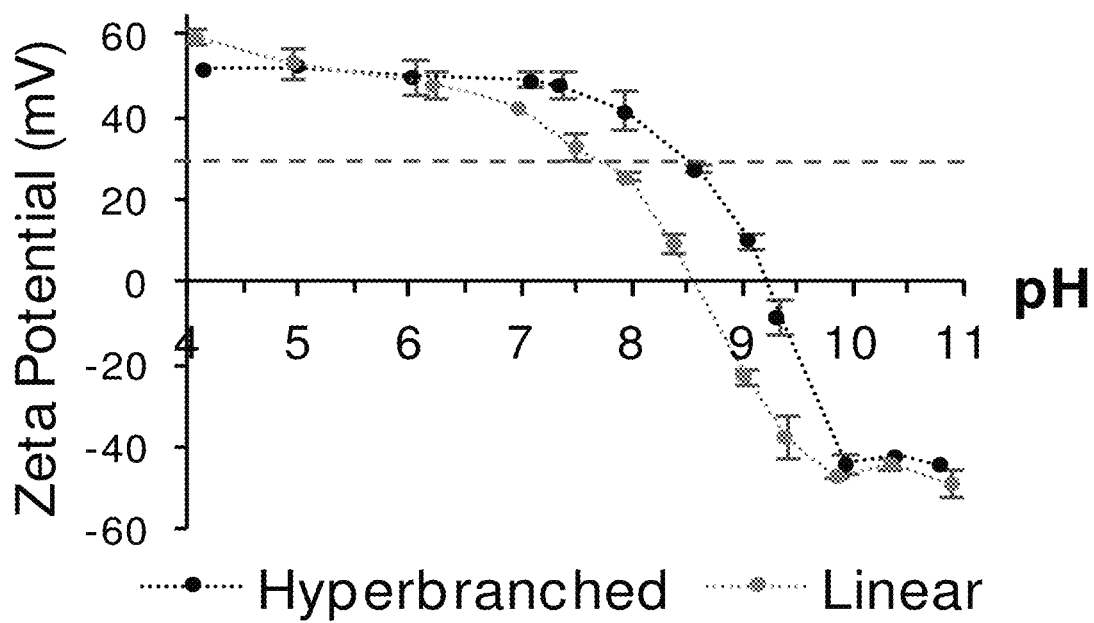
Figure 3C:
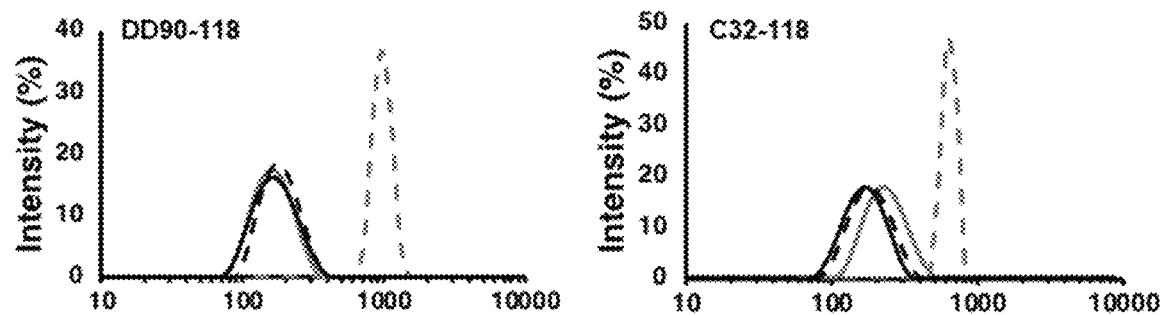
Figure 4A:
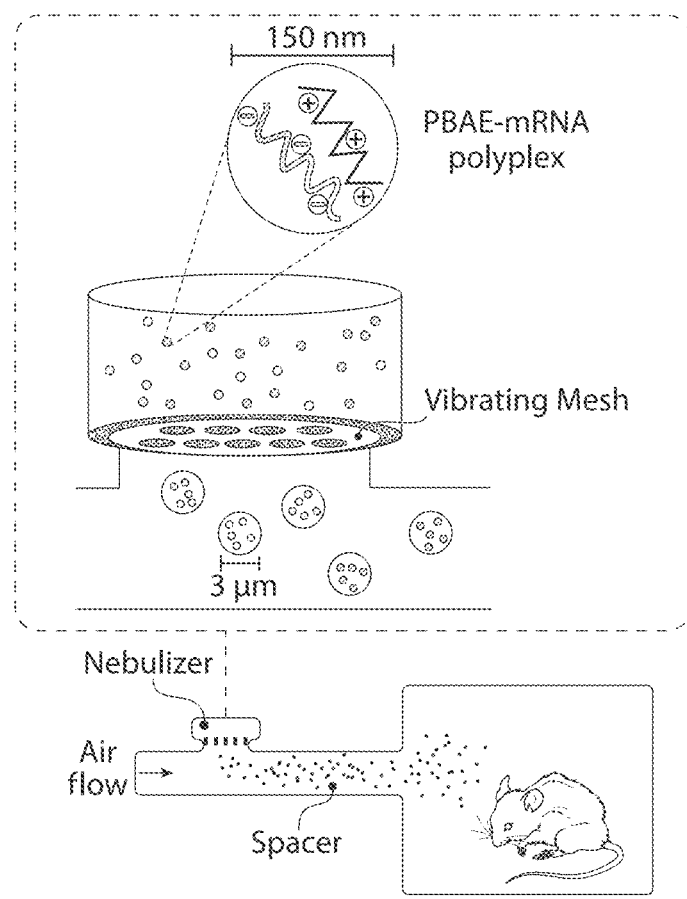
FIGS. 4A-4H.
Figure 4B:
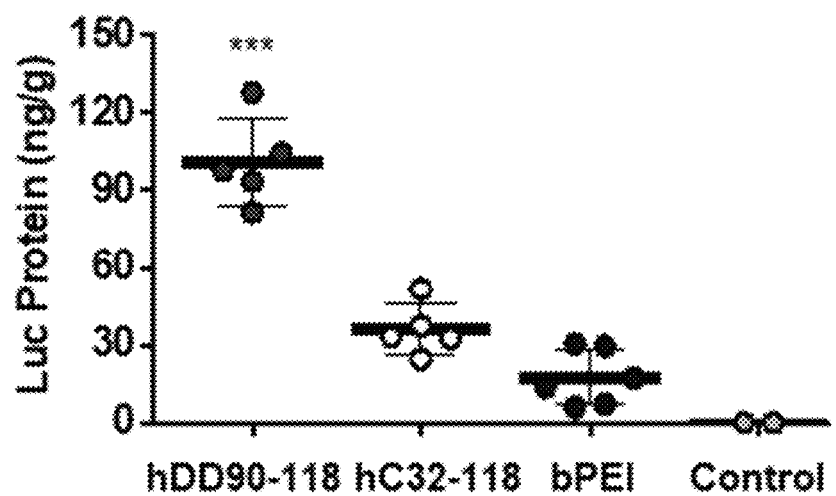
Figure 4C:
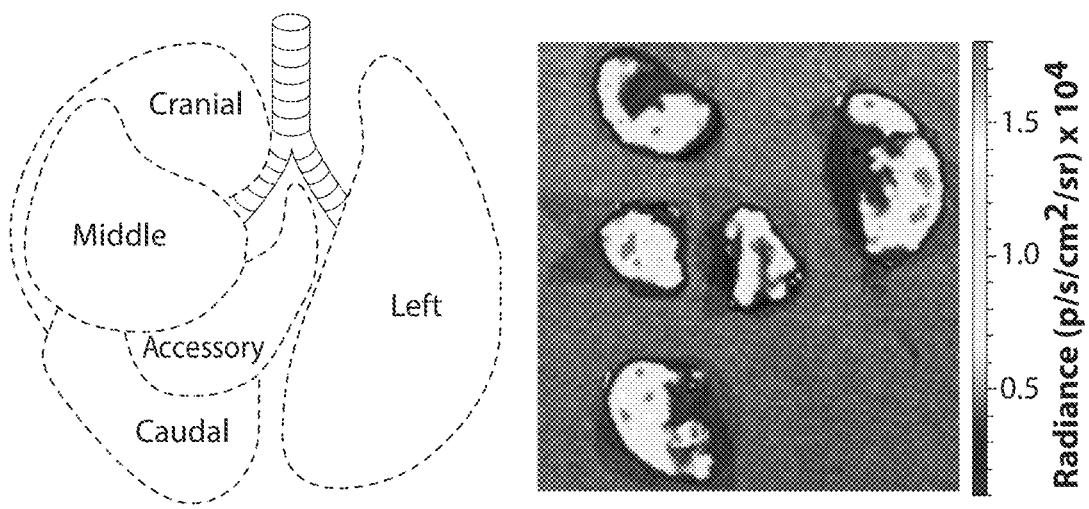
Figure 4D:
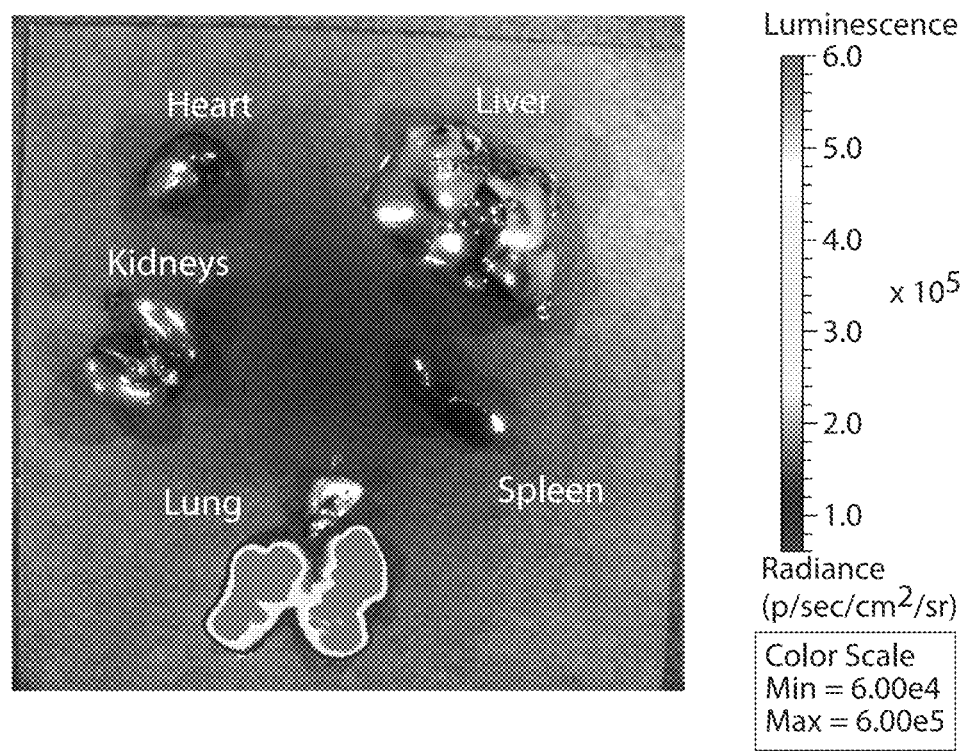
Figure 4E:
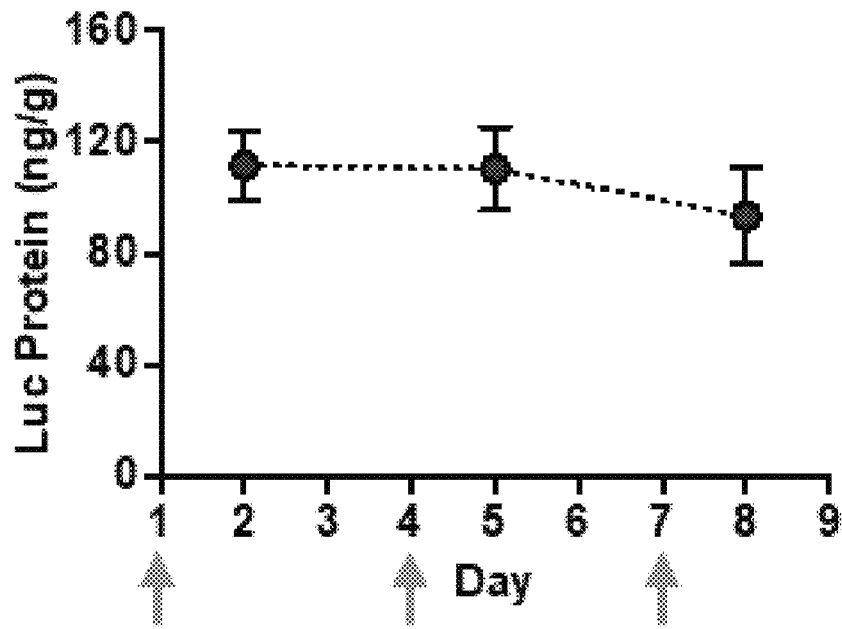
Figure 4F:
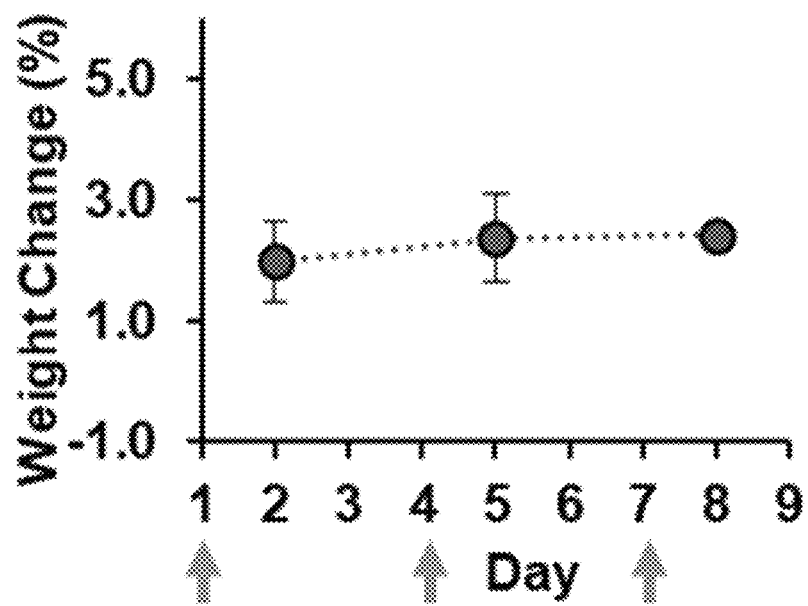
Figure 4G:
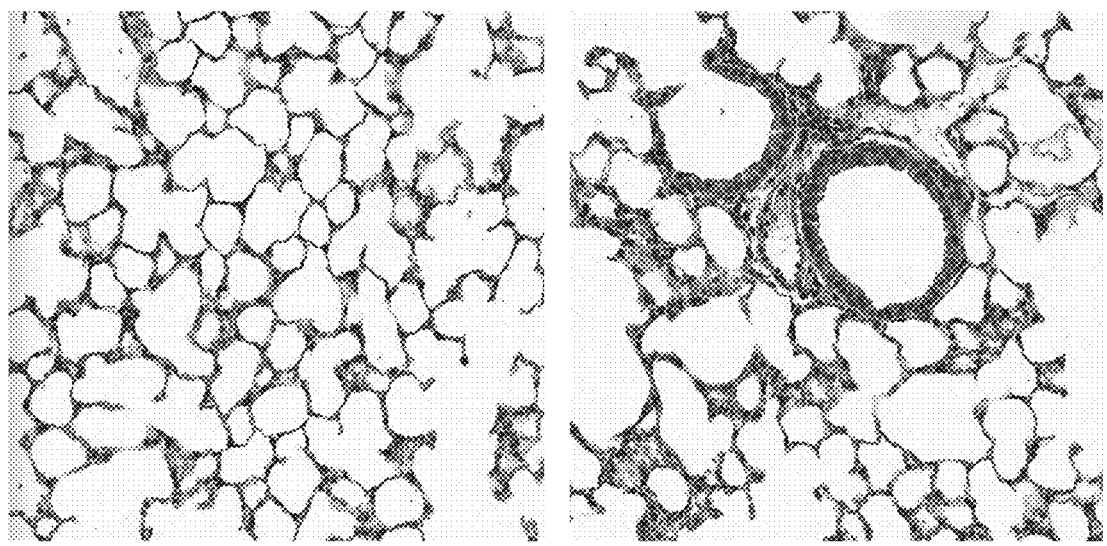
Figure 4H:
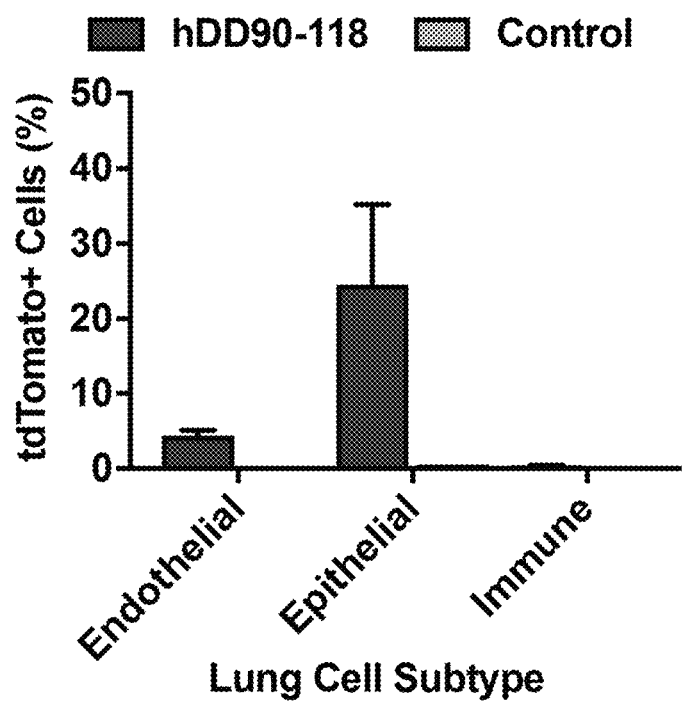

Hyperbranched PBAE polymers were synthesized using an $A_2$, $B_2$, $BB'_2$ synthesis strategy. Monombers DD, 90, and a multifunctional amine, N-methyl 1,3 diaminopropane ($BB'_2$) were reacted (FIG. 2A). To control DB, the monomer feed ratio of amine '90' ($B_2$) to branching amine ($BB'_2$) was varied to generate hyperbranched PBAEs with a DB of 0.1, 0.2 and 0.3 (FIG. 2B) as confirmed by $^1H$ NMR which showed good agreement between theoretical and experimental values. Hyperbranched (hDD90) and linear DD90 polymers were end capped with di-primary amine 118. The linear DD90-118 and three hDD90-118 polymers had molecular weights between 15-24 kDa as determined by triple detection GPC.

Figure 6A:
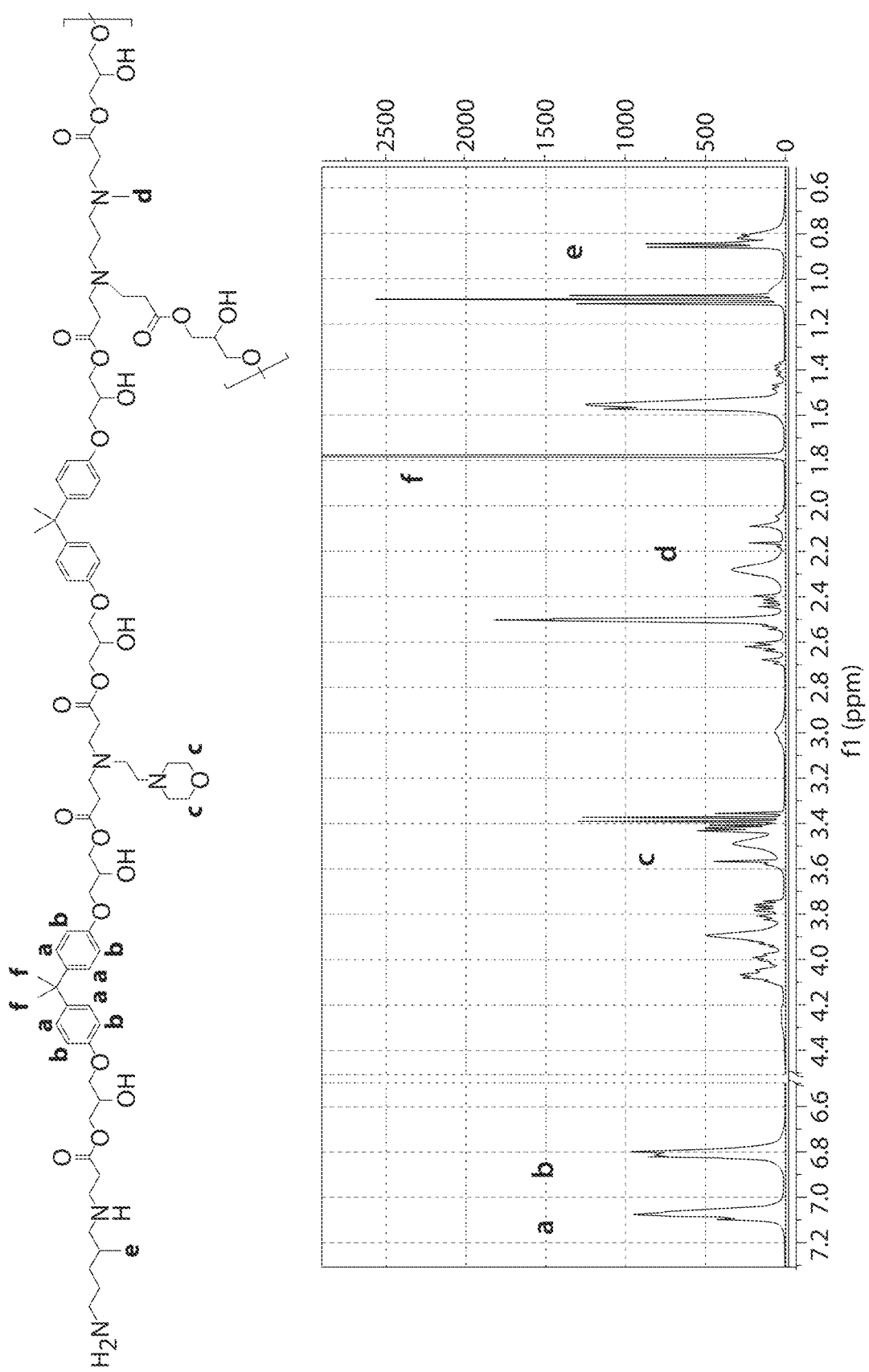
FIGS. 6A-6C.
Figure 6C:
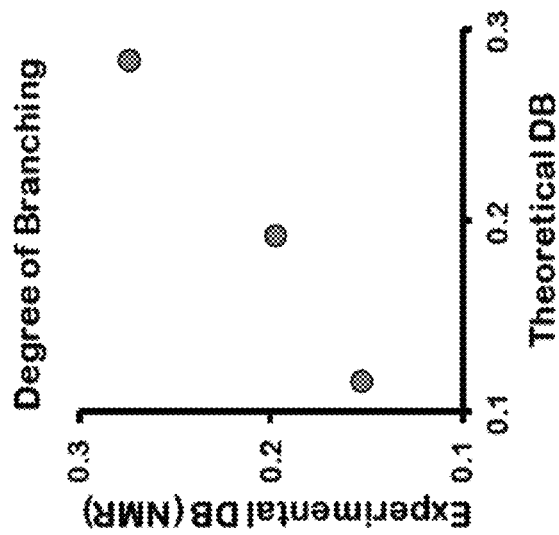
Figure 6B:
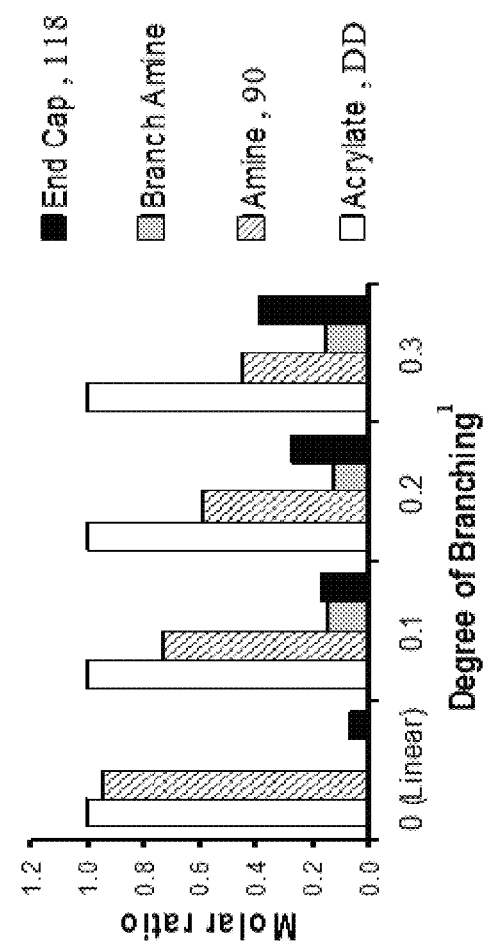
Figures 7A, 7B:
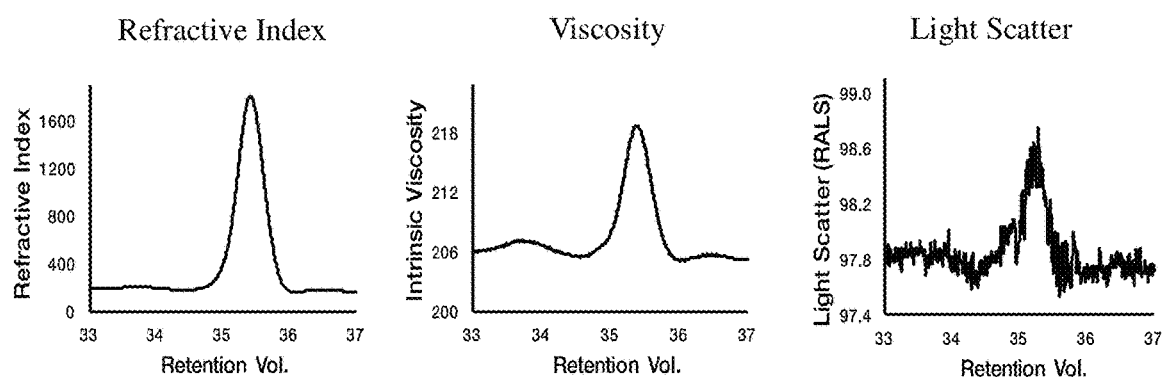
FIGS. 7A-7B.
Figure 8:
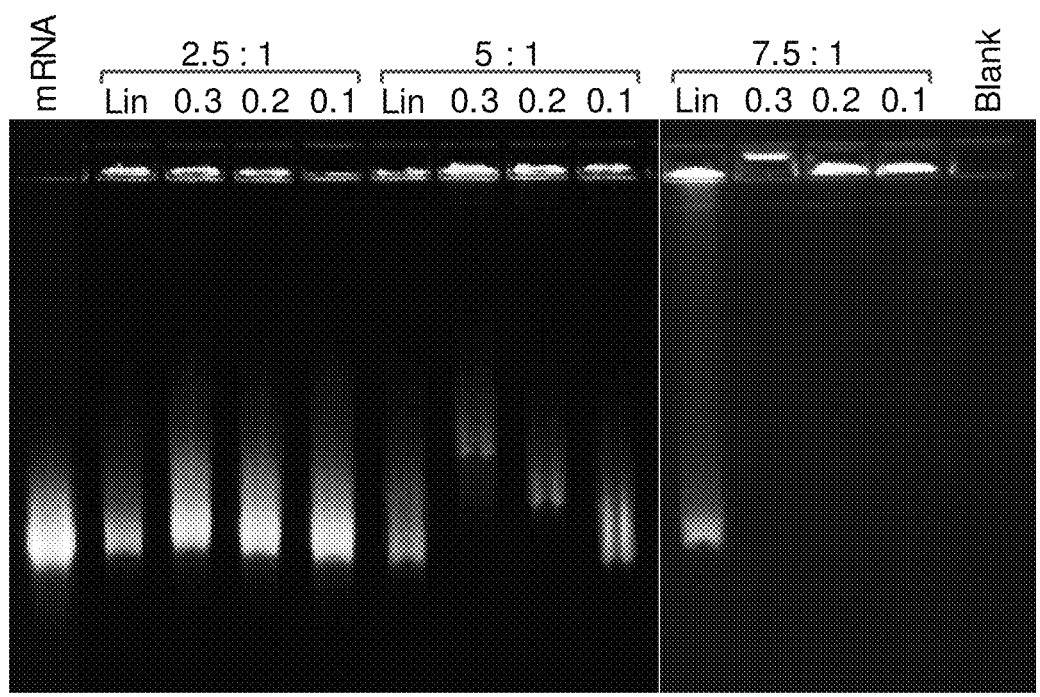
FIG. 8 shows that gel electrophoresis was used to assess ability of nanoparticle complex to retard mobility. Linear DD90-118 (Lin) and hyperbranched hDD90-118 with degree of branching 0.3, 0.2, and 0.1 are complexed with mRNA at three mass ratios of polymer to nucleic acid 2.5 to 1, 5 to 1, and 7.5 to 1. None of the polymers could retard mRNA at a ratio of 2.5 to 1. At a ratio of 5 to 1, hDD90-188 with a DB of 0.3 could retard mRNA greater than the other PBAEs. All hyperbranched polymers could retard mobility at 7.5 to 1 but not linear.
Figure 9A:
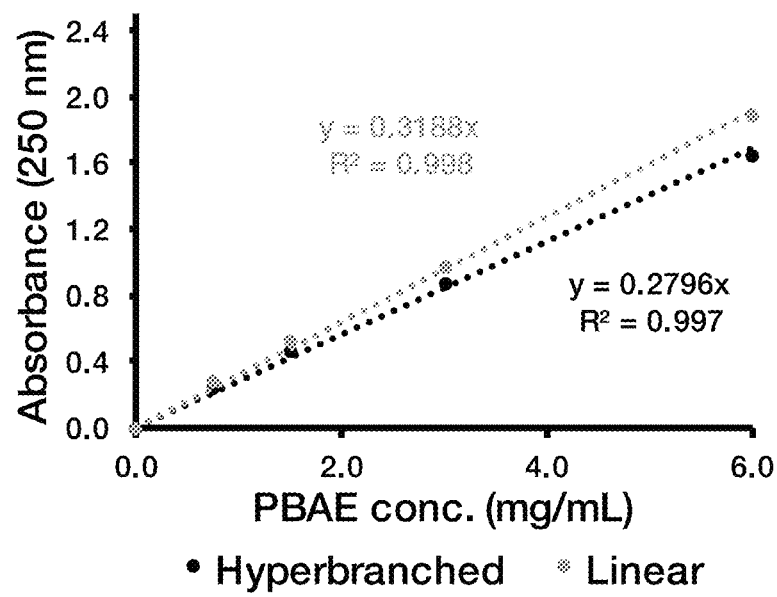
FIGS. 9A-9B depict the aqueous solubility at pH 5.2.
Figure 9B:
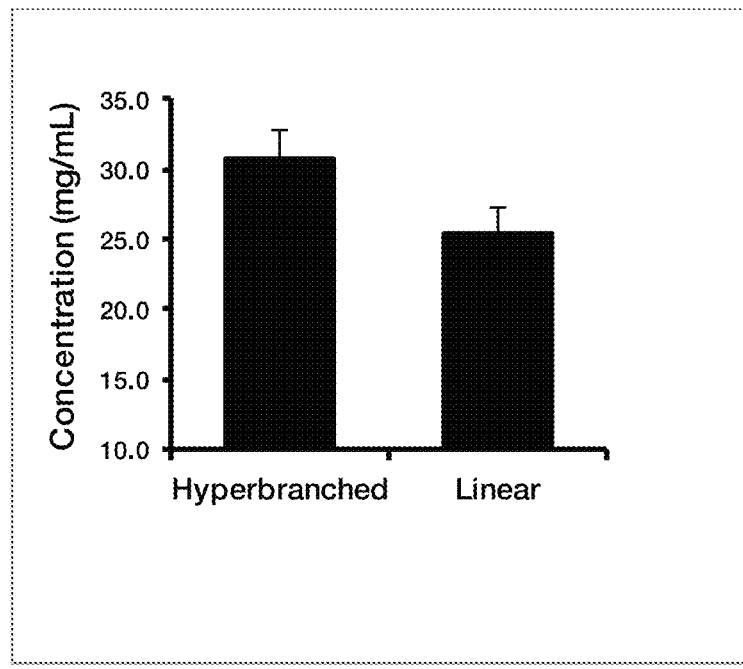
Figure 10A:
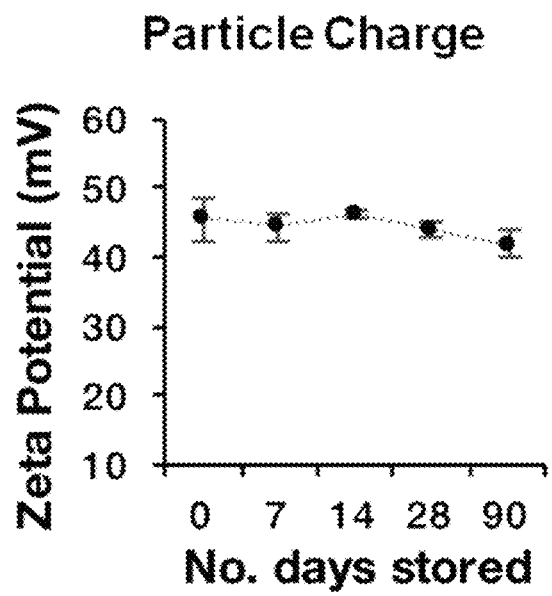
FIGS. 10A-10C depict stability and efficacy after storage of lyophilized samples at −80° C. (n=3, ±S.D). Zeta potential (FIG. 10A), diameter (FIG. 10B), and radiance (FIG. 10C) were measured.
Figure 10B:
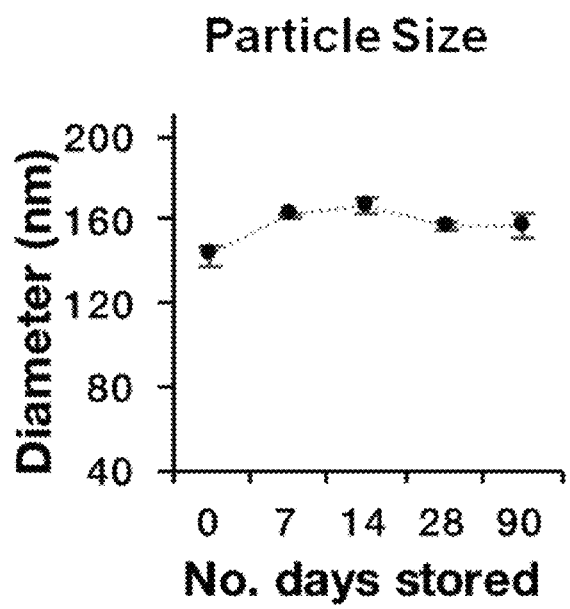
Figure 10C:
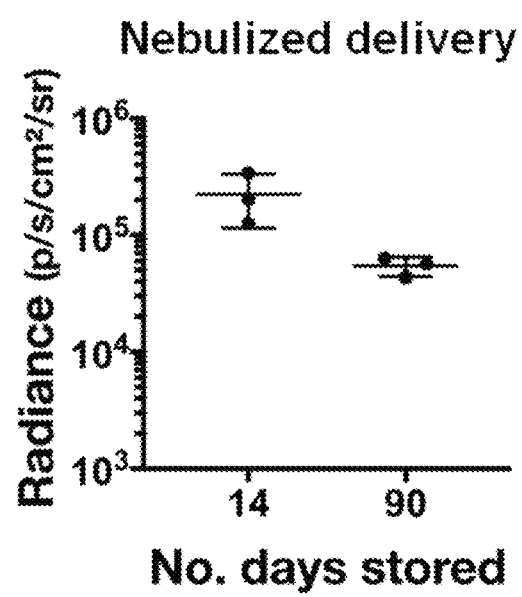
Figure 11:
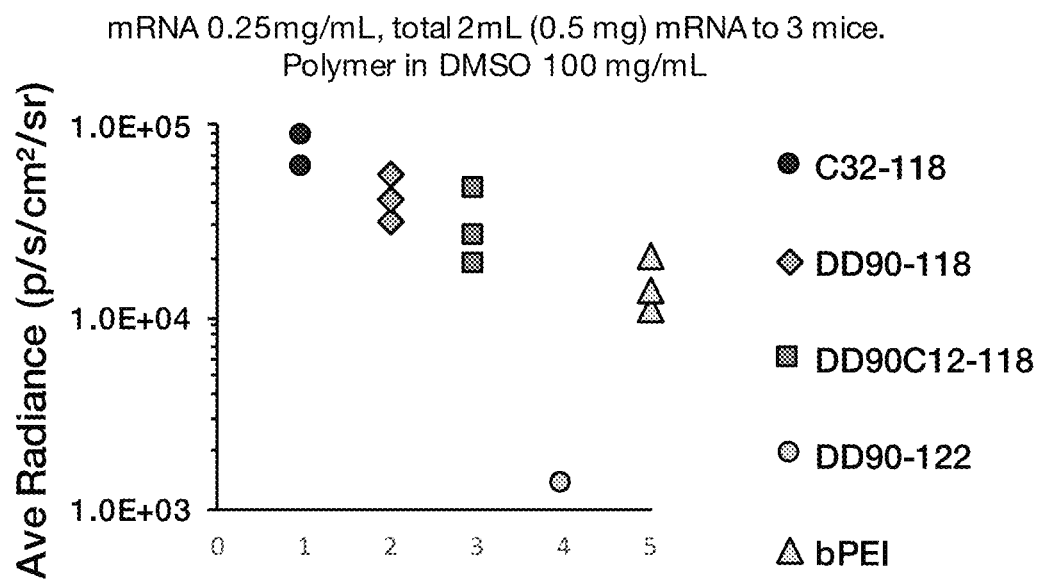
FIG. 11 shows the average radiance measured in the mice after nebulization. Linear PBAEs were nebulized 0.25 mg/mL, 2 mL total (0.5 mg) mRNA to three mice.
Figure 12:
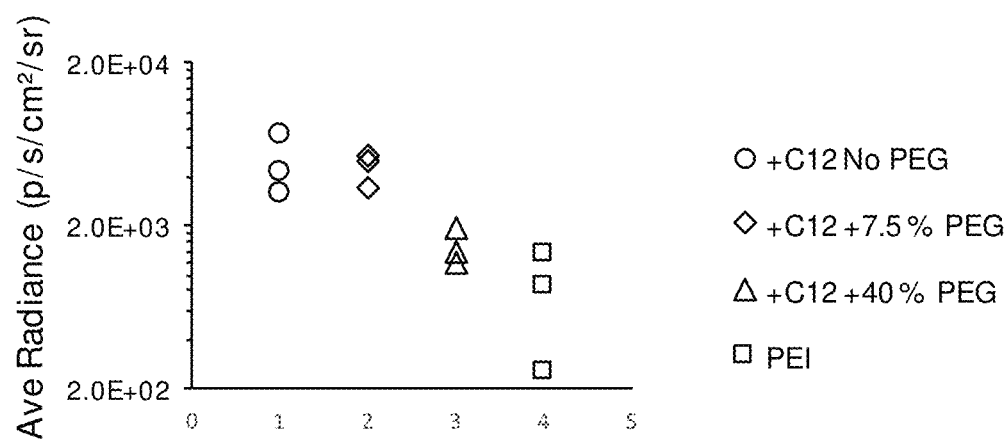
FIG. 12 shows the average radiance measured in three mice after the addition of PEG-lipid and a lower dose of mRNA 0.15 mg.

$^1H$ NMR analysis indicated that an increase in DB correlates with an increase in terminal 'end-cap' amine groups (FIG. 6A). These end-cap amines consequently increase the density of primary and secondary amines in the PBAE and may influence polymer efficacy as a transfection reagent at various stages. Initially, during nanoparticle formulation, the cationic polymer protects nucleic acid cargo through electrostatic condensation to prevent degradation by nucleases. This was illustrated in a gel retardation assay, where the hyperbranched PBAEs were able to keep mRNA protected within polyplex and prevent movement through the gel at a lower N/P ratio of 5, whereas the linear polymer could not. (FIGS. 7A and 7B).

Figure 5A:
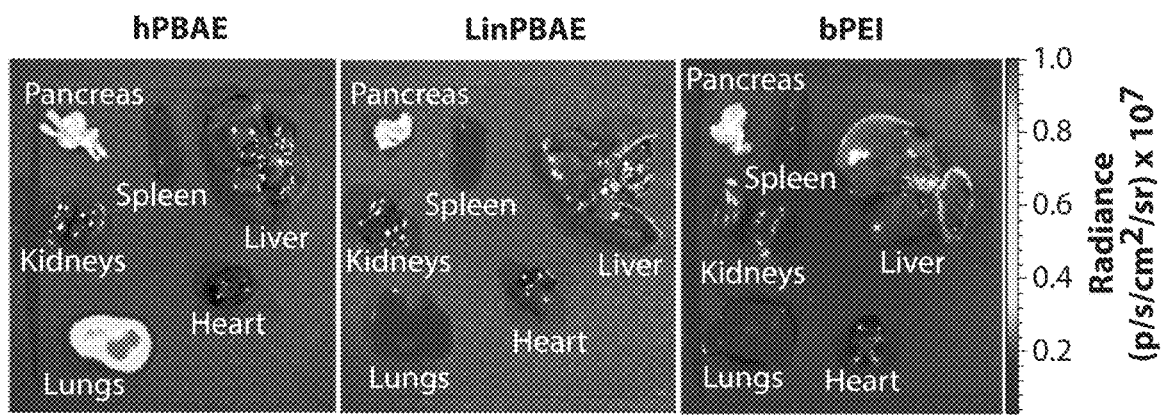
FIGS. 5A-5E.
Figure 5B:
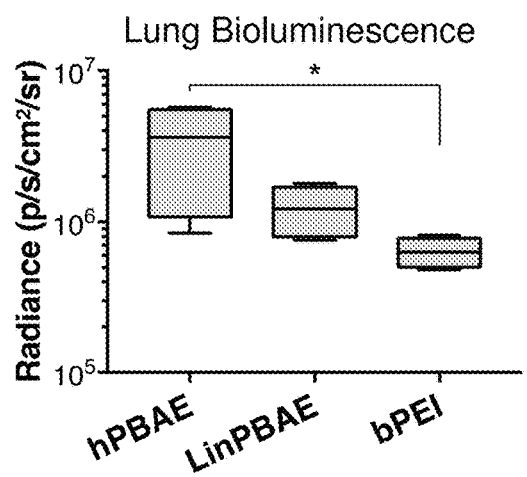
Figure 5C:
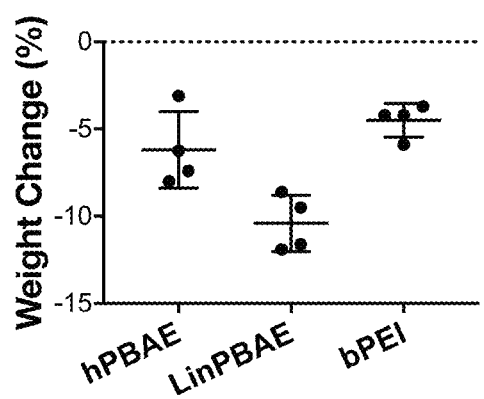
Figure 5D:
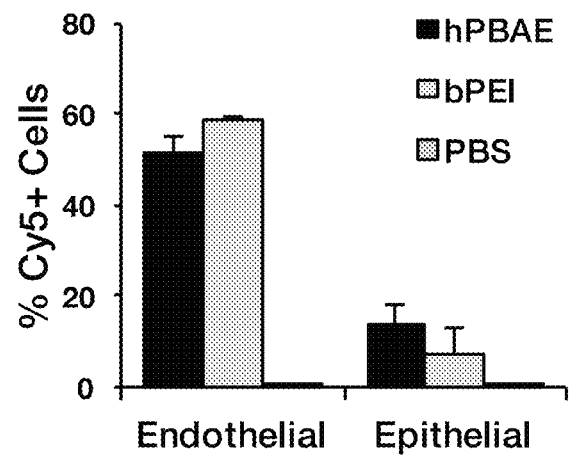
Figure 5E:
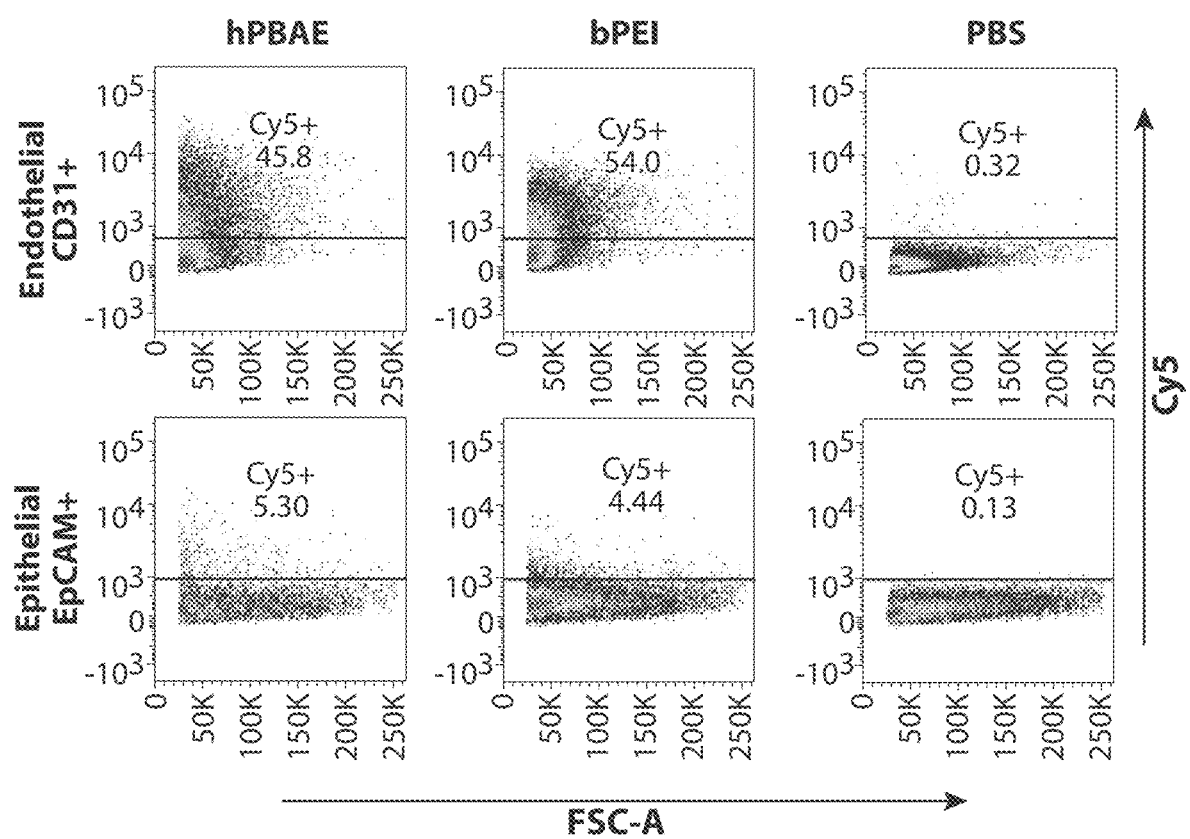

On the basis of the high transfection efficiency observed in vitro (FIG. 2C) and effective mRNA binding (FIGS. 7A and 7B), hDD90-118 with a DB of 0.3 (referred to as "the hPBAE") was selected to take forward for in vivo nebulization of mRNA. Properties pertinent to aerosol formulation were characterized, including polymer aqueous solubility and nanoparticle stability. Using UV spectroscopy, an increase in aqueous solubility for the hPBAE (30.8 mg/mL) was observed compared as to linear DD90-118 (25.4 mg/mL) at pH 5.2, notably in the absence of solvents traditionally required to increase solubility such as dimethyl sulfoxide (FIG. 8). This increase in solubility of the hPBAE is likely due to the increase in polar end groups (FIGS. 6A and 6B) and is a substantial benefit, particularly for nebulized delivery where concentrated doses are required for clinically relevant levels of gene delivery. Particle stability against pH was tested, and it was found that particle diameter remained below 100 nm between pH 4 to 7 for both branched and linear PBAEs. However, upon increasing pH, hPBAE nanoparticles remained below 120 nm up to pH 8.5 compared to linear PBAEs, which began to grow in size at pH 7.5 (168 nm) and aggregated above pH 8 (FIG. 3). The loss of particle stability correlates to a reduction in zeta potential below +30 mV, which occurs at around pH 7.5 for linear PBAE and pH 8.5 for branched (FIG. 3) suggesting that a charge above +30 mV is required for colloidal stability of these nanoparticles in the absence of steric stabilization such as that afforded by polyethylene glycol (PEG) coatings.

Example 3

Polyplexes containing firefly luciferase-encoding mRNA were prepared with linear or branched DD90-118 at a polymer concentration of 25 mg/mL, and used a 50:1 mass ratio of polymer to mRNA. bPEI 25 kDa was also prepared at an equivalent N/P ratio of 57. A vibrating mesh nebulizer was used to aerosolize the nanoparticle formulations and after confirming that particle size and charge remained stable after this process (FIGS. 9A and 9B), 1 mL of the formulation was nebulized to mice via a whole-body chamber (FIG. 4A). Both linear and branched PBAE were found to transfect the lung and express significantly higher bioluminescence than the bPEI 25 kDa. In addition, the nanoparticles were lyophilized with sucrose as a cryoprotectant, stored at −80° C. and reconstituted in water to a concentration of 0.5 mg/mL mRNA prior to nebulization, adding a significant benefit for ease of preparation. Particles were used 48 h post-lyophilization. However, there is potential for longer term storage as hPBAE particles remained stable and effective in vivo after 14 and 90 days of storage at −80° C. (FIGS. 9A and 9B). After 24 hours, organs were harvested from mice and bioluminescence was found to be significantly higher in the lung when luciferase mRNA was delivered using hPBAE polyplexes ($3.2\times10^5$ p/s/cm$^2$/sr) compared to bPEI ($2.4\times10^4$, p=0.003) (FIG. 4B). Uniform distribution of bioluminescence was achieved throughout all 5 lobes of the lung (FIG. 4C) and translation of luciferase mRNA was localized to the lung with no bioluminescence observed in the liver, kidneys, spleen or heart (FIG. 4D). All nebulized delivery vectors were well tolerated in mice as indicated by no significant weight loss (FIG. 4E) and absence of lung inflammation assessed by histology at 48 h post-nebulization (FIG. 4F).

A sensitive cell specific approach using Ai14 reporter mice was used to identify the lung cell subtype that was being transfected by the branched hDD90-118 formulation. The mice harbor a loxP-flanked stop cassette that controls gene expression of the highly fluorescent tdTomato protein and is only expressed in the presence of Cre recombinase. hDD90-118 (DB 0.3) polyplexes containing mRNA encoding for Cre-recombinase were nebulized to mice. After 7 days, lungs were analyzed by flow cytometry, revealing that the lung epithelial cell population expressed the majority of tdTomato (FIG. 4G), compared to endothelial or immune cells (FIGS. 10A, 10B and 10C).

To determine if the lyophilized formulations could also be utilized in an alternative, commonly-reported delivery route, luciferase mRNA was administered at a dose of 0.5 mg/kg to mice via intravenous injection. Interestingly, after systemic delivery, bioluminescence remained highest in the lung for the cationic polyplexes (FIG. 5). Bioluminescence in the lung was significantly higher in mice administered with hDD90-118 polyplexes ($4.0\times10^6$) compared to bPEI ($1.1\times10^6$, p=0.01) and caused lower weight loss than the linear DD90-118, indicating reduced toxicity (FIG. 5C). Further analysis of the lung by flow cytometry found that hDD90-118 polyplexes transfected 51.8% of the lung endothelial cell population and 13.8% of the epithelial cell population (FIGS. 10A, 10B and 10C). In contrast to local nebulized lung delivery, systemic administration also generated detectable levels of bioluminescence in the spleen (FIG. 5A).

Example 4: Poly(Beta Amino Ester) Synthesis

Diacrylate and amine monomers were purchased from Sigma-Aldrich, Alfa Aesar, TCI America and Monomer-Polymer & Dajac Labs. Linear PBAEs were synthesized at a ratio of 1:0.95 acrylate:backbone amine. To synthesize hyperbranched PBAEs (hPBAEs), monomers were reacted at varying stoichiometry (shown below) to achieve different degrees of branching: Molar ratio of Acrylate (e.g., Formula (A)): backbone amine (e.g., combined Formula (B) and/or (E)): branching amine (e.g., Formula (C)):
  a) 1:0.5:0.2 (DB=0.3);
  b) 1:0.67:0.13 (DB=0.2); or
  c) 1:0.8:0.08 (DB=0.1).

Monomers were combined in anhydrous dimethylformamide at a concentration of 150 mg/mL and held at a temp of 40 C for 6 h followed by an increase in temp to 90 C, stirred at 90° C. for 48 hours and then allowed to cool to 30° C. The end cap amine (e.g., Formula (D)) was then added at an excess of 1.25 molar equivalents relative to the acrylate and stirred for a further 24 hours. The polymer was protonated and purified by dropwise precipitation into cold anhydrous diethyl ether spiked with glacial acetic acid. This was vortexed rigorously and centrifuged at 1250 G for 2 mins to pellet the polymer. The supernatant was discarded and polymer washed twice more in fresh diethyl ether and dried under vacuum for 48 hours. The polymers were stored at −20° C.

Example 5: In Vitro Transfection

A549 lung epithelial cells (ATCC) were seeded into white tissue culture polystyrene 96 well plates (Corning) at 10,000 cells per well in 100 uL of DMEM medium (Invitrogen) supplemented with 10% fetal bovine serum and 1% antibiotic-antimycotic (Gibco). After 24 hours of incubation, each well was transfected with 50 ng of mRNA encoding for firefly luciferase (Shire) either naked or complexed with transfection reagents. Lipofectamine 2000 (Invitrogen) and JetPEI (Polyplus) were prepared according to manufacturer's instructions. Branched PEI 25 kDa (Sigma) was diluted in water to a concentration of 7.5 mg/mL and titrated to pH 5. The polymer was combined with mRNA at an N/P ratio of 57, pipetted several times to mix and allowed to stand at room temp. for 10 minutes to allow complex formation. Protonated PBAEs were dissolved in 25 mM sodium acetate buffer (pH 5.2, Sigma) to a concentration of 10 mg/mL and complexed with mRNA at a mass ratio of 50 to 1 and incubated at room temp. for 10 minutes to allow complex formation. Each transfection reagent was made to an mRNA concentration of 50 ng/15 uL and added to wells containing 150 uL of fresh medium. Medium was changed after 4 hours incubation. Cells were incubated for a further 20 hours at 37° C., 5% $CO_2$. Cell viability was assessed using PrestoBlue (Invitrogen) followed by luciferase expression analysis using BrightGlo (Promega) according to manufacturer's instructions.

Example 6: Lyophilization

Nanoparticles were prepared for nebulization at a mRNA concentration of 0.125 mg/mL and at 0.0125 mg/mL for intravenous delivery. Sucrose (Sigma) was added to nanoparticles at 30 mg/mL, flash frozen in liquid nitrogen and lyophilized for 24 hours. Lyophilized samples were stored at −80° C. and reconstituted in water (molecular biology grade, Sigma) to a concentration of 0.5 mg/mL mRNA for nebulization and to 0.05 mg/mL for intravenous injection.

Example 7: Animal Studies

C57BL/6 mice, 6-8 weeks old females (Charles River) were cared for in the USDA-inspected MIT Animal Facility under federal, state, local and NIH guidelines for animal care. Nebulized delivery: An AeroNeb vibrating mesh nebulizer (Aerogen Inc.) was connected to a whole-body nebulization chamber via a spacer half filled with silica (1-3 mm, Sigma). 3 mice were placed in the chamber. The nebulizer was loaded with 1 mL of a nanoparticle formulation containing 0.5 mg/mL of IVT-mRNA encoding for firefly luciferase (kindly provided by Shire Pharmaceuticals, Lexington Mass.). An oxygen flow rate of 20 was used to direct the aerosol along the spacer into the chamber until no more aerosol could be observed. Intravenous delivery: Mice were injected intravenously through the tail vein with a dose of 0.5 mg/kg mRNA encoding for firefly luciferase. After 24 hours, mice were injected with 0.2 mg/g of Luciferin (Xenolight, PerkinElmer) intra-peritoneally and sacrificed 10 minutes post-injection. Organs were harvested and luciferase expression assessed by bioluminescence imaging (Xenogen IVIS Spectrum Imager).

Example 8: Flow Cytometry Studies with Ai14 Cre Reporter Mice

B6. Cg-Gt(ROSA)26Sor$^{tm14(CAG-tdTomato)Hze}$/J mice (Jackson Laboratory, Bar Harbor, Me.) were nebulized with 1 mL of hPBAE nanoparticles loaded with 0.5 mg/mL mRNA encoding for Cre Recombinase (Trilink, NLS-Cre, 5 meC, Ψ). Nanoparticles were prepared according to the protocol described earlier. As a control, genetically normal C57BL/6 mice were nebulized with water containing 100 mM sodium acetate and 60 mg/mL glucose. Mice were sacrificed 7 days post-nebulization and the lungs harvested. The lungs were minced and incubated for 1 hr at 37° C. in PBS buffer (Gibco) containing 0.92 M HEPES (Gibco), 201.3 units/mL collagenase I (Sigma), 566.1 units/mL collagenase XI (Sigma), and 50.3 units/mL DNase I (Sigma). The digested tissue was filtered through a 70 μM nylon cell strainer and treated with red blood cell (RBC) lysis buffer for 5 minutes. Following RBC lysis, the cell suspension was centrifuged at 400 G and the pellet re-suspended in PBS containing 0.5% bovine serum albumin and filtered through a 40 μM cell strainer. The single cell suspension was centrifuged again, pellet re-suspended, and then incubated for 30 minutes at 4° C. with antibodies against epithelial (EPCAM-APC), endothelial (CD31-AF488), and immune (CD45-BV421) cell markers at a 1:300 dilution (all antibodies obtained from BioLegend, San Diego, Calif.). The cells were then analyzed using an LSR HTS-II flow cytometer (BD Biosciences).

Methods

Proton nuclear magnetic resonance ($H^1$ NMR): Polymer was dissolved in deuterated dimethyl sulfoxide (DMSO-d6, Sigma). Spectra were acquired using a Bruker spectrometer (400 MHz). Chemical shifts are reported in ppm (δ) referenced against the DMSO solvent peak at 2.50 ppm. Data were processed using MestReNova software (MestRelab Research).

Gel Permeation Chromatography: Non-protonated PBAE polymer was dissolved into anhydrous tetrahydrofuran (THF) at a concentration of 5 mg/mL and filtered through a 0.2 pm PTFE filter. Absolute molecular weight and intrinsic viscosity was recorded using an Agilent 1260 Infinity multi-detector instrument equipped with a viscometer and detectors for refractive index and light scattering. Data was acquired at 35° C. at a flow rate of 1 mL/min. Analysis was performed using OmniSEC software.

Gel electrophoresis retardation assay: Polyplexes were prepared at a mRNA concentration of 0.1 mg/mL and at polymer mass ratios to mRNA of 2.5, 5.0 and 7.5 to 1 in water (Molecular biology grade, Sigma). A 20 µL sample was loaded per well of a SybrGold 1% agarose EX E-Gel and run on an iBase (Invitrogen) for 10 minutes, then imaged on a BioRad ChemiDoc system.

Solubility Assay: A calibration curve was first generated by dissolving PBAE polymer in 25 mM sodium acetate (NaOAc) buffer (Sigma, pH 5.2) at 6 mg/mL and 3 mg/mL. These were serially diluted 1 in 2 until a concentration of 0.75 mg/mL was obtained. Absorbance at 250 nm of 100 µL of each dilution was measured in a UV transparent 96 well polystyrol plate (Corning). To test solubility, a supersaturated sample was prepared by adding excess polymer (40 mg/mL) into 25 mM NaOAc buffer and sonicated for 30 minutes. The sample was filtered through a 0.2 pm PTFE filter and serial dilutions of the filtrate prepared. Absorbance was measured at 250 nm and concentration of the samples calculated using the calibration curve.

Particle Stability over varying pH: Polyplexes were prepared at an mRNA concentration of 0.25 mg/mL and PBAE to mRNA mass ratio of 50 to 1 in 25 mM NaOAc, 0.8 mL of particles were added to 9.2 mL of deionized water. Zeta potential and particle diameter was measured using a Malvern Zetasizer Nano instrument equipped with a pH auto-titrator and probe (MPT-2). Hydrochloric acid and sodium hydroxide were used to titrate pH from 4 to 11.

Histology: After administering 3 repeat doses to mice, they were sacrificed at 24 hours post-nebulization. Lungs were inflated with 4% paraformaldehyde injected through the trachea. The trachea was tied and lungs submerged in 4% paraformaldehyde overnight. Lungs were stored in 70% ethanol until being embedded in a paraffin block. Sections of embedded tissue were then mounted on slides and stained with hematoxylin and eosin. Slides were viewed using a Zeiss Axioplan II upright microscope at 20× magnification.

Flow Cytometry Studies with Cy5-labeled mRNA. C57 BL/6 mice were injected intravenously with polyplexes loaded with Cyanine 5-labeled luciferase-encoding mRNA (Trilink, 5 meC, ψ) at a dose of 0.5 mg/kg according to a previous protocol.[3] Control mice were injected with phosphate buffered saline. Mice were sacrificed 1 hour after injection and perfused with PBS. The lungs were harvested and imaged on an IVIS imaging apparatus. Following imaging, lungs were processed into a single cell suspension and analyzed as described in the Ai14 reporter mouse methods section. Antibodies used were CD45-BV510 (immune cells), CD31-Pacific Blue (endothelial cells), and EpCAM-PE (epithelial cells). Cell populations were identified as follows: Immune (CD45+), Endothelial (CD45−, CD31+, EpCAM−), and Epithelial (CD45−, CD31−, EpCAM+).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps.

Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:

1. A composition comprising a poly(beta-amino ester) polymer, or a salt thereof, the polymer comprising:
a diradical of Formula (A) having the structure:

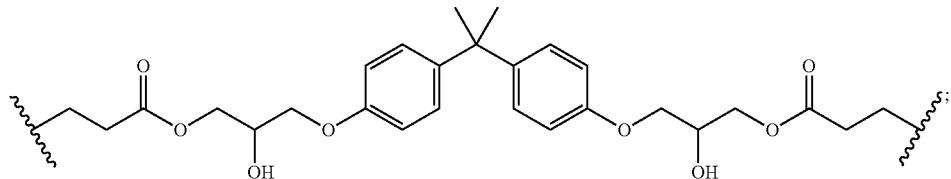

a diradical of Formula (B) having the structure:

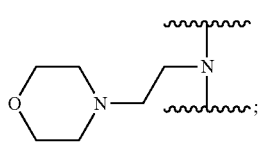

a triradical of Formula (C) having the structure:

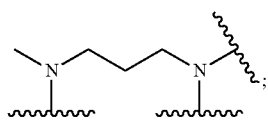

and
a radical of Formula (D) having the structure:

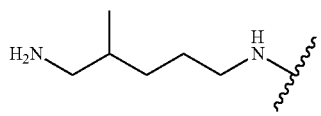

wherein:
each diradical of Formula (A) has two points of attachment to radicals independently selected from Formulae (B), (C), and (D);
each diradical of Formula (B) has two points of attachment to a diradical of Formula (A);
each triradical of Formula (C) has three points of attachment to a diradical of Formula (A); and
each radical of Formula (D) has one point of attachment to a diradical of Formula (A).

2. The composition of claim 1, wherein the polymer comprises radicals of Formulae (A), (B), (C), and (D) in a ratio of about 1:0.5:0.2:0.39; 1:0.67:0.13:0.27; 1:0.8:0.08:0.16; or 1:0.94:0:0.07.

3. The composition of claim 1, wherein the polymer has a molecular weight in the range of 10-40 kDa.

4. The composition of claim 1, wherein the polymer has a degree of branching (DB) in the range of 0.1-0.7.

5. The composition of claim 1, further comprising an agent.

6. The composition of claim 5, wherein the agent is a polynucleotide.

7. The composition of claim 6, wherein the polynucleotide is DNA.

8. The composition of claim 6, wherein the polynucleotide is RNA.

9. The composition of claim 8, wherein the RNA is mRNA, siRNA, ssRNA, dsRNA, shRNA, or miRNA.

10. The composition of claim 9, wherein the RNA is siRNA.

11. The composition of claim 6, wherein the polynucleotide encodes an antigenic peptide or protein.

12. The composition of claim 11, wherein the antigenic peptide or protein is derived from a virus.

13. The composition of claim 1, in the form of a particle.

14. The composition of claim 13, wherein the particle is a microparticle, nanoparticle, micelle, liposome, or lipoplex.

15. The composition of claim 1, formulated for nebulization, aerosol delivery, or intranasal delivery.

16. A nasal spray comprising the composition of claim 5.

17. A method of delivering a polynucleotide to a cell, comprising contacting the cell with the composition of claim 6.

18. The method of claim 17, wherein the cell is a lung epithelial cell.

19. A method of treating a disease or disorder in a subject in need of such treatment, comprising administering to the subject the composition of claim 5.

20. The method of claim 19, wherein the disease or disorder is of the lungs.

21. The method of claim 19, wherein the disease or disorder is lung cancer asthma, chronic obstructive pulmonary disease, or pulmonary fibrosis.

22. The method of claim 19, wherein said administration is intranasal administration.

23. The composition of claim 9, wherein the RNA is mRNA.

* * * * *